(12) United States Patent
Brenzel et al.

(10) Patent No.: US 8,114,123 B2
(45) Date of Patent: Feb. 14, 2012

(54) APPARATUS AND METHODS FOR TISSUE GATHERING AND SECURING

(75) Inventors: Michael P. Brenzel, St. Paul, MN (US);
Paul J. Hindrichs, Plymouth, MN (US);
Theodore P. Dale, Minneapolis, MN (US); Todd A. Krinke, Rockford, MN (US); Steven D. Kruse, St. Michael, MN (US); David M. Costello, Waconia, MN (US); Todd A. Berg, Stillwater, MN (US); John A. Roop, Crystal, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 989 days.

(21) Appl. No.: 10/943,352

(22) Filed: Sep. 17, 2004

(65) Prior Publication Data
US 2005/0075665 A1 Apr. 7, 2005

Related U.S. Application Data

(60) Provisional application No. 60/504,320, filed on Sep. 19, 2003, provisional application No. 60/506,345, filed on Sep. 25, 2003, provisional application No. 60/506,348, filed on Sep. 25, 2003, provisional application No. 60/515,870, filed on Oct. 29, 2003, provisional application No. 60/585,366, filed on Jul. 2, 2004.

(51) Int. Cl.
*A61B 17/08* (2006.01)

(52) U.S. Cl. .......... 606/213; 606/142; 606/151

(58) Field of Classification Search .......... 606/213, 606/216, 219–221, 151, 157, 139, 142, 155; 227/175.1, 179.1, 177.1
See application file for complete search history.

(56) References Cited

U.S. PATENT DOCUMENTS

| | | | |
|---|---|---|---|
| 5,171,233 A | 12/1992 | Amplatz et al. | |
| 5,486,187 A * | 1/1996 | Schenck | 606/153 |
| 5,702,421 A | 12/1997 | Schneidt | |
| 5,797,960 A | 8/1998 | Stevens et al. | |
| 5,817,113 A * | 10/1998 | Gifford et al. | 606/153 |
| 5,823,956 A | 10/1998 | Roth et al. | |
| 5,829,447 A | 11/1998 | Stevens et al. | |
| 5,855,614 A | 1/1999 | Stevens et al. | |
| 5,924,424 A | 7/1999 | Stevens et al. | |
| 6,079,414 A | 6/2000 | Roth et al. | |
| 6,152,144 A | 11/2000 | Van Der Burg et al. | |
| 6,290,674 B1 | 9/2001 | Roue et al. | |
| 6,346,074 B1 | 2/2002 | Roth et al. | |
| 6,401,720 B1 | 6/2002 | Stevens et al. | |

(Continued)

FOREIGN PATENT DOCUMENTS
WO WO 98/07375 A1 2/1998

(Continued)

*Primary Examiner* — Gary Jackson
*Assistant Examiner* — Katherine Dowe
(74) *Attorney, Agent, or Firm* — Lerner, David, Littenberg, Krumholz & Mentlik, LLP

(57) ABSTRACT

Methods and apparatus are provided that gather a patient's body tissue and then secure the gathered tissue in a reduced area utilizing a securing structure. The securing structure mainly resides on one side of the tissue to minimize or eliminate both foreign material and the amount of manipulation or activity on the other side of the tissue. The securing device is matched to the desired amount of tissue manipulation to minimize the structure. The gathered and secured tissue can surround a septal defect to obstruct or close the defect itself.

36 Claims, 48 Drawing Sheets

U.S. PATENT DOCUMENTS

| | | |
|---|---|---|
| 6,419,669 B1 | 7/2002 | Frazier et al. |
| 6,436,088 B2 | 8/2002 | Frazier et al. |
| 6,458,100 B2 | 10/2002 | Roue et al. |
| 6,537,300 B2 | 3/2003 | Girton |
| 6,562,052 B2 | 5/2003 | Nobles et al. |
| 6,641,557 B1 | 11/2003 | Frazier |
| 6,651,672 B2 | 11/2003 | Roth |
| 6,679,268 B2 | 1/2004 | Stevens et al. |
| 6,702,835 B2 | 3/2004 | Ginn et al. |
| 6,763,993 B2 * | 7/2004 | Bolduc et al. ............ 227/176.1 |
| 6,776,784 B2 | 8/2004 | Ginn et al. |
| 6,811,555 B1 * | 11/2004 | Willis et al. ................. 606/153 |
| 7,063,715 B2 * | 6/2006 | Onuki et al. ................. 606/220 |
| 2001/0041914 A1 | 11/2001 | Frazier et al. |
| 2002/0077636 A1 * | 6/2002 | Arcia et al. ................. 606/153 |
| 2002/0099389 A1 | 7/2002 | Michler et al. |
| 2002/0188318 A1 | 12/2002 | Aldrich et al. |
| 2003/0028218 A1 | 2/2003 | Bauer |
| 2003/0069593 A1 | 4/2003 | Tremulis et al. |
| 2003/0144694 A1 | 7/2003 | Chanduszko |
| 2003/0171774 A1 | 9/2003 | Freudenthal et al. |
| 2003/0187467 A1 | 10/2003 | Schreck |
| 2003/0208232 A1 * | 11/2003 | Blaeser et al. ................. 606/213 |
| 2004/0049211 A1 | 3/2004 | Tremulis et al. |
| 2004/0073242 A1 * | 4/2004 | Chanduszko ................. 606/157 |
| 2004/0153122 A1 * | 8/2004 | Palermo ........................ 606/213 |
| 2004/0176788 A1 | 9/2004 | Opolski |
| 2004/0193147 A1 | 9/2004 | Malecki et al. |

FOREIGN PATENT DOCUMENTS

| | | |
|---|---|---|
| WO | WO 02/096295 A1 | 12/2002 |
| WO | WO 03/022159 A1 | 3/2003 |
| WO | WO 03/022160 A1 | 3/2003 |
| WO | WO 03/059152 A2 | 7/2003 |
| WO | WO 03/059152 A3 | 7/2003 |
| WO | WO 03/082076 A2 | 10/2003 |
| WO | WO 03/082076 A3 | 10/2003 |
| WO | WO 03/094742 A1 | 11/2003 |
| WO | WO 03/103476 A2 | 12/2003 |
| WO | WO 03/103476 A3 | 12/2003 |

* cited by examiner

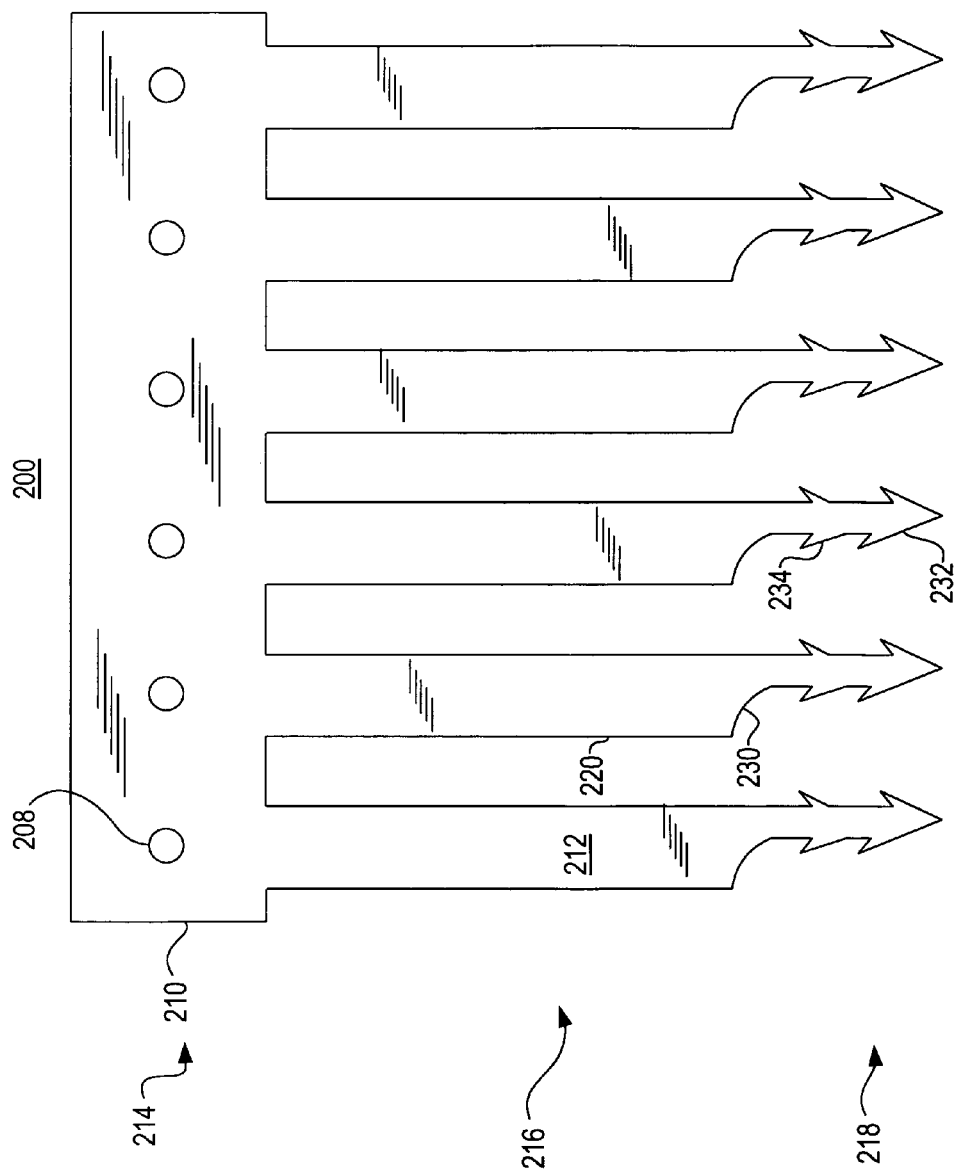

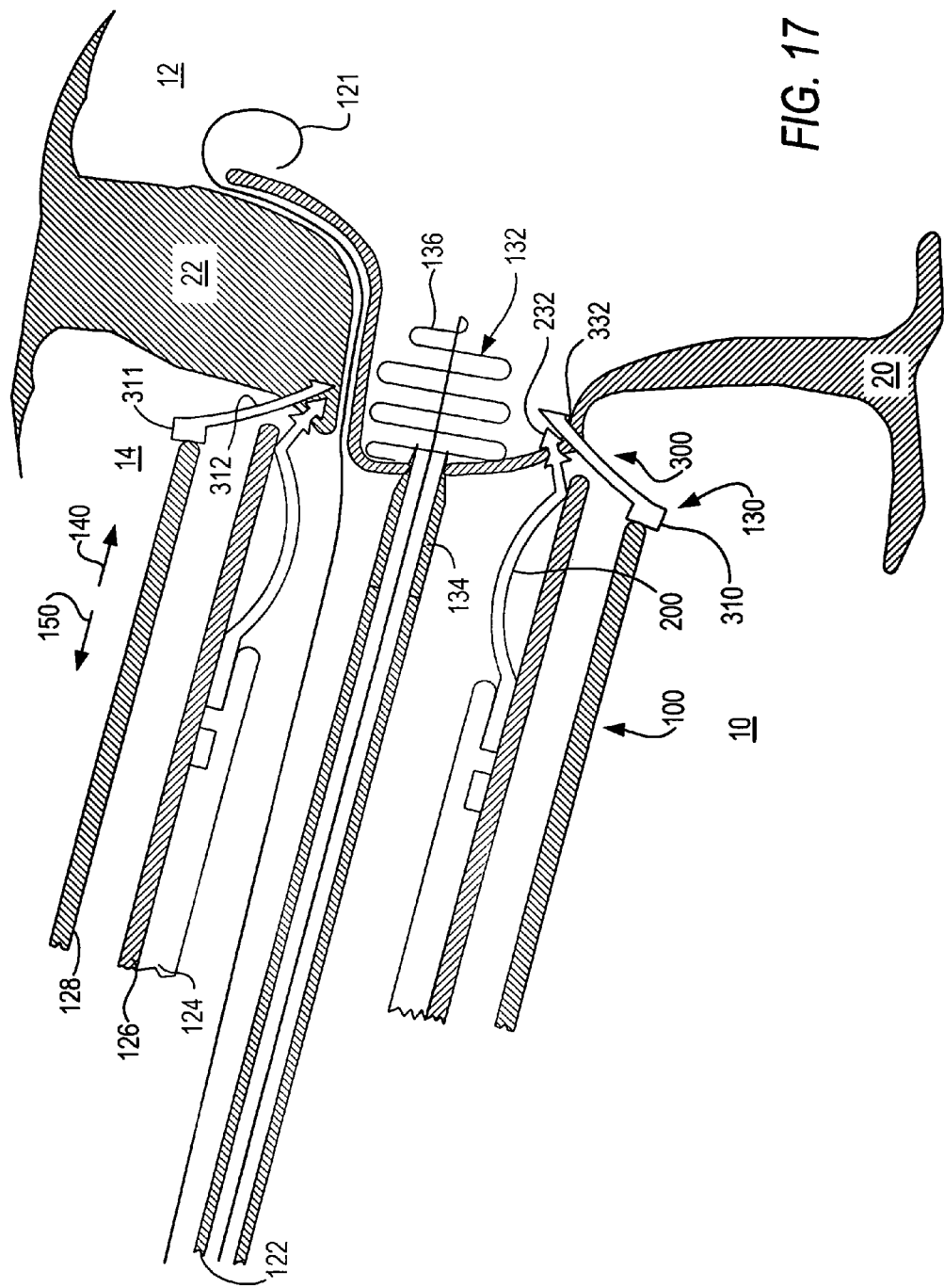

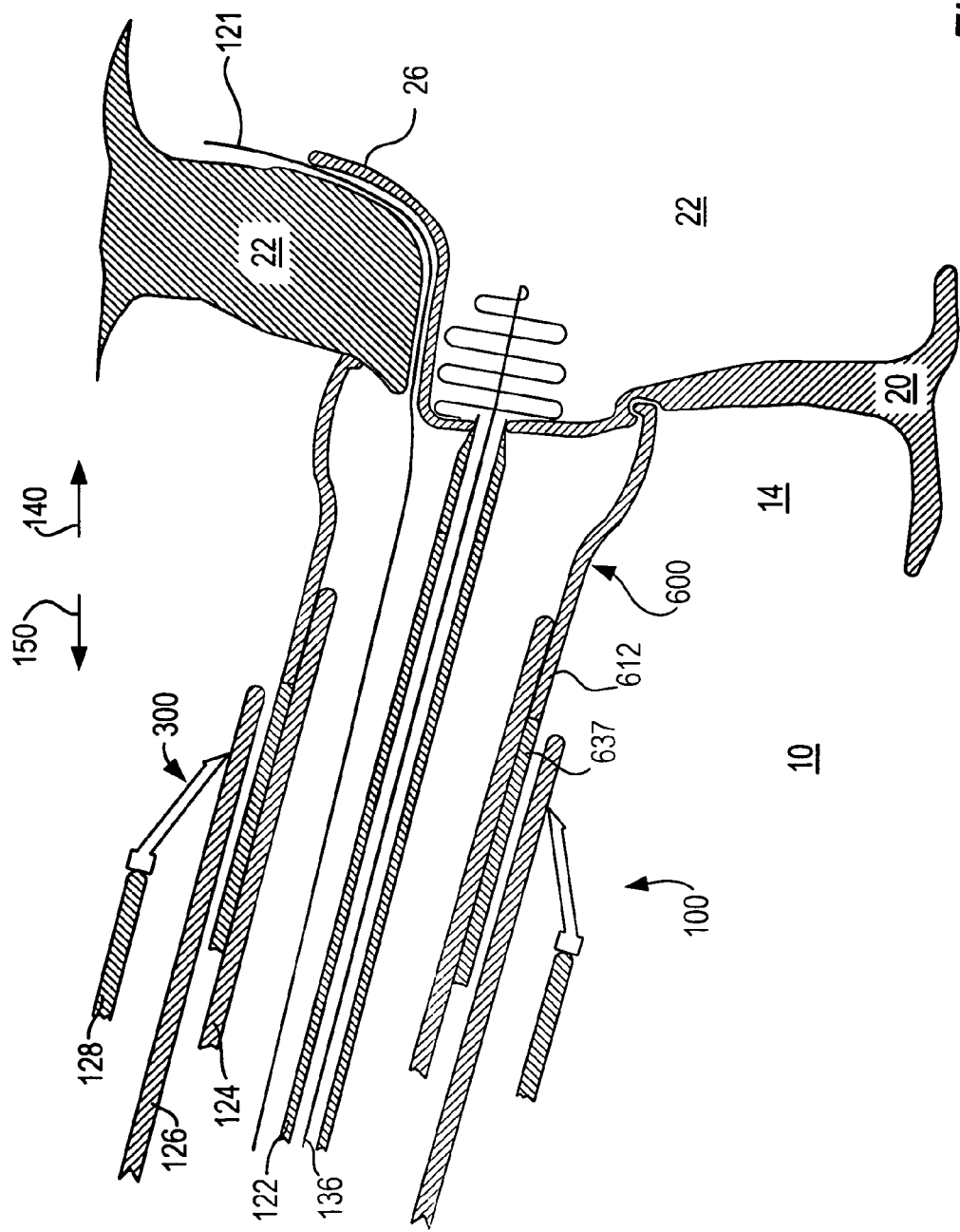

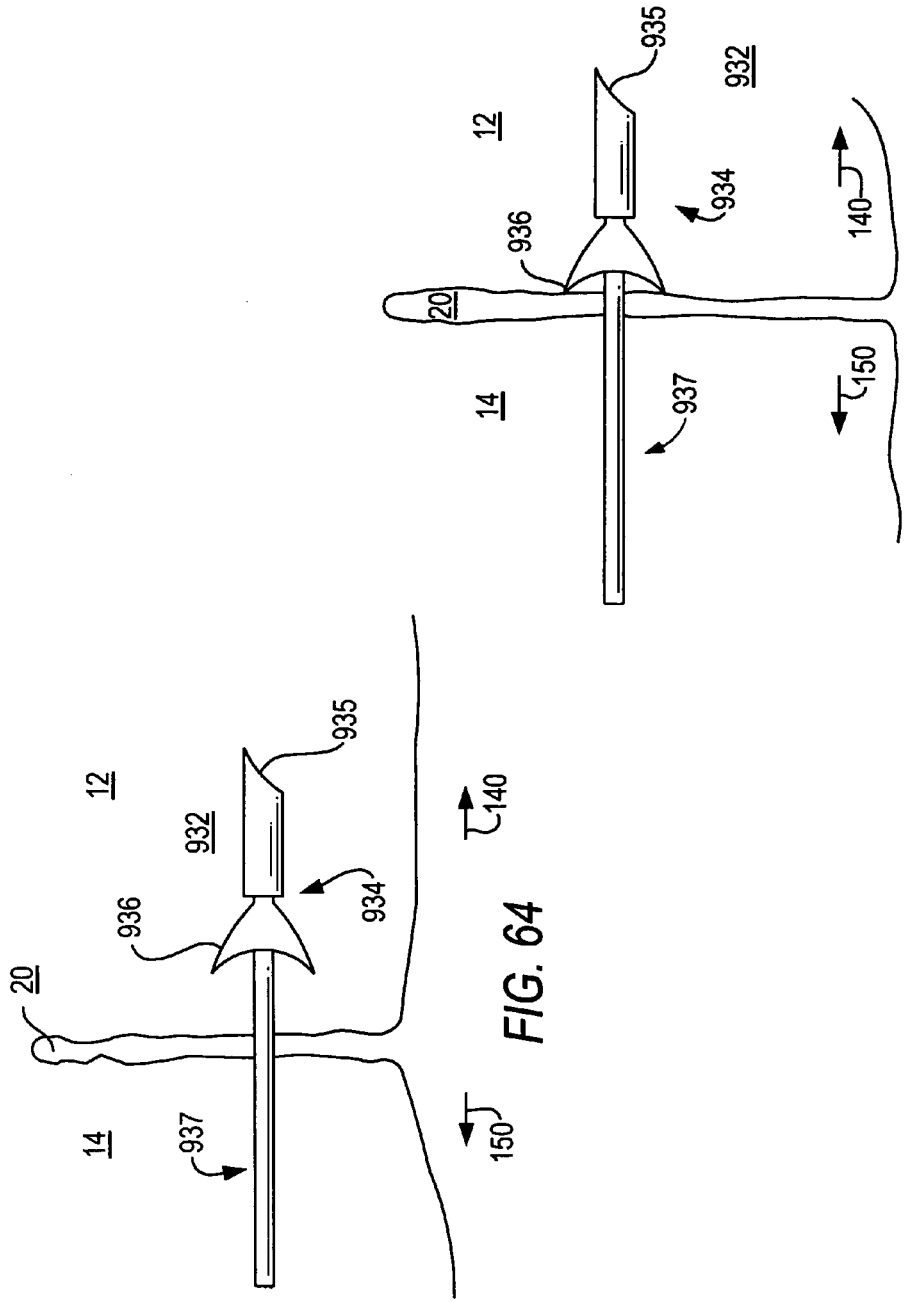

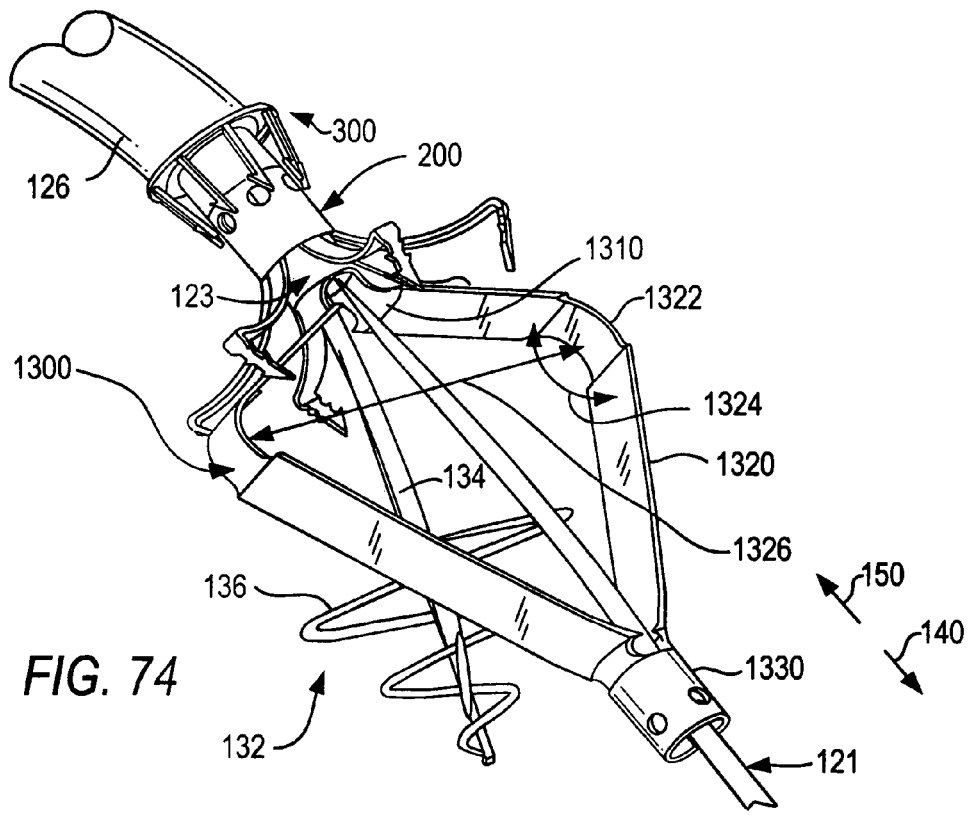
FIG. 74
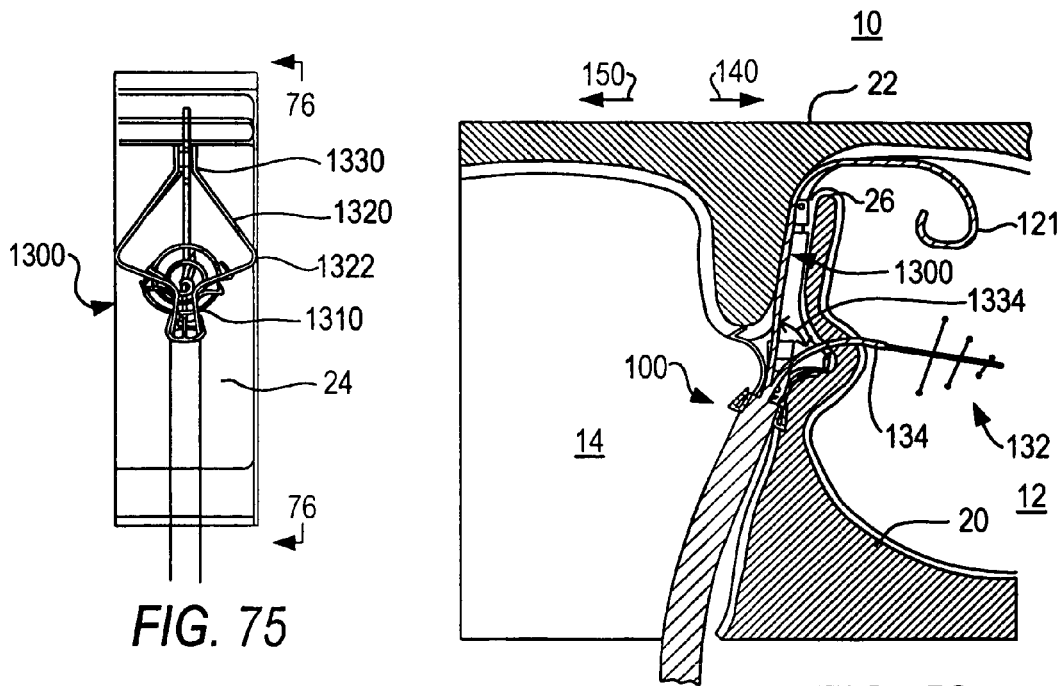
FIG. 75
FIG. 76

APPARATUS AND METHODS FOR TISSUE GATHERING AND SECURING

This application claims the benefit of U.S. provisional patent application No. 60/504,320, filed Sep. 19, 2003, U.S. provisional patent application No. 60/506,345, filed Sep. 25, 2003, U.S. provisional patent application No. 60/506,348, filed Sep. 25, 2003, U.S. provisional patent application No. 60/515,870, filed Oct. 29, 2003, and U.S. provisional patent application No. 60/585,366, filed Jul. 2, 2004. Each of these prior applications is hereby incorporated by reference herein in its entirety.

BACKGROUND OF THE INVENTION

The present invention relates to medical apparatus and methods for gathering and securing tissue in a reduced area in a patient's body, and, more particularly, to apparatus and methods for utilizing the tissue about a septal defect found between the walls of the four heart chambers, such as patent foramen ovale ("PFO"), to obstruct or close the defect itself that minimize or eliminate foreign material in the left atrium of a patient with minimal structure that is proportional to the size of the defect.

The heart includes left and right atrial chambers in the upper portion and left and right ventricular chambers in the lower portion. Defects in these walls can be formed congenitally or can develop later in life. An atrial septal defect ("ASD") is found between the right and left atriums and a ventricular septal defect ("VSD") is found between the left and right ventricles. These defects allow blood to be shunted between the chambers, causing the heart's pumping action to be inefficient, and creating a risk of embolization (the circulation of an abnormal particle through the bloodstream).

A similar defect is the patent ductus, which is a pre-birth opening between the aorta and the pulmonary artery. This opening usually closes naturally, but may remain open and cause oxygenated blood to flow back into the lungs.

Other defects are the ductus arteriosis and the patent foramen ovale. The PFO is a valved lumen found in the septal wall tissue (i.e., the septum primum and the septum secundum) between the left and right atriums. While this lumen is present at birth, it typically closes naturally. However, this lumen may stay patent.

Patent foramen ovale is a flap-like opening between the atrial septa primum and secundum at the location of the fossa ovalis that persists after the age of one year. Until birth, normal fetal circulation requires blood to mostly bypass the lungs and be shunted through a foramen ovale located between the right atrium and the left atrium. After birth, normal circulation routes most of the blood to the lungs and this physiologic shunt closes. In a normal prenatal heart, the septum secundum and the septum primum fuse longitudinally and grow peripherally towards the center, forming a valve which channels the blood from the right atrium to the left atrium. After birth, the flap, or tip of the septum primum is pushed against the cranial part of the septum secundum, and they fuse within weeks. Sometimes, however, this fusion fails to occur, resulting in a PFO. Various publications and autopsy studies have shown a prevalence of probe patent foramen ovale of about 30%.

The anatomy of a PFO is a flap in the septal wall between the left and right atriums. It is important to note that this defect, unlike an atrial septal defect (ASD) or a ventricular septal defect (VSD), is a flap or tunnel and not a hole. The flap or tunnel primarily consists of the septum primum on the left side of the caudal portion of the interatrial septum. Clinical autopsy studies and publications have also revealed an average size of a patent foramen ovale to be about 6.0 millimeters in diameter.

The PFO flap acts as a one-way valve in that the right atrium pressure must be greater than the left atrium pressure in order for the flap to open. When open, the PFO flap provides a passageway for blood to be shunted from the right atrium directly into the left atrium. With increasing evidence that patent foramen ovale is the culprit in paradoxical embolic events, the relative importance of the anomaly is being reevaluated. It has been postulated that patent foramen ovale anatomy results in a cul-de-sac between the septa primum and secundum, predisposing individuals to hemostasis and clot formation. Any conditions that increase right atrial pressure more than left atrial pressure can induce paradoxical flow and may result in an embolic event. Normally, the pressure in the left atrium is higher than in the right atrium, which keeps the flap or tunnel shut. However, under certain physical exertion, such as lifting or coughing, a "valsalva" effect is achieved. Valsalva is a condition when right atrium pressure is higher than left atrium pressure, allowing the PFO flap or tunnel to open and blood to shunt between the atria. This right to left shunting allows blood to bypass the natural blood filtering function of the lungs. Given the critical lung function of filtering blood clots or emboli from the blood, patients with a PFO are at high risk for shunting emboli from the venous to the arterial side of the circulatory system. As a result, the risk of stroke is greatly increased in these patients. This reasoning has greatly altered the previous conception of patent foramen ovale and is changing current management of the condition.

Therefore, it would be desirable to provide minimally-invasive and reliable apparatus and methods for treating septal defects, such as PFO, that provide acute closure, that minimize or eliminate foreign material in the left atrium of a patient, with minimal structure that is proportional to the size of the defect, and that minimize the amount of manipulation in the left atrium.

It would also be desirable to provide reliable apparatus and methods for delivery of minimally invasive, percutaneous, intraluminal transcatheters and deployment of septal defect devices.

It would be further desirable to provide septal defect devices that can be properly matched to the anatomy and motion of the defect area.

SUMMARY OF THE INVENTION

It is therefore an object of the invention to provide apparatus and methods for gathering and securing tissue in a reduced area in a patient's body. In accordance with one aspect of the present invention, apparatus and methods are provided that gather the tissue about a septal defect found between the walls of the four heart chambers, such as, but not limited to ASD, VSD, PAD, and PFO, to obstruct or close the defect itself immediately, and that then secure the tissue in that position or configuration with some minimal securing structure. Preferably, the securing structure mainly resides on one side of the defect to minimize or eliminate foreign material and the amount of manipulation or activity in the left atrium of the patient.

The methods and apparatus of this invention may be used to reliably close a patent foramen ovale lumen from the right atrium with minimal to no access to, or foreign material in, the left atrium. A method is provided for closing a patent foramen ovale that may comprise advancing a catheter in the right atrium to the PFO lumen, deploying a tissue positioning device at the defect, securing together the tissue about the defect, detaching the catheter from the securing device, removing the catheter, and leaving behind a minimal securing structure that completely closes the patent foramen ovale lumen from the right side and leaves little or no material in the left atrium.

Preferably, the method utilizes the tissue of the lumen walls in such a way that it closes the lumen. For example, a method of the present invention may include prolapsing septum primum tissue onto septum secundum tissue and/or effectively collapsing or gathering septum primum and septum secundum tissue together, such that opposing sides of the lumen come in contact with each other and effectively reduce the lumen area to nothing, thereby effectively closing the lumen to seal or close a patent foremen ovale, or any other comparable anatomy. This method appositions the tissue such that an area of tissue is gathered into a smaller or reduced area and held therein. Preferably, tissue circumferentially about the ostium or lumen from both atrial sides thereof should be included in this apposition. The effect of reducing the area or gathering the tissue from both the septum primum and septum secundum effectively closes the lumen directly and/or stretches it tight to provide tension that appositions the lumen closed, such that the lumen can not be opened under physiological pressure.

It is also an object of the invention to provide reliable apparatus and methods for delivery of intraluminal transcatheters and deployment of septal defect devices.

It is a further object of the invention to provide septal defect devices that can be properly matched to the cardiac cavity and its motion to promote healing and long term implant compatibility.

BRIEF DESCRIPTION OF THE DRAWINGS

The above and other advantages of the invention will be more apparent upon consideration of the following detailed description, taken in conjunction with the accompanying drawings, in which like reference characters refer to like parts throughout, and in which:

FIG. 3 is a planar development of the structure of the gathering device of FIG. 2;

FIG. 17 is a cross-sectional view of the heart, gathering device, retaining device, and apparatus of FIGS. 13-16, in a fifth stage of a procedure, in accordance with the present invention;

FIG. 48 is a cross-sectional view of a portion of the heart of FIG. 1, illustrated with the retaining device and apparatus of FIGS. 11-17, but in conjunction with the gathering device of FIGS. 46 and 47, in the fifth stage of a procedure of FIG. 17, in accordance with the present invention;

FIG. 64 is a cross-sectional view of a portion of the heart of FIG. 1, illustrated with yet another illustrative embodiment of an apposition mechanism, in a first stage of a procedure, constructed in accordance with the present invention;

FIG. 65 is a cross-sectional view of the heart and apposition mechanism of FIG. 64, in a second stage of a procedure, in accordance with the present invention;

FIG. 74 is a perspective view of the gathering device, retaining device, and apparatus of FIGS. 11-17, but in conjunction with a guide wire mechanism, in an expanded configuration, constructed in accordance with the present invention;

FIG. 75 is a partially sectional view of a portion of the heart of FIG. 1, illustrated with the gathering device, retaining device, apparatus, and guide wire mechanism of FIG. 74, in a first stage of a procedure, in accordance with the present invention;

FIG. 76 is a cross-sectional view of the heart, gathering device, retaining device, apparatus, and guide wire mechanism of FIG. 75, taken from line 76-76 of FIG. 75;

DETAILED DESCRIPTION OF THE PREFERRED EMBODIMENTS

The present invention provides apparatus and methods for gathering and securing tissue in a reduced area in a patient's body, and, more particularly, to apparatus and methods for utilizing the tissue about an opening in a wall or a lumen to obstruct or close the opening or lumen itself. Although the provided apparatus and methods can be used in a variety of types of body tissues, for simplicity the invention will be fully understood from the following explanation of its use in closing a patent foramen ovale in a patient's heart.

Figure 1:
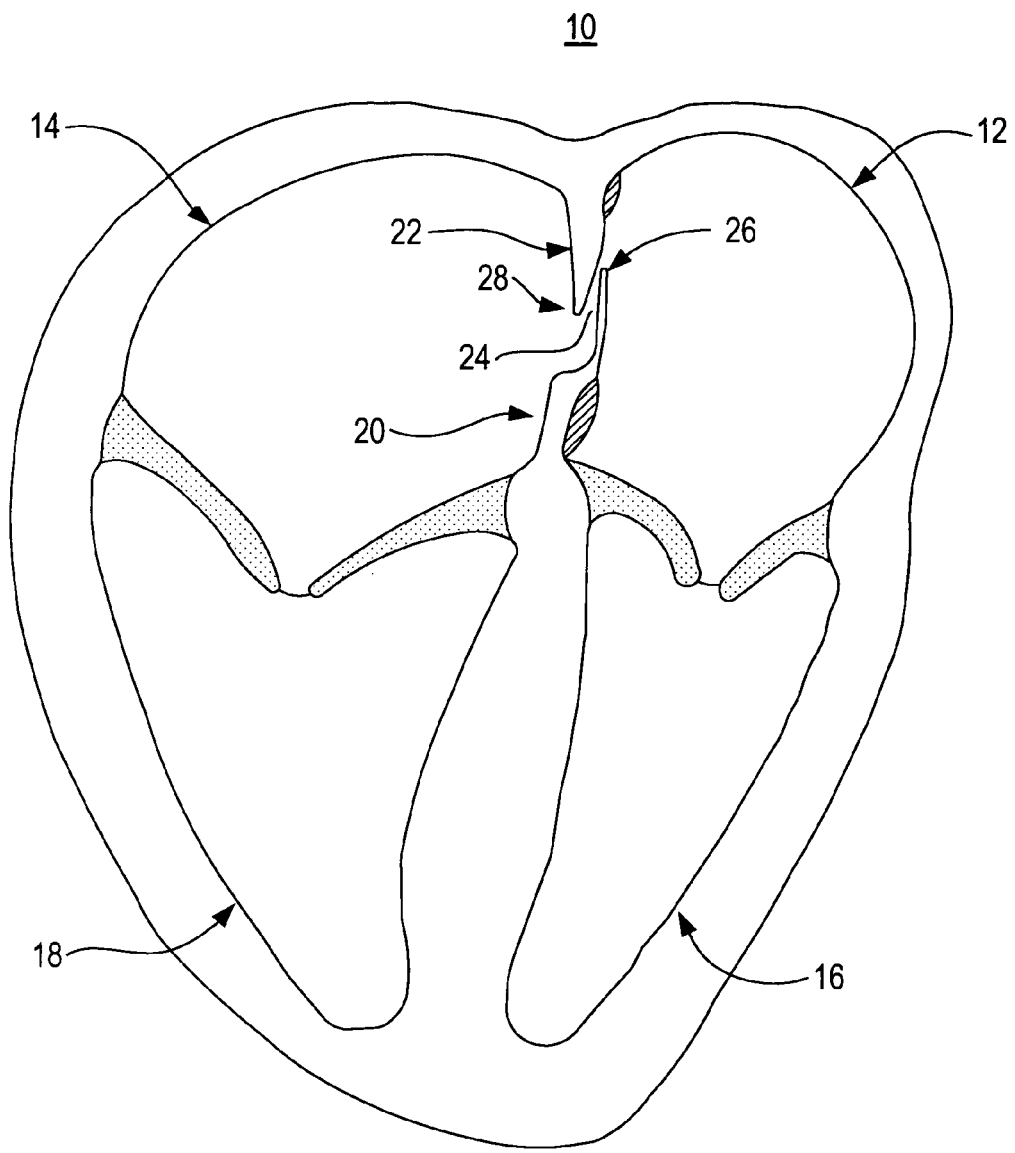
FIG. 1 is a prior art cross-sectional view of a heart.

FIG. 1 shows the four chambers of a heart 10 with a PFO. The upper portion of heart 10 includes left atrial chamber or atrium 12 and right atrial chamber or atrium 14, while the lower portion includes left ventricular chamber or ventricle 16 and right ventricular chamber or ventricle 18. As shown, left atrium 12 and right atrium 14 are partitioned by atrial septum primum 20 and atrial septum secundum 22. Heart 10 is shown having patent foramen ovale 24, a flap-like opening or lumen running between tip 26 of septum primum 20 and leading edge or limbus area 28 of septum secundum 22.

In accordance with the present invention, apparatus and methods are provided for reliably closing or ligating a lumen in the body, such as a patent foramen ovale lumen (e.g., PFO 24). The method involves utilizing the structure of the tissue itself in such a way that the lumen is positioned to collapse upon itself, thereby closing or ligating itself for preventing flow therethrough. This may be accomplished by bringing the tissue from all sides of (or from completely around the circumference of) the lumen together into a reduced or concentrated area and by securing the tissue in that collapsed or condensed position. Moreover, this can be accomplished, significantly, from only one side of the lumen that is to be closed.

Figure 1A:
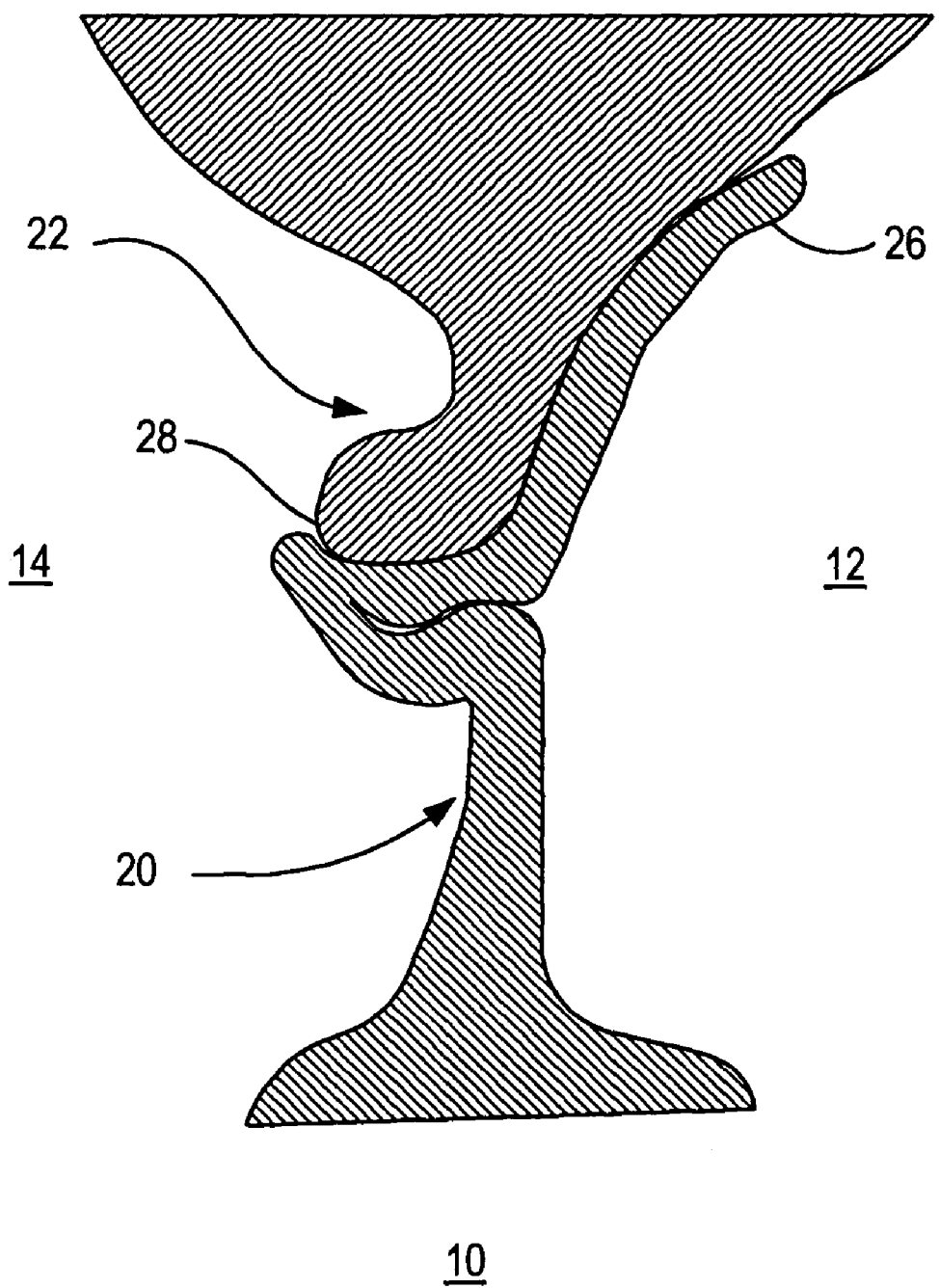
FIG. 1A is a cross-sectional view similar to FIG. 1 of a portion of the heart of FIG. 1 gathered into a reduced area in accordance with the present invention.

The gathering of the tissue can be such that the tissue that is more malleable, moveable, or manipulatable can be substantially utilized to close the lumen. In regards to the anatomy of a PFO (e.g., PFO 24), the tissue of septum primum 20 is thinner and more pliable than that of septum secundum 22. Therefore, the tissue of septum primum 20 can be stretched, collapsed, prolapsed, or gathered onto or with the tissue of septum secundum 22 (preferably, limbus area 28) in a manner effectively closing the lumen of the tunnel that is the PFO. This arrangement of tissue for effectively closing the lumen of a PFO is shown, for example, in FIG. 1A by the tissue of septum primum 20 and septum secundum 22 of PFO 24 of heart 10.

In such a case as PFO 24, the lumen can be closed substantially from right atrium 14 with minimal or no manipulation within left atrium 12, and with minimal or no foreign material left in the left atrium. The present invention may preferably involve advancing a minimally invasive, percutaneous intraluminal transcatheter apparatus in right atrium 14 to the PFO lumen, deploying a tissue gathering device through the catheter apparatus for promoting apposition of the tissue of septum primum 20 and septum secundum 22 circumferentially about the lumen from both atrial sides thereof, securing the tissue in its gathered position with a retaining device in right atrium 14, and removing the catheter apparatus and gathering device from the right atrium, while leaving behind the minimal structure of the retaining device. As shown, for example, in FIGS. 1B-1D, the structure of a retaining device of the present invention (e.g., exemplary retaining device 300, described in greater detail hereinbelow) completely closes the patent foramen ovale lumen utilizing the tissue about the lumen from the right side and, preferably, leaves no structure material in left atrium 12.

Figure 2:
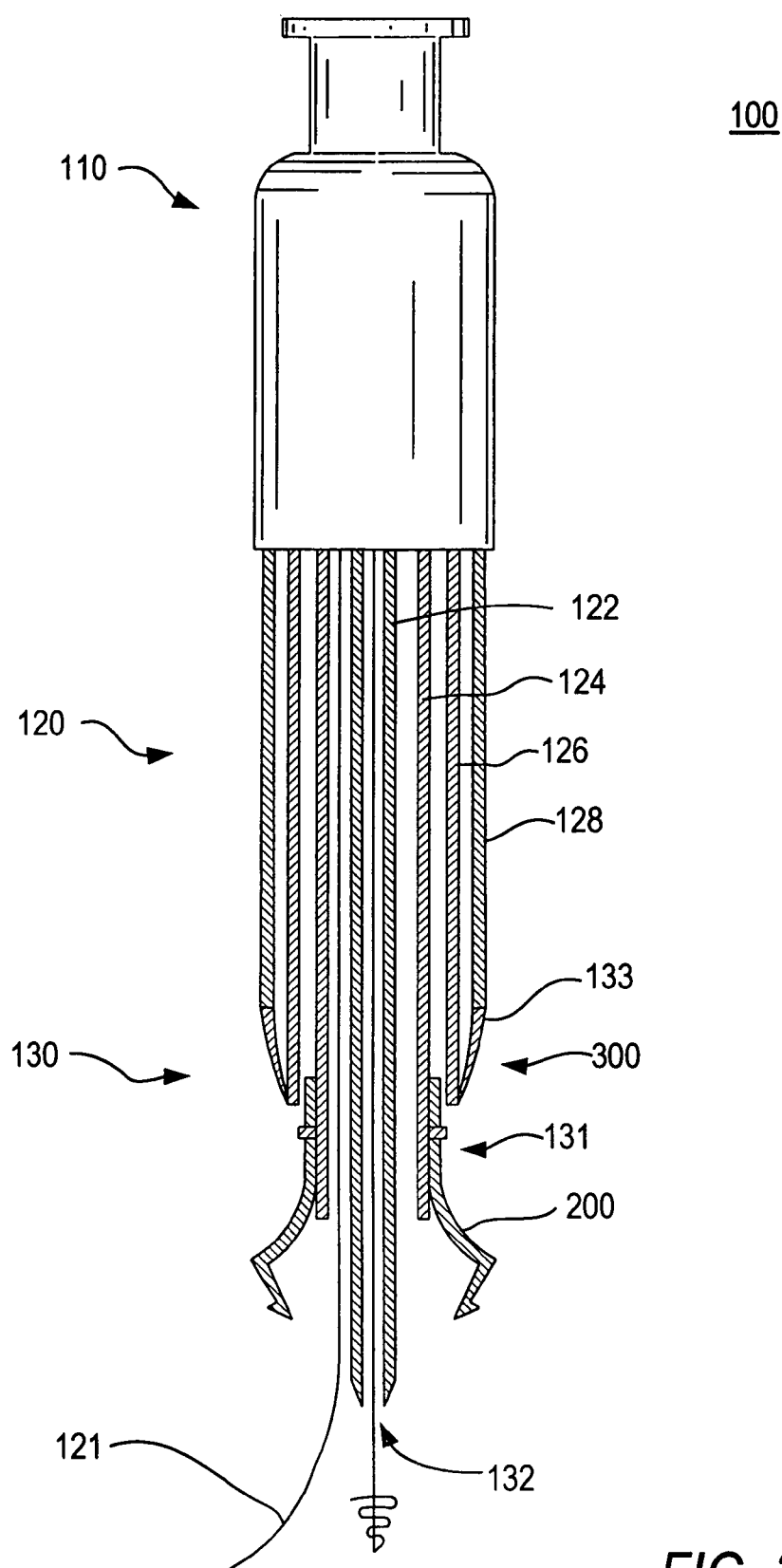
FIG. 2 is a simplified, partially sectional view of an illustrative embodiment of an apparatus with an illustrative embodiment of an apposition mechanism constructed in accordance with the present invention, illustrated with the retaining device of FIGS. 1B-1D and an illustrative embodiment of a gathering device in accordance with the present invention.
Figure 88:
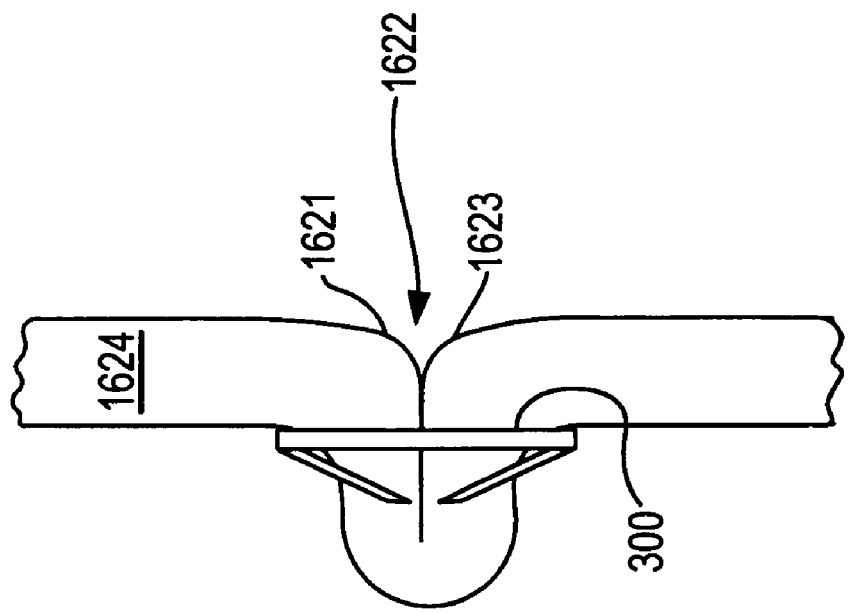
FIG. 88 is a cross-sectional view, similar to FIG. 87, of a gathered portion of the wall of FIG. 87 secured by the retaining device of FIGS. 7-12A, in accordance with the present invention.

A number of embodiments according to the present invention, with several variations, are shown in FIGS. 2-88.

A preferred embodiment of apparatus for providing minimally invasive, percutaneous delivery and deployment of devices in accordance with the present invention is illustrated in FIG. 2, and designated with the number 100. Apparatus 100 may include a proximal handle portion 110 with one or more actuation devices, an elongated medial portion 120, and a distal portion 130. According to a preferred embodiment, apparatus 100 has been illustrated as a single, integrated instrument. As will be described in greater detail herein, it is also contemplated that the various functions and/or the various components may be separated into a plurality of separate instruments that may provide minimally invasive percutaneous delivery and deployment of devices in accordance with the present invention.

Medial portion 120 of apparatus 100 may be an intraluminal transcatheter assembly including a series of concentric cylindrical tubes or support members (e.g., members 122, 124, 126, and 128) that may be introduced through peripheral venous access. Each of the concentric cylindrical tubes may be fabricated with sufficient length to allow the physician to treat the patient's defect by actuating distal portion 130 of apparatus 100 from a distance away using one or more of the actuation devices (not shown) of proximal handle portion 110. According to the present invention, a guide wire 121 may also be provided, if desired, to help facilitate locating the site of the defect to be closed, as will be described in greater detail hereinbelow.

Distal portion 130 of apparatus 100 performs a plurality of functions in the closure of the PFO. For example, distal portion 130 may include a transeptal apposition mechanism (e.g., mechanism 132) that may pass through the septum primum from the right atrium to the left atrium for locating and/or securing the left atrial side of the PFO to provide positive apposition on the septum primum toward the right atrium and the septum secundum. Distal portion 130 may also include a gathering mechanism 131 for selectively deploying a gathering device (e.g., device 200), which may first expand to engage the septum primum and septum secundum tissue in the right atrium that is preferably being apposed by apposition mechanism 132 in the left atrium, and then may contract to gather and hold the tissue in a reduced area. Furthermore, distal portion 130 may also include a retaining mechanism 133 for selectively deploying a retaining device (e.g., device 300), which may pass over and beyond gathering device 200 to secure the tissue gathered from both the septum primum and septum secundum.

When apparatus 100 is utilized to close a patient's defect, the physician may perform the following preferred sequence of steps. To prepare for the procedure, each of gathering device 200 and retaining device 300 is attached to distal end portion 130 of apparatus 100. Then, guide wire 121 is passed from the right atrium, through the lumen of the PFO, and into the left atrium to allow precise tracking of the gathering device and the retaining device into the patient's heart. Alternatively guide wire 121 may be omitted. Next, transeptal apposition mechanism 132 preferably punctures and passes through the tissue of the septum primum from the right atrium and into the left atrium to provide positive apposition on the septal wall from the left atrial side of the PFO. Then, gathering mechanism 131 selectively deploys gathering device 200, which apposes tissue from both the septum primum and septum secundum and holds the gathered tissue in a reduced area. Finally, retaining mechanism 133 selectively deploys retaining device 300, which secures the tissue gathered by gathering device 200 to complete the closure of the PFO. Each of the components and steps will be described in greater detail hereinbelow.

Figure 5:
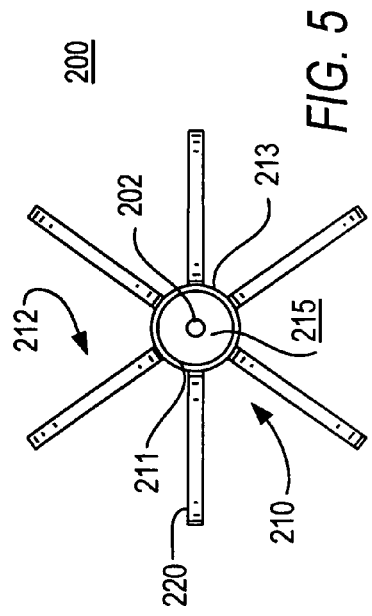
FIG. 5 is a top elevational view of the gathering device of FIGS. 2-4, taken from line 5-5 of FIG. 4.
Figure 6:
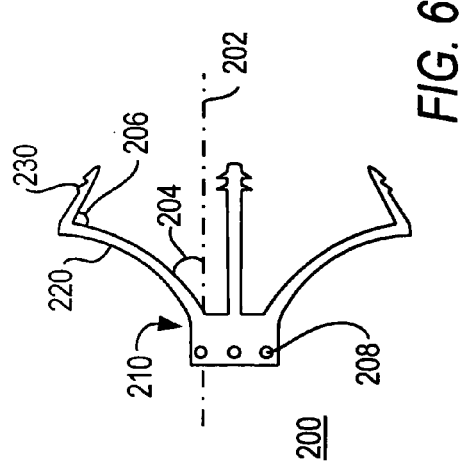
FIG. 6 is a side elevational view of the gathering device of FIGS. 2-5, taken from line 6-6 of FIG. 4.
Figure 4:
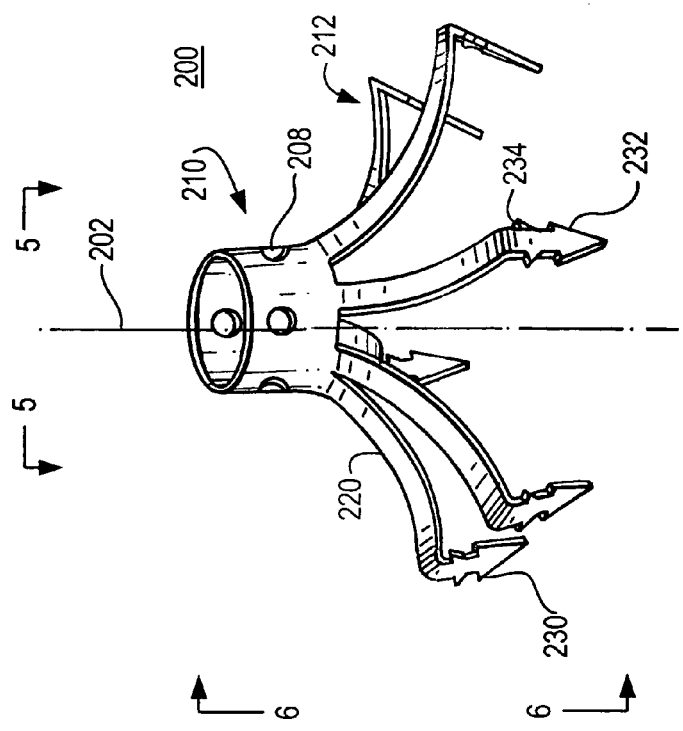
FIG. 4 is a perspective view of the gathering device of FIGS. 2 and 3, in an expanded configuration, in accordance with the present invention.

FIGS. 3-6 illustrate a preferred embodiment of the gathering device 200 according to the present invention. Gathering device 200 may include a plurality of fingers 212 to engage the tissue of the septum primum and the septum secundum about the PFO lumen and then to gather and hold the tissue together in a reduced area to effectively close the defect. FIG. 3 shows a planar development of what is actually, preferably, an integral, one-piece (unitary), annular, gathering device 200. In particular, the left and right edges of the structure shown in FIG. 3 are actually, preferably, joined to and integral with one another. Thus, the actual structure of gathering device 200 is as shown in FIGS. 4-6, although FIG. 3 is useful to more clearly reveal certain details of various features of gathering device 200. A central longitudinal axis 202, about which gathering device 200 is annular, is shown in FIGS. 4-6.

A particularly preferred material for gathering device 200 is nickel-titanium alloy (i.e., nitinol). Other examples of suitable materials are described hereinbelow. It should be noted that, depending on the material of the device, different techniques may be used to shape the structure of device 200 shown in FIG. 3 into approximately the fully expanded geometry of FIGS. 4-6 that gathering device 200 may assume.

Gathering device 200 may be described as including an annular element 210 and a plurality of annularly spaced tissue gathering fingers 212 extending distally therefrom. According to one embodiment, gathering device 200 includes six fingers 212. Gathering device 200 may have fewer or more than six of fingers 212, depending on the axial length and perimeter of the tube used to manufacture gathering device 200, the type of defect to be closed, and the size and shape of the particular defect. Alternatively, the structure of gathering device 200 may have different configurations of fingers and geometries.

Each gathering finger 212 preferably includes a medial extension member 220 and a distal member 230. Each distal member 230 may preferably include a distal tissue holding feature that in this case includes a barb-like free end portion 232 that is sharply pointed distally and that preferably has at least one barb 234 proximal to free end portion 232. Each barb 234 extends laterally out and proximally back from the associated free end portion 232 The dimensions of each medial member 220 and each distal member 230 of each finger 212 may be altered according to the type, size, and shape of the defect to be closed, and to the particular finger's orientation to the defect when deployed in the patient (e.g., whether the finger is to engage the septum primum, the septum secundum, or both). Annular element 210 defines the proximal portion 214 of gathering device 200, whereas medial extension members 220 and distal members 230 define the medial portion 216 and the distal portion 218 of gathering device 200, respectively. A plurality of receiving slots 208 may be provided along annular element 210 for receiving tab elements at the distal end of member 124, as will be described in greater detail hereinbelow.

As shown in this example (see also FIGS. 4-6), gathering device 200 preferably has a fixed cross-sectional area. Specifically, annular element 210 of proximal portion 214 is an annular structure having a fixed annular dimension, an outer surface 213, an inner surface 211, and an opening 215 defined therein, which may be round, oval, or any other substantially smooth shape. In another preferred embodiment, annular element 210 of gathering device 200 may be annularly expandable or enlargeable, as will be described in greater detail hereinbelow.

In the fully expanded configuration of gathering device 200 shown in FIGS. 4-6, the medial extension member 220 of each finger 212 may expand radially out from annular element 210 at an angle 204 to longitudinal axis 202. The distal member 230 of each finger 212 may be oriented with respect to medial extension member 220 at an angle 206. Like the dimensions of each medial member 220 and each distal member 230 of each finger 212, orientation angles 204 and 206 for each finger 212 may be altered according to the type, size, and shape of the defect to be closed and its surrounding tissue, and to the particular finger's orientation to the defect when deployed in the patient.

Figure 7:
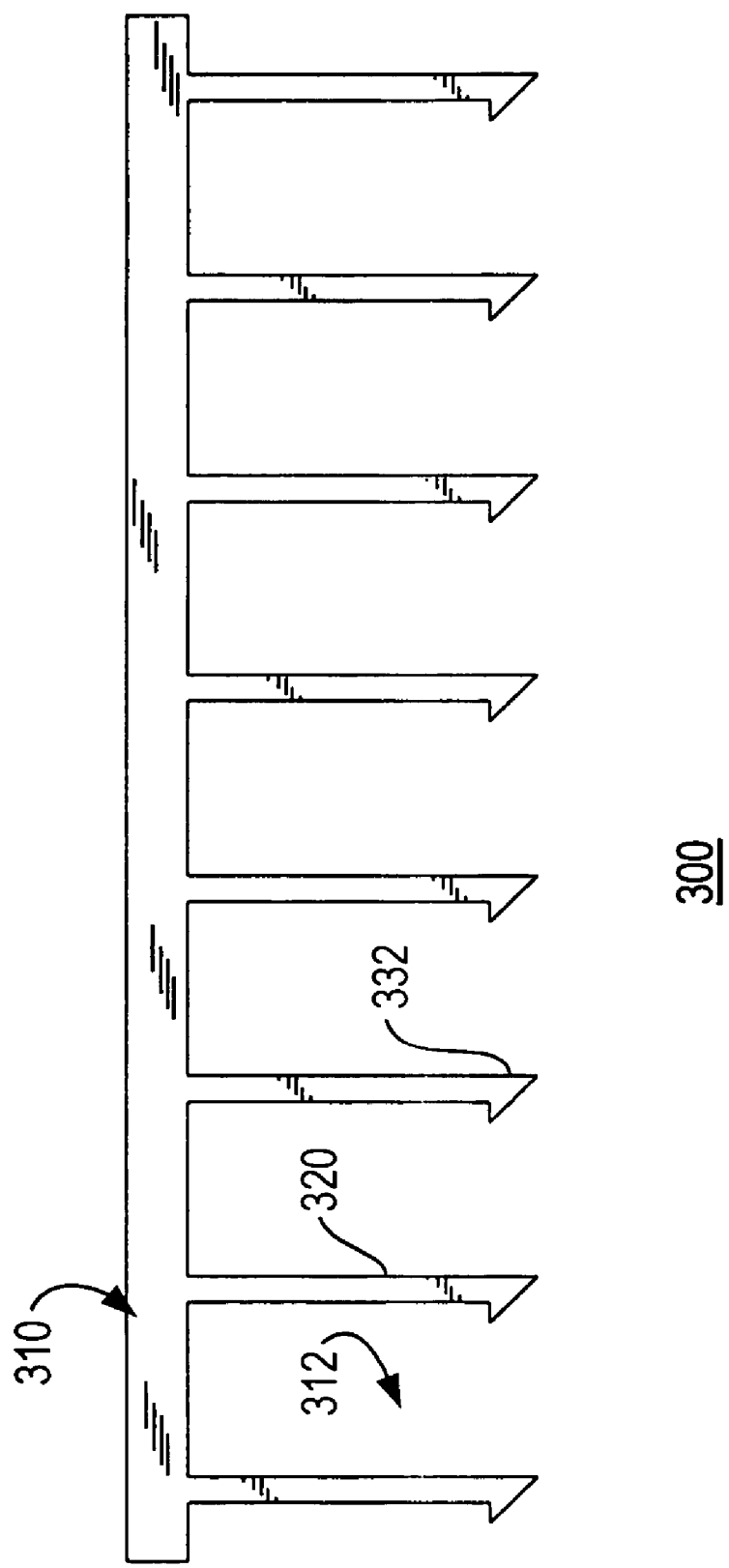
FIG. 7 is a planar development of the structure of the retaining device of FIGS. 1B-2.
Figure 8:
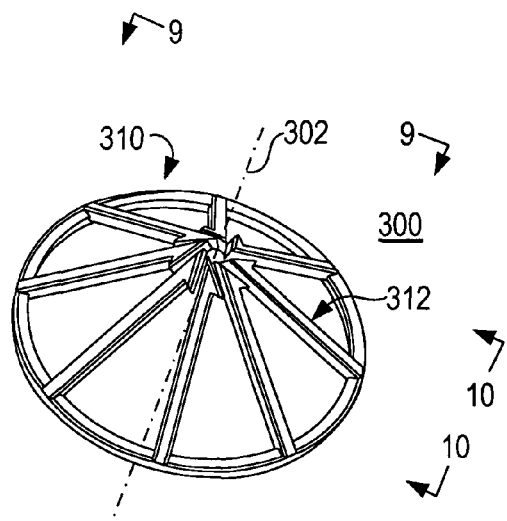
FIG. 8 is a perspective view of the retaining device of FIGS. 1B-2 and 7, in a functional configuration, in accordance with the present invention.
Figure 9:
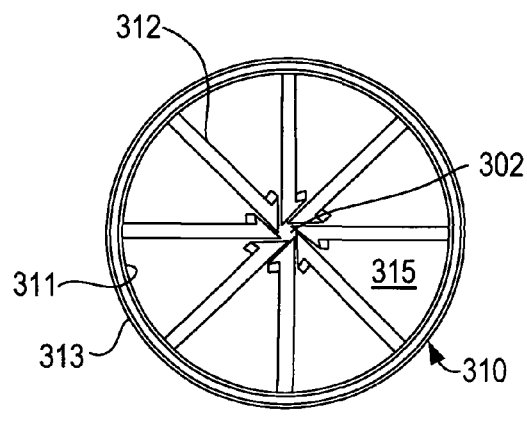
FIG. 9 is a top elevational view of the retaining device of FIGS. 1B-2, 7, and 8, taken from line 9-9 of FIG. 8.
Figure 10:
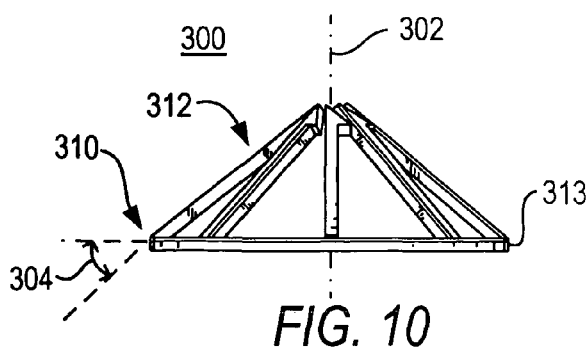
FIG. 10 is a side elevational view of the retaining device of FIGS. 1B-2 and 7-9, taken from line 10-10 of FIG. 8.

FIGS. 7-10 illustrate a preferred embodiment of the retaining device 300 according to the present invention. Retaining device 300 may include a plurality of fingers to engage and retain the tissue of the septum primum and the septum secundum about the PFO lumen gathered by gathering device 200. FIG. 7 shows a planar development of what is actually, preferably, an integral, one-piece (unitary), annular, retaining device 300. In particular, the left and right edges of the structure shown in FIG. 7 are actually, preferably, joined to and integral with one another. Thus, the actual structure of retaining device 300 is as shown in FIGS. 1B-1D, and 8-10, although FIG. 7 is useful to more clearly reveal certain details of various features of retaining device 300. A central longitudinal axis 302, about which retaining device 300 is annular, is shown in FIGS. 8-10.

Like gathering device 200, a particularly preferred material for retaining device 300 is nitinol. Other examples of suitable materials are described hereinbelow. It should be noted that, depending on the material of the device, different techniques may be used to shape the structure of device 300 shown in FIG. 7 into approximately the fully functional geometry of FIGS. 8-10 that retaining device 300 will assume after full deployment.

Retaining device 300 may be described as including an annular element 310 and a plurality of annularly spaced tissue retaining fingers 312 extending axially therefrom. According to one embodiment, retaining device 300 includes eight fingers 312. Retaining device 300 may have fewer or more than eight of fingers 312, depending on the axial length and perimeter of the tube used to manufacture retaining device 300, the type of defect to be closed, and the size and shape of the particular defect. Alternatively, the structure of retaining device 300 may have different configurations of fingers and geometries.

Each retaining finger 312 preferably includes a medial extension member 320 and a tissue retaining feature that in this case includes a barb-like free end portion 332 that is sharply pointed at the distal end and that includes a more proximal part that projects laterally out from the remainder of the associated finger 312. The dimensions of each medial member 320 and retaining feature may be altered according to the type, size, and shape of the defect to be closed and its surrounding tissue, and to the particular finger's orientation to the defect when deployed in the patient (e.g., whether the finger is to engage the septum primum, the septum secundum, or both).

As shown in this example (see also FIGS. 8-10), retaining device 300 preferably has a fixed cross-sectional area. Specifically, annular element 310 is an annular structure having a fixed annular dimension, an outer surface 313, an inner surface 311, and an opening 315 defined therein, which may be round, oval, or any other substantially smooth shape. In another preferred embodiment, annular element 310 of retaining device 300 may be annularly expandable or enlargeable, as will be described in greater detail hereinbelow.

In the fully functional configuration of retaining device 300 shown in FIGS. 8-10, the medial extension member 320 of each finger 312 may extend radially inwardly from annular element 310 at an angle 304 to the plane in which annular element 310 lies. Like the dimensions of each medial member 320 of each finger 312, orientation angle 304 may be altered according to the type, size, and shape of the defect to be closed and its surrounding tissue, and to the particular finger's orientation to the defect when deployed in the patient.

Figure 11:
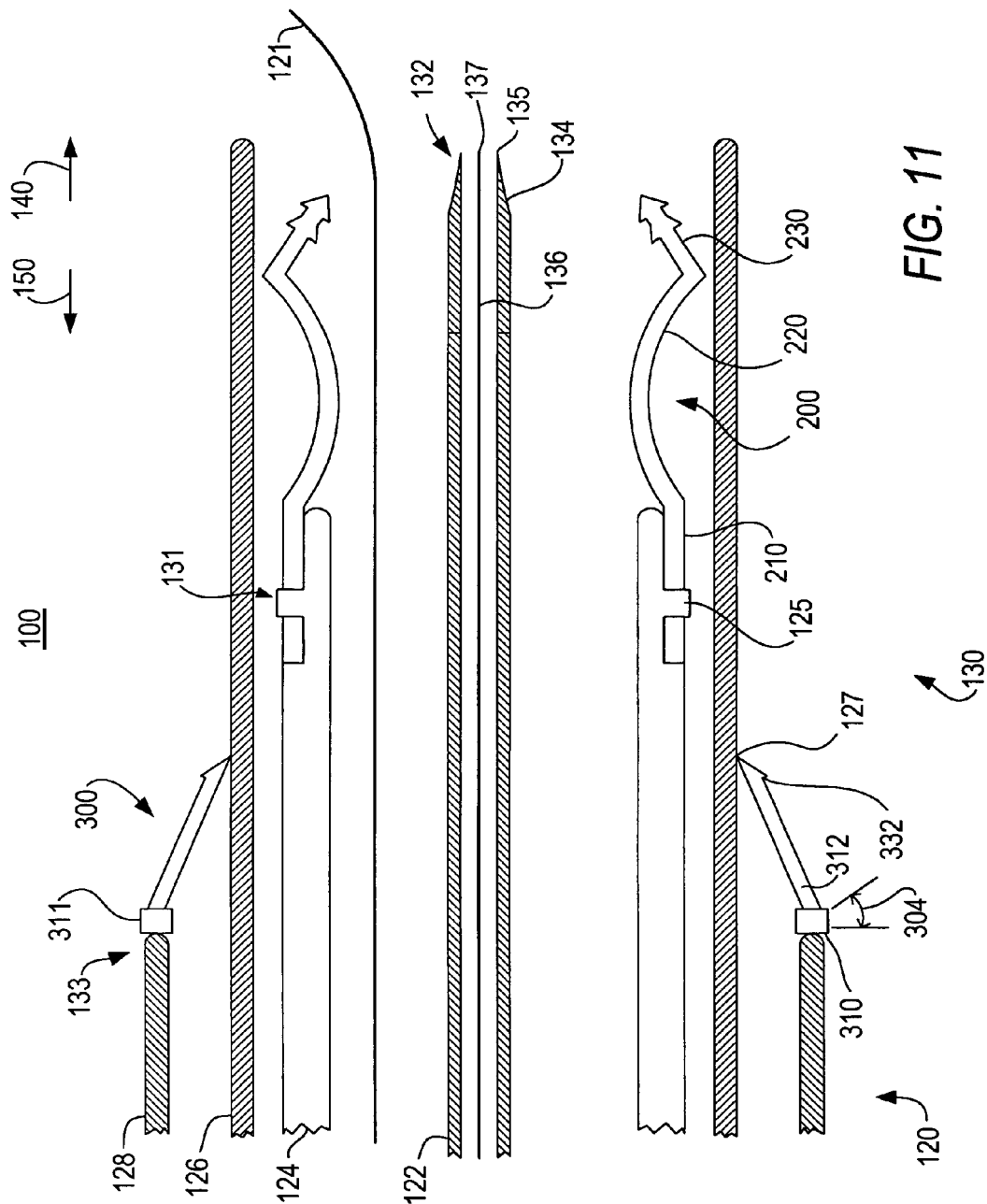
FIG. 11 is a cross-sectional view of the gathering device of FIGS. 2-6 and the retaining device of FIGS. 1B-2 and 7-10 mounted within a portion of the apparatus of FIG. 2, in an early stage of a procedure, in accordance with the present invention.
Figure 12:
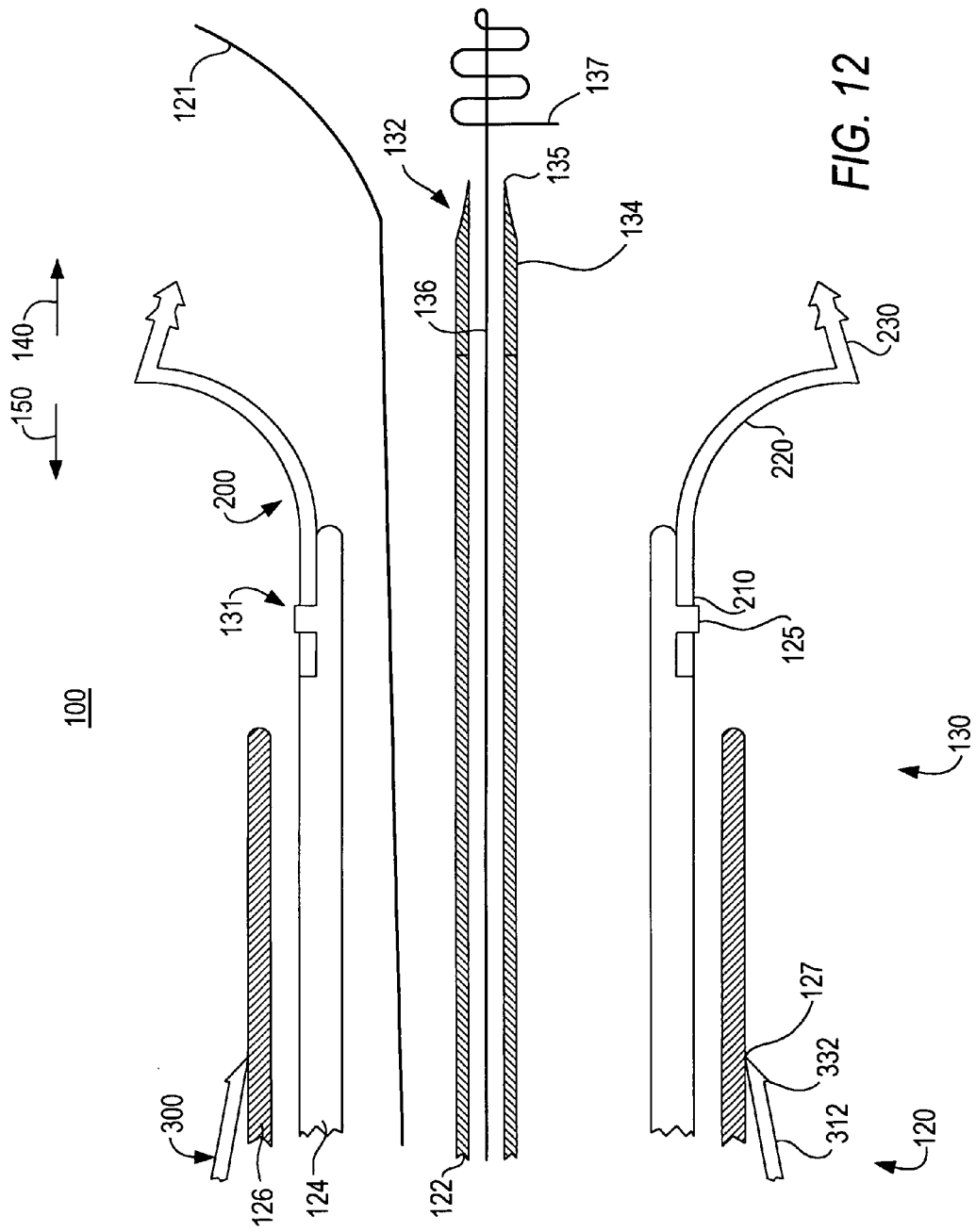
FIG. 12 is a cross-sectional view, similar to FIG. 11, of the gathering device, retaining device, and apparatus of FIG. 11, in a later stage of a procedure, in accordance with the present invention.
Figure 12A:
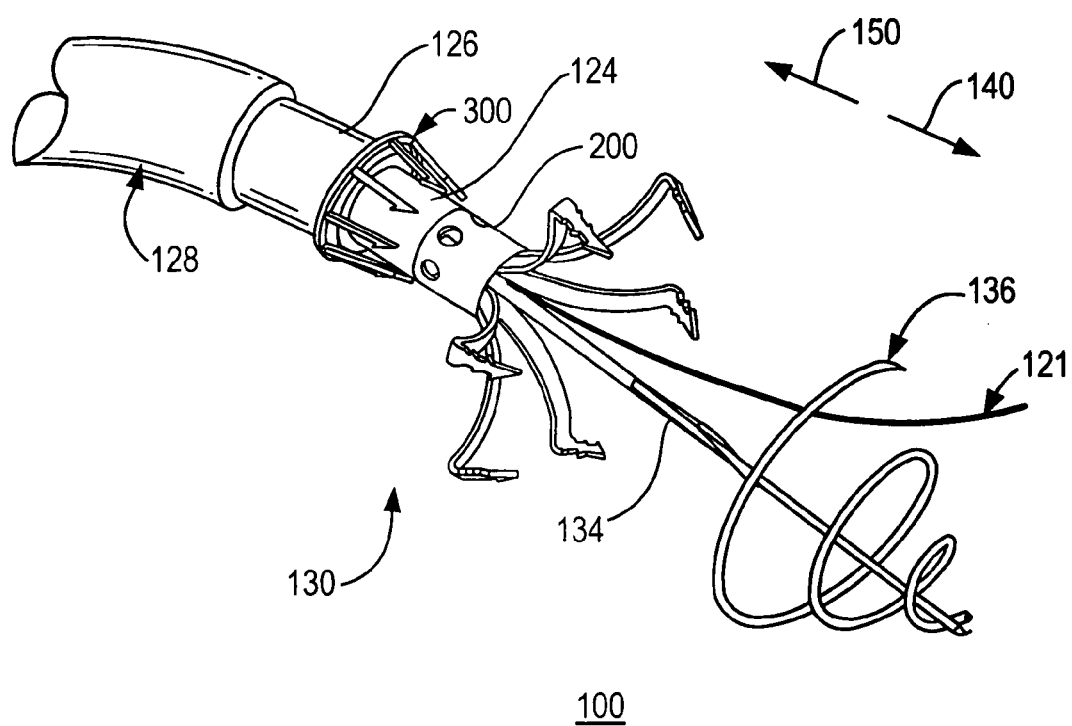
FIG. 12A is a perspective view of the gathering device, retaining device, and apparatus of FIGS. 11 and 12, in the later stage of a procedure of FIG. 12.

As shown in FIGS. 11-12A, an early step in the closure of a septal defect in a patient is the mounting of gathering device 200 and retaining device 300 to distal portion 130 of apparatus 100 in order to facilitate advancement and deployment of the devices by a physician. More particularly, annular element 210 of gathering device 200 is preferably positioned annularly about inner connector support member 124. The distal end portion of inner connector support member 124 is preferably provided with a plurality of outwardly facing tabs 125. Annular element 210 is positioned about inner connector support member 124 such that receiving slots 208 interact with tabs 125 for retaining gathering device 200 in the position shown in FIGS. 11-12A with respect to support member 124.

In the fully functional configuration of retaining device 300 shown in FIGS. 8-10, the medial extension member 320 of each finger 312 may extend radially inwardly from annular element 310 at angle 304 to the plane in which element 310 lies. However, in the condition shown in FIGS. 11-12A, fingers 312 have been elastically inverted or "rolled in" through opening 315 of annular element 310 to point in the opposite direction from their original position for the mounting of retaining device 300 to distal portion 130 of apparatus 100 (also see, e.g., U.S. patent application Ser. No. 10/813,447, filed Mar. 29, 2004, which is hereby incorporated by reference herein in its entirety). Annular element 310 is also thereby inverted such that inner surface 311 now faces outwardly and outer surface 313 faces inwardly towards axis 302, as shown in FIGS. 11-12A. The resilient force exerted by fingers 312 and/or annular element 310 preferably provides the necessary friction for retaining device 300 to be positioned annularly about middle connector support member 126 at a point 127 along middle connector support member 126. In an alternative embodiment, mechanical interlocking mechanisms may be provided to maintain the position of device 300 about connector support member 126. Outer support member 128 may abut the proximal end of retaining device 300 at annular element 310 for assisting in deploying retaining device 300 in the patient, as will be described in greater detail hereinbelow.

FIGS. 11-12A also illustrate a preferred embodiment of the transeptal apposition mechanism 132 according to the present invention. Apposition mechanism 132 may include a distal piercing portion at the distal end of concentric cylindrical member 122, such as transeptal cannula needle 134, having a sharpened tip 135, for penetrating the septum primum and at least partially passing therethrough. Transeptal apposition mechanism 132 preferably also includes a pre-bent, preferably helically-shaped, resilient wire 136 running through the hollow of member 122. Distal end 137 of wire 136 is preferably made of memory-shaped metal such that, as it passes distally out of sharpened tip 135 of needle 134, it deflects proximally back towards tip 135, as shown in FIGS. 12 and 12A, to provide positive apposition force to the septum primum, as will be described in greater detail hereinbelow. While a "helical" shape is described in this preferred embodiment, it is to be understood that the distal end of wire 136 may take any form once it is passed through the distal end of needle 134, such that it would require more force to redeflect the wire and pull it back proximally through tip 135 of needle 134 than it would to provide positive apposition force to the septum primum. Therefore, the distal end of wire 136 may take any shape that provides a structure for resisting passage back proximally through the septum primum tissue without departing from the spirit and scope of the present invention.

Each one of support members 122, 124, 126, and 128, guide wire 121, and shaped wire 136 is preferably configured for independent longitudinal movement in the distal direction of arrow 140 and in the proximal direction of arrow 150 with respect to each other. However, two or more of the support members may be configured to articulate together with respect to other members if desired. Retraction of support member 126 in the proximal direction of arrow 150 with respect to support member 124 (or advancement of support member 124 in distal direction 140 relative to support member 126) allows gathering device 200 to resiliently deflect to reach its fully expanded configuration, as shown in FIGS. 12 and 12A, while advancement of support member 126 in the distal direction of arrow 140 with respect to support member 124 (or proximal retraction of support member 124 in direction 150 relative to support member 126) causes medial members 220 and distal members 230 of gathering device 200 to deflect elastically and resiliently inwardly and to be retained in its constricted configuration, as shown in FIG. 11.

Figure 13:
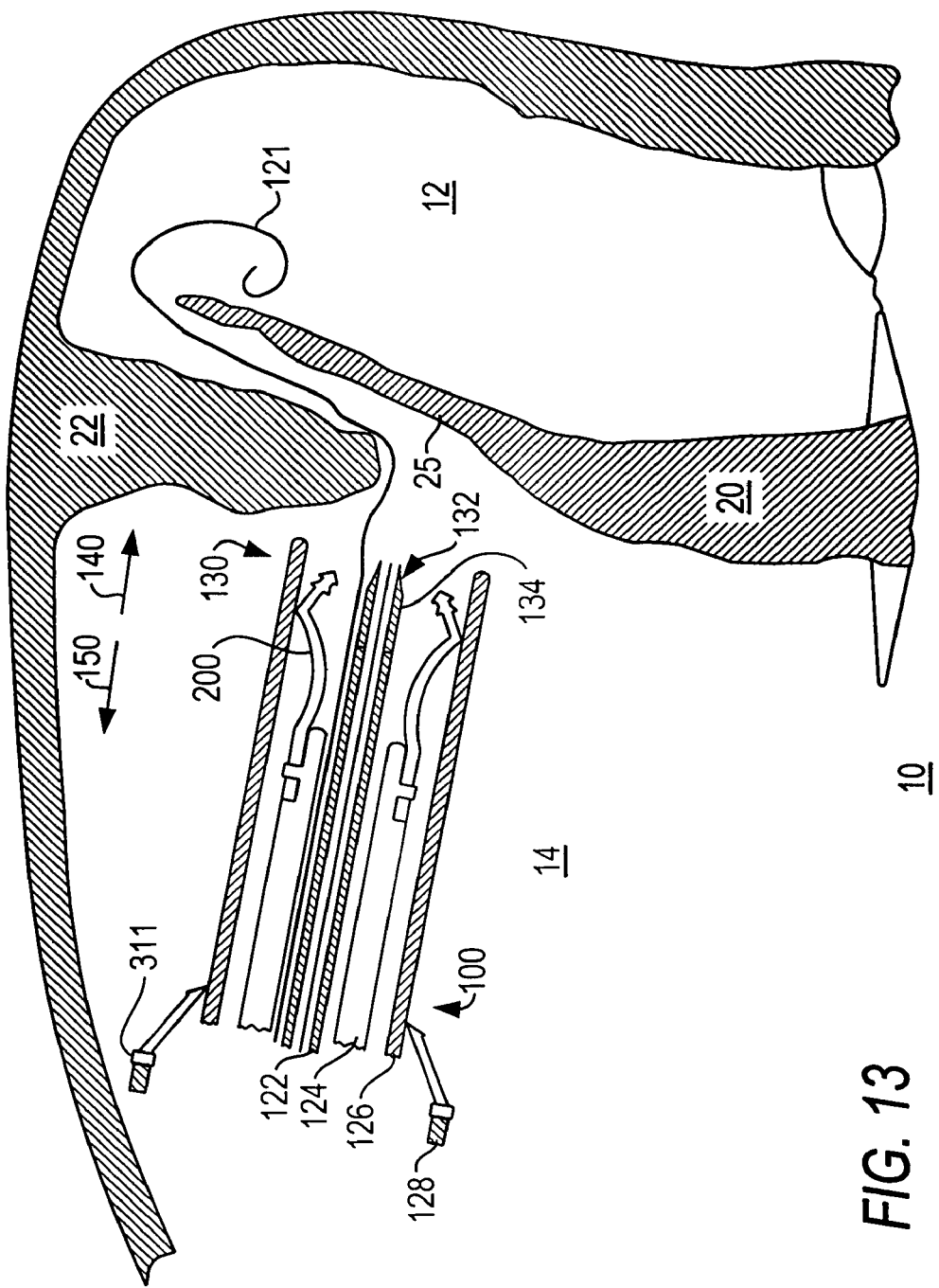
FIG. 13 is a cross-sectional view of a portion of the heart of FIG. 1, illustrated with the gathering device, retaining device, and apparatus of FIGS. 11-12A, in a first stage of a procedure, in accordance with the present invention.

FIG. 13 illustrates an early stage in the use of apparatus 100 for closure of a patient's PFO in accordance with the present invention. As illustrated in FIG. 13, the location of the operative site may be found by advancing guide wire 121 in the distal direction of arrow 140, through the right atrium 14 of the patient's heart 10, through PFO lumen 24, and into the left atrium 12. It should be understood that guide wire 121 is optional, and that the remaining steps may be similarly accomplished without the use of guide wire 121. However, if guide wire 121 is inserted into the patient prior to delivery of the rest of apparatus 100, the guide wire, which preferably runs concentrically within support members 124-128, can be used to guide gathering device 200 and retaining device 300 into place at the site of the septal defect.

Figure 14:
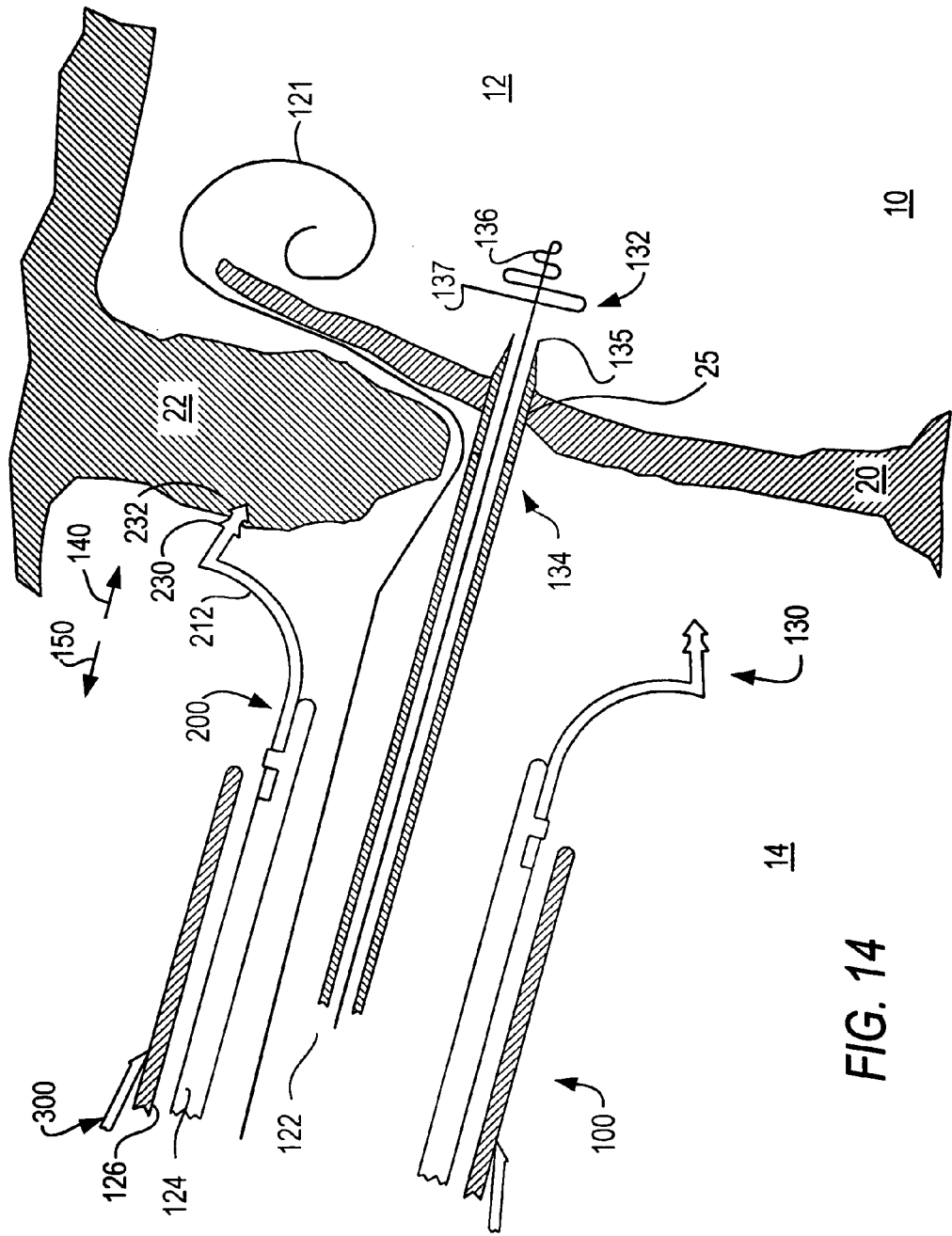
FIG. 14 is a cross-sectional view of the heart, gathering device, retaining device, and apparatus of FIG. 13, in a second stage of a procedure, in accordance with the present invention.

Once the physician determines the location of PFO 24, the distal portion 130 of apparatus 100 may be positioned adjacent the lumen of PFO 24. More particularly, transeptal apposition mechanism 132 may preferably be used to pass through septum primum 20 to provide positive apposition on the tissue from the left atrium 12. Cannula needle 134 may preferably be extended distally in the direction of arrow 140. As illustrated in FIG. 14, the sharpened tip 135 pierces the tissue of septum primum 20 at location 25, substantially in the direction of distal arrow 140. Location 25 is preferably chosen to be as close as possible to the bottom edge of the opening of the lumen of PFO 24 in the right atrium 14, and the transeptal puncture is preferably made at a perpendicular angle to the wall of septum primum 20, such that tip 135 at least partially penetrates septum primum 20 without penetrating septum secundum 22, and such that tip 135 may enter into the cavity of left atrium 12 without tangentially reentering a wall of left atrium 12. Although needle 134 of mechanism 132 is shown to distally advance in the direction of arrow 140, substantially along the longitudinal axis of support members 122-128, it is to be understood that transeptal apposition mechanisms of the present invention may be biased to extend from the distal end of apparatus 100 at any angle that may be desirable to facilitate closure of a particular defect (see, e.g., FIG. 77).

Once tip 135 of needle 134 has at least partially passed through the tissue of septum primum 20 and preferably into left atrium 12, the physician may pass the distal end 137 of wire 136 distally through the distal end 135 of needle 134 and into the left atrium 12 of the patient. As described above, and as shown in FIG. 14, the distal portion of wire 136 is preferably shaped such that it deflects back proximally towards the tissue wall of septum primum 20 to resist passage back through the tissue that has been penetrated by mechanism 132 and to provide positive apposition force to the tissue wall from the left atrium 12, as will be described in greater detail hereinbelow. It should be noted, however, that tip 135 need not completely pass through the tissue of septum primum 20, but may only partially pass therethrough. In such an embodiment, the distal portion of wire 136 alone may finish passing through the tissue of septum primum 20 before deflecting proximally. Or, in another embodiment, the distal portion of wire 136 may deflect proximally while within the tissue walls of septum primum 20. In either case, a penetration hole created by needle 134 through septum primum 20 is avoided.

Preferably before, or during, deployment of mechanism 132 at location 25 of septum primum 20, mechanism 131 may be employed such that gathering device 200 attains its expanded configuration by proximally retracting support member 126 with respect to support member 124, or by distally advancing support member 124 with respect to support member 126, or by both advancing support member 124 and retracting support member 126. Once gathering device 200 has been deployed into its expanded configuration, support member 124 is preferably advanced distally in the direction of arrow 140 such that the free end portion 232 of one or more fingers 212 at least engages the tissue of septum secundum 22, as shown in FIG. 14. This contact, however minimal, between gathering device 200 and tissue of septum secundum 22 preferably provides apposition force from the right atrium 14 to tissue surrounding PFO 24 to aid in the transeptal passage of mechanism 132 from the right atrium 14 to the left atrium 12 or in the engagement of wire 136 of mechanism 132 with tissue of septum primum 20 in the left atrium 12.

Figure 15:
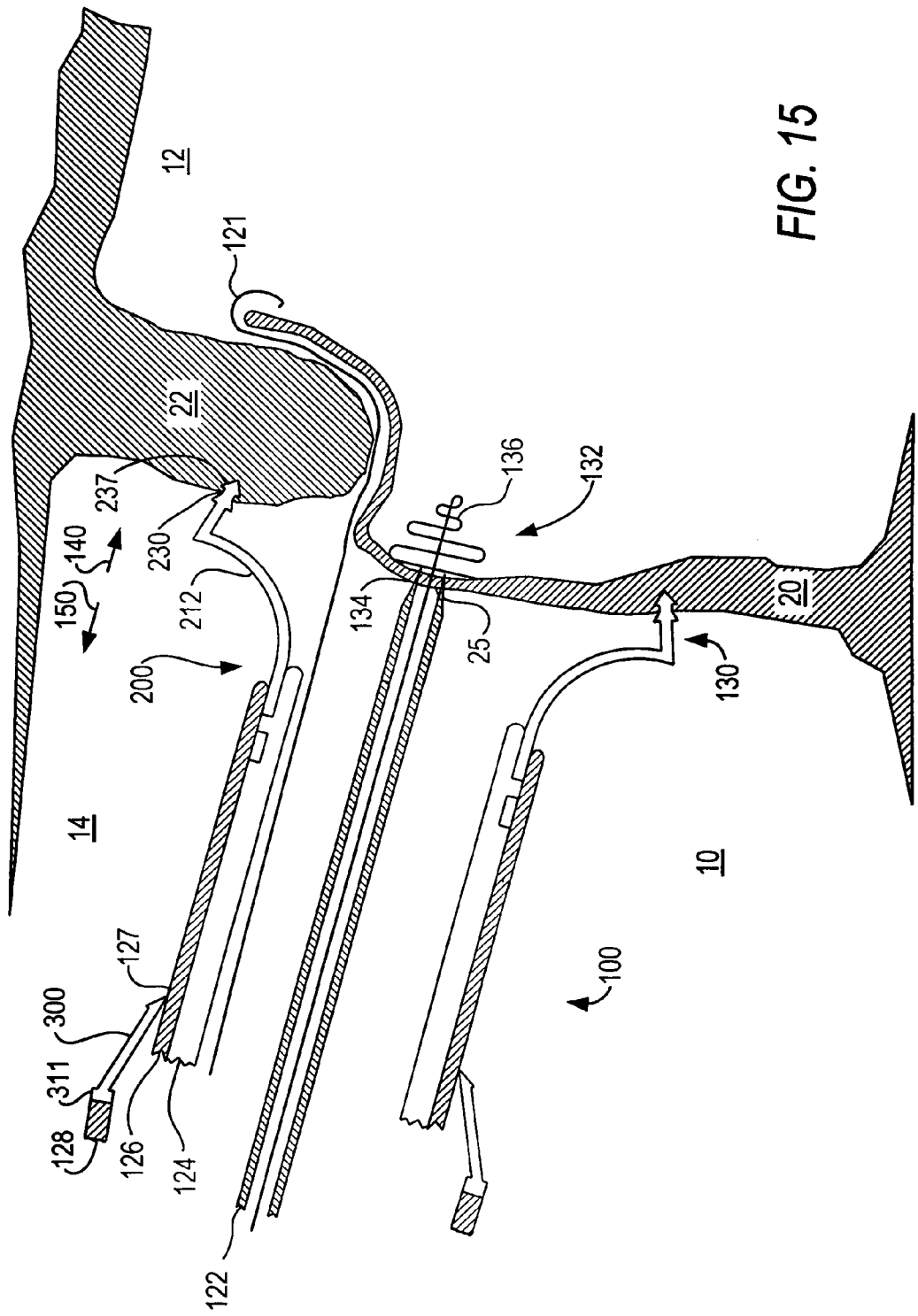
FIG. 15 is a cross-sectional view of the heart, gathering device, retaining device, and apparatus of FIGS. 13 and 14, in a third stage of a procedure, in accordance with the present invention.

A later stage in the use of apparatus 100 is illustrated in FIG. 15. Once tip 135 of needle 134 has passed transeptally through septum primum 20 and the distal end 137 of wire 136 has formed its deflected shape in left atrium 12 adjacent location 25, mechanism 132 may be retracted proximally in the direction of arrow 150 such that distal end 137 of wire 136 provides proximal apposition force against tissue of septum primum 20 from the left atrial side of PFO 24. Preferably, engaging septum tissue and providing positive apposition from the left side of PFO 24 by retracting mechanism 132 proximally pulls tissue from septum primum 20 and septum secundum 22 adjacent PFO 24 proximally into the area between fingers 212 of gathering device 200. Tissue gathered from both septum primum 20 and septum secundum 22 is thereby preferably engaged by and provided with positive apposition from the right side of PFO 24 by fingers 212. The physician may selectively advance support member 124 (and thus, gathering device 200) distally in the direction of arrow 140 to increase the positive apposition force applied by fingers 212 on the septum tissue from the right atrial side of PFO 24, such that free end portion 232 of each one of fingers 212 is engaging a portion of tissue of septum primum 20 and/or septum secundum 22 about the lumen of PFO 24.

Figure 16:
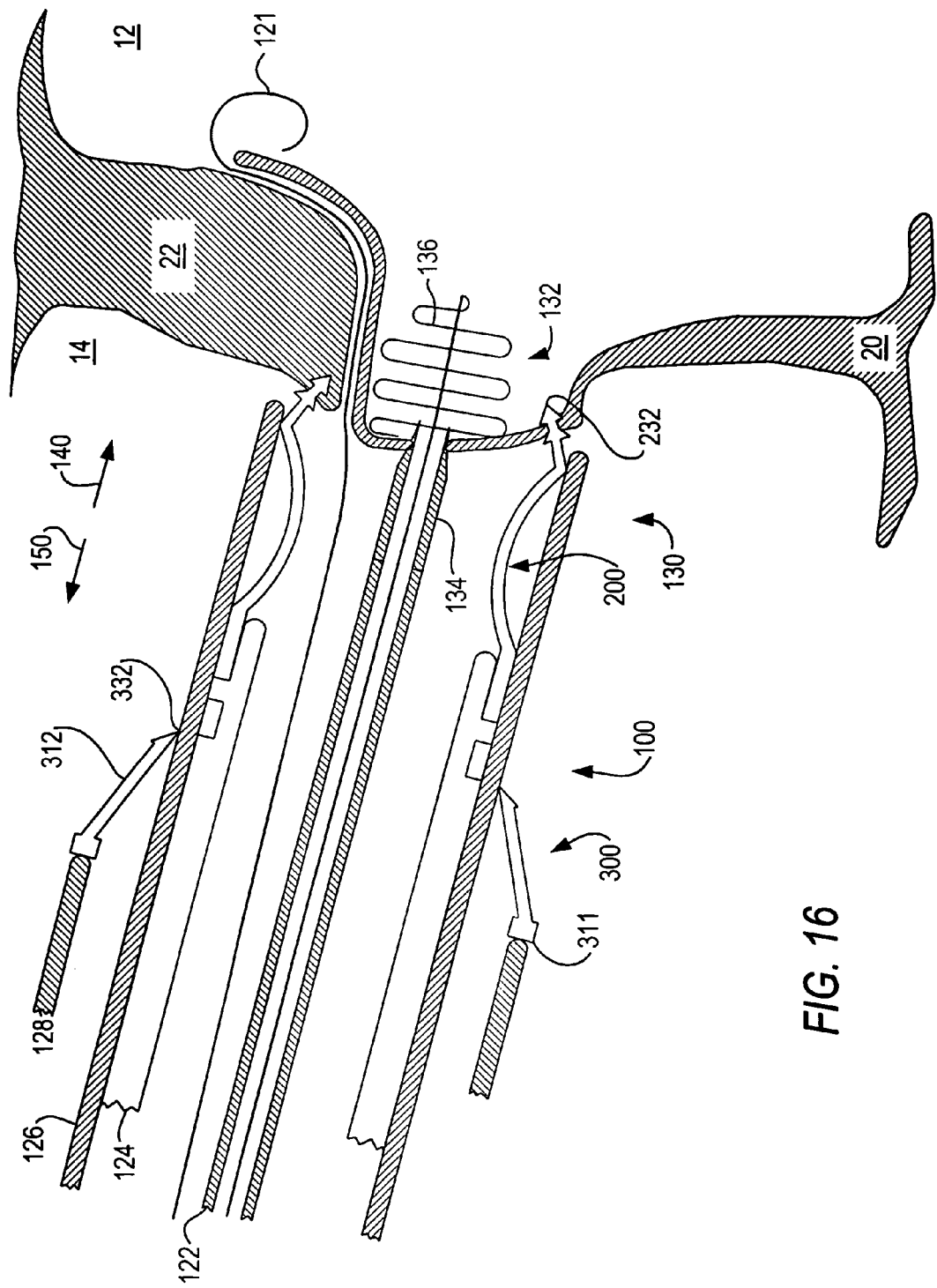
FIG. 16 is a cross-sectional view of the heart, gathering device, retaining device, and apparatus of FIGS. 13-15, in a fourth stage of a procedure, in accordance with the present invention.

Once septum primum tissue is engaged and has positive apposition force applied thereto by mechanism 132 from the left side of PFO 24, and once septum primum and septum secundum tissue is engaged and has positive apposition force applied thereto by gathering device 200 from the right side of PFO 24, support member 126 is preferably advanced distally in the direction of arrow 140 with respect to member 124, such that gathering device 200 becomes retained in its constricted configuration, as shown in FIG. 16. By retaining gathering device 200 in its constricted configuration, both after free end portions 232 have engaged septum primum 20 and/or septum secundum 22 tissue and after apposition mechanism 132 has been retracted proximally to provide positive tissue apposition from the left atrium, fingers 212 preferably have gathered therein not only septum primum and septum secundum tissue residing close together but also tissue from the septum primum that has been stretched so as to be folded over onto itself. As illustrated, this procedure preferably appositions the septal tissue about the PFO such that it is gathered and held in a significantly smaller or reduced area. Preferably, the effect of reducing the area by gathering the tissue from both the septum primum and septum secundum (i.e., tissue circumferentially around the PFO from both the left and right sides of the PFO) closes the lumen of the PFO directly or stretches it tight such that the lumen may not be opened under physiological pressure. It is to be understood that gathering device 200 (and any of the other gathering devices of the present invention described hereinabove and hereinbelow) may be selectively retained in varying degrees between its fully expanded configuration (see, e.g., FIG. 15) and its fully constricted configuration (see, e.g., FIG. 16) depending upon the amount of tissue to be gathered and the type of defect to be closed, for example.

Distal advancement of outer support member 128 with respect to support member 126, such that its distal end is substantially in the same plane as the distal end of support member 126, as shown in FIG. 17, permits free end portions 332 of retaining device 300 to penetrate tissue from septum primum 20 and septum secundum 22 at locations substantially about fingers 212. As illustrated by FIG. 17, inverted fingers 312 are impeded from resiliently passing back proximally through opening 315 of inverted annular element 310 to their original position by the distal end of support member 126.

Preferably, once free end portions 332 of retaining device 300 penetrate and engage tissue from septum primum 20 and septum secundum 22 at locations substantially about fingers 212 and the lumen of PFO 24, transeptal apposition mechanism 132 is retracted proximally in the direction of arrow 150 from the left atrial side of the PFO. In a first embodiment of the present invention, distal portion 137 of wire 136 may be retracted proximally in the direction of arrow 150 through needle 134, as it is positioned in FIG. 17. In another embodiment, needle 134 may be substantially advanced distally in the direction of arrow 140 into the cavity of left atrium 12, such that wire 136 may be fully retracted proximally into the lumen of needle 134 without putting additional pressure on the left atrial wall of septum primum 20 before completely retracting mechanism 132 proximally from the left atrial side of the PFO. In yet another embodiment, distal portion 137 may be retained within the left atrium 12 to apposition the tissue long-term.

Figure 1C:
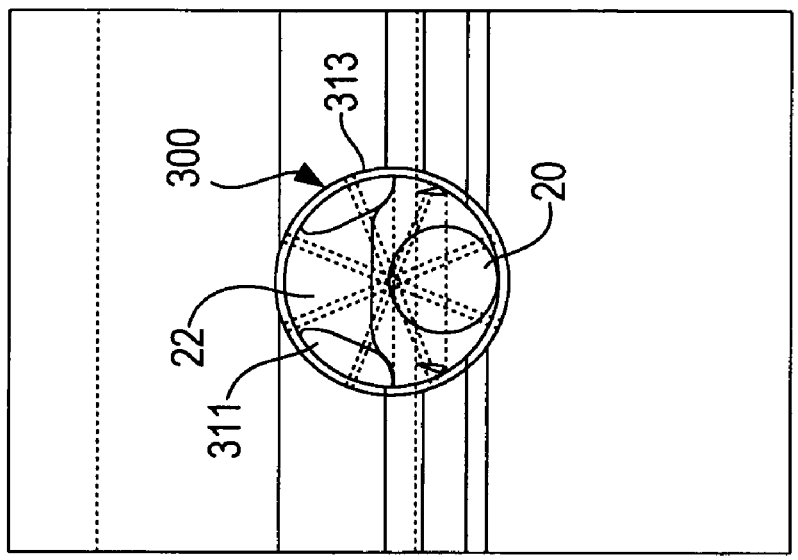
FIG. 1C is a front elevational view of the secured portion of the heart of FIG. 1B, taken from line 1C-1C of FIG. 1B, but with some tissue of the secured portion omitted.
Figure 1B:
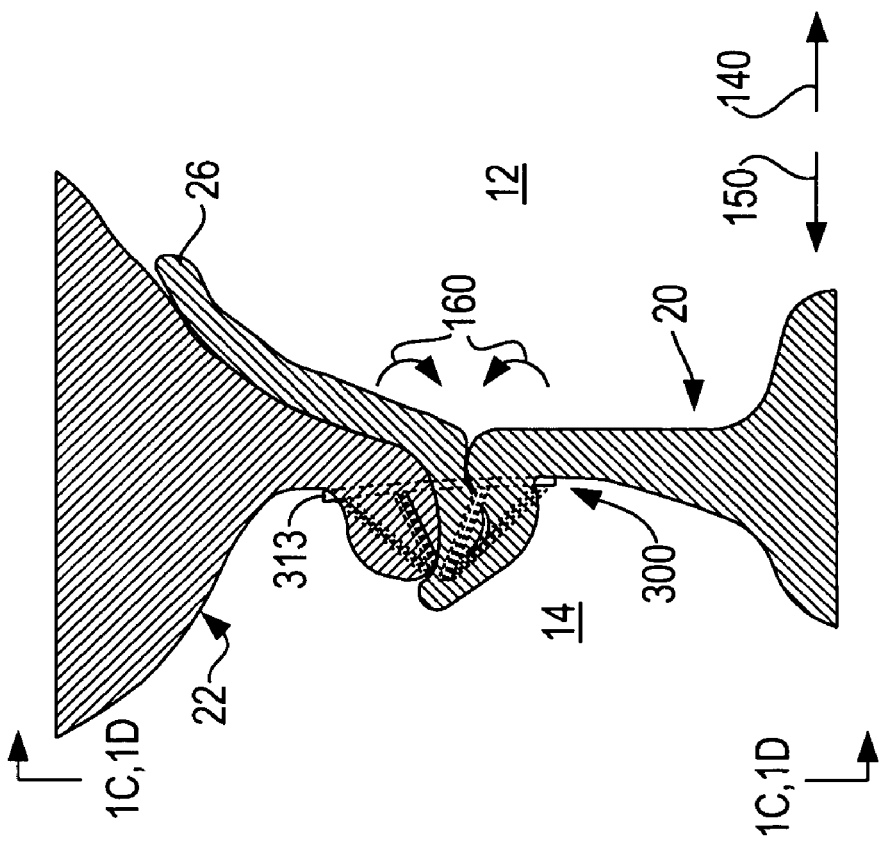
FIG. 1B is a cross-sectional view similar to FIG. 1A of the gathered portion of the heart of FIG. 1A secured by an illustrative embodiment of a retaining device constructed in accordance with the present invention.

Fingers 312, and thus annular element 310, may be subsequently deployed to their original (non-inverted) position to complete the closure of PFO 24. This may preferably be accomplished by retracting support member 126 proximally in the direction of arrow 150 with respect to support member 128 and/or by advancing support member 128 distally in the direction of arrow 140 with respect to support member 126, such that fingers 312 may resiliently pass back proximally through opening 315 of annular element 310 along with whatever septum tissue is engaged by free end portions 332 (in the direction indicated by arrows 160), as shown in FIG. 1B, for example. This reconfiguration of the retaining device after deployment preferably benefits not only the retention of the gathered tissue but also the positioning of the gathered tissue with respect to the retention features of the device and the atrial chambers.

Figure 1D:
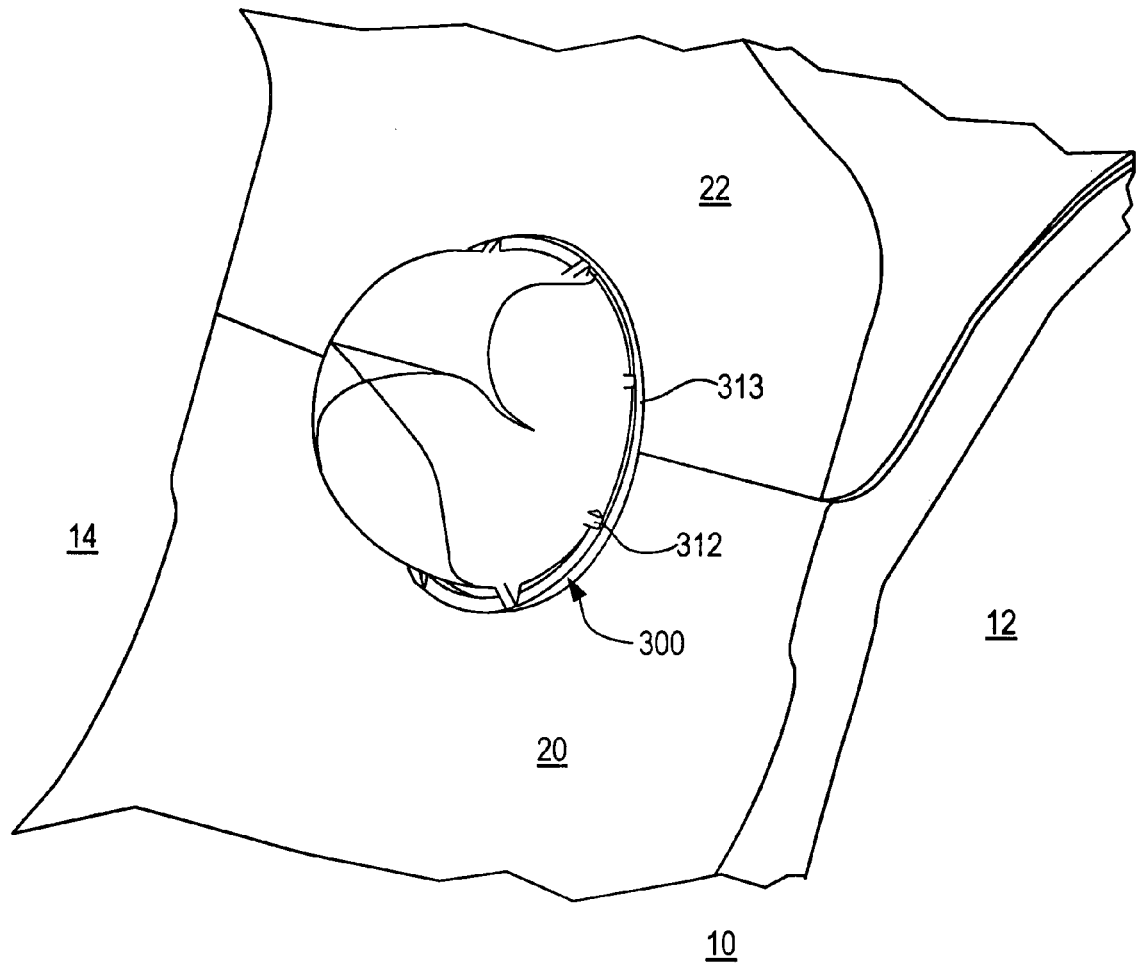
FIG. 1D is a partially sectional perspective view of the secured portion of the heart of FIGS. 1B and 1C, taken from line 1D-1D of FIG. 1B.

The closure of PFO 24 is complete, and support members 122-128 and guide wire 121 of apparatus 100 are then preferably subsequently retracted proximally in the direction of arrow 150 and completely removed from the operative site. Gathering device 200 preferably comes out of the patient with these apparatus elements. As illustrated in FIGS. 1B-1D, retaining device 300 preferably secures the gathered tissue from septum primum 20 and septum secundum 22 and retains the tissue in a substantially reduced area such that no fluid may flow through the lumen of PFO 24 between atriums 12 and 14 and such that the lumen may not be opened under physiological pressure.

An alternative embodiment of the retaining device in accordance with the present invention is described herein. The apparatus and procedures are substantially identical to those described above with respect to FIGS. 1-17, with the substantial differences described hereinbelow with respect to FIGS. 18-22.

Figure 18:
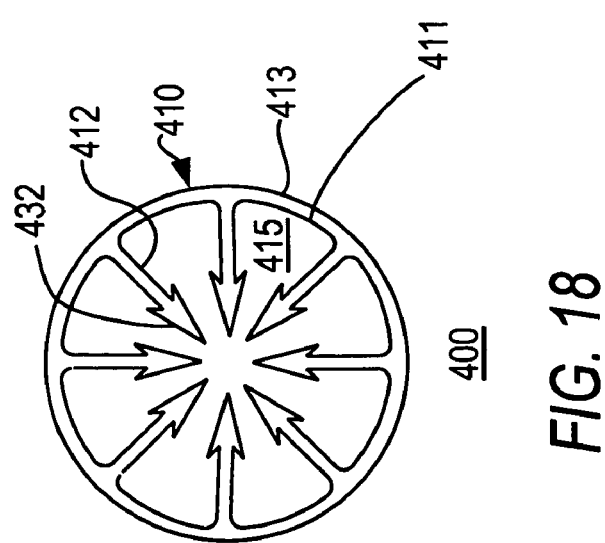
FIG. 18 is a top elevational view of the structure of another illustrative embodiment of a retaining device constructed in accordance with the present invention.

As illustrated in FIG. 18, retaining device 400 may generally be described as including a substantially annular element 410 having an outer surface 413, an inner surface 411, and an opening 415 defined therein, which may be round, oval, or any other substantially smooth shape. Preferably, annular element 410 of gathering device 400 may be annularly expandable or enlargeable, as will be described in greater detail hereinbelow. Retaining device 400 may also include one or more tissue retention features or fingers 412 projecting inwardly from inner surface 411 of annular element 410, each with a free end portion 432. It is to be understood that tissue retention fingers 412 may be of variable frequency and length about annular element 410, and free end portions 432 may be of variable lengths and shapes, such as "fanged" or "barbed," for example. It should be understood that the size and shape of opening 415 and of each of fingers 412 and end portions 432 may be altered according to the type, size, and shape of the defect to be closed, and to the particular free end portion's orientation to the defect when deployed in the patient (e.g., whether the end portion is to engage the septum primum, the septum secundum, or both). Annular element 410 of retaining device 400 may preferably be made of any biocompatible polymer or elastomer, while retention fingers 412 may preferably be made of any appropriate materials.

Figure 19:
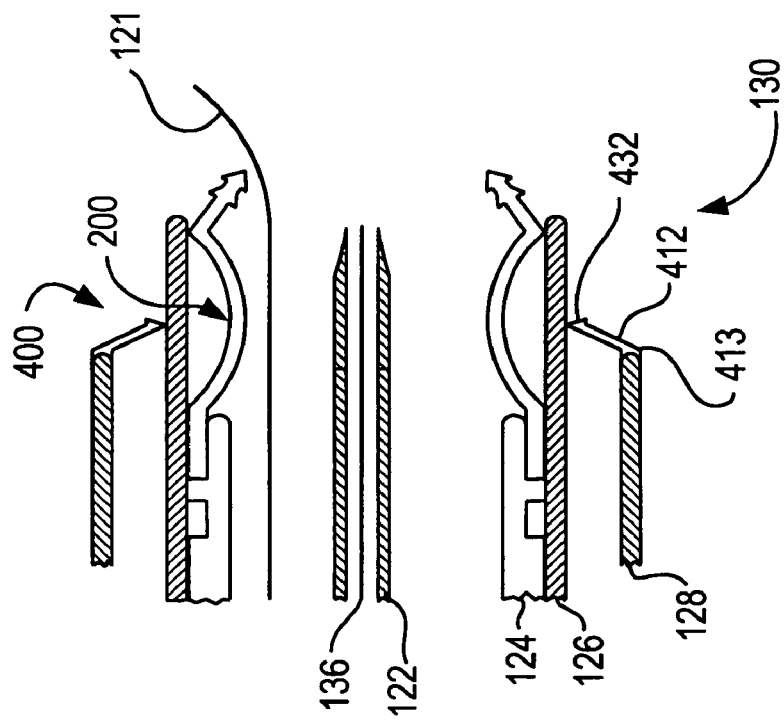
FIG. 19 is a cross-sectional view of the gathering device and apparatus of FIGS. 11-17, but in conjunction with the retaining device of FIG. 18, in the early stage of the procedure of FIG. 11, in accordance with the present invention.

Opening 415 of annular element 410 is preferably expanded (e.g., by elastic deflection of fingers 412 out of the plane of the paper on which FIG. 18 is drawn and/or by annular expansion of element 410 itself in the plane of the paper on which FIG. 18 is drawn) for the mounting of retaining device 400 to distal portion 130 of apparatus 100, as shown in FIG. 19. This expansion preferably provides the necessary resilient force for fingers 412 of retaining device 400 to be positioned annularly about support member 126 and to tend to remain thereon. Outer support member 128 may proximally abut retaining device 400 at annular element 410 for assisting in deploying retaining device 400 in the patient, as will be described in greater detail hereinbelow.

Figure 20:
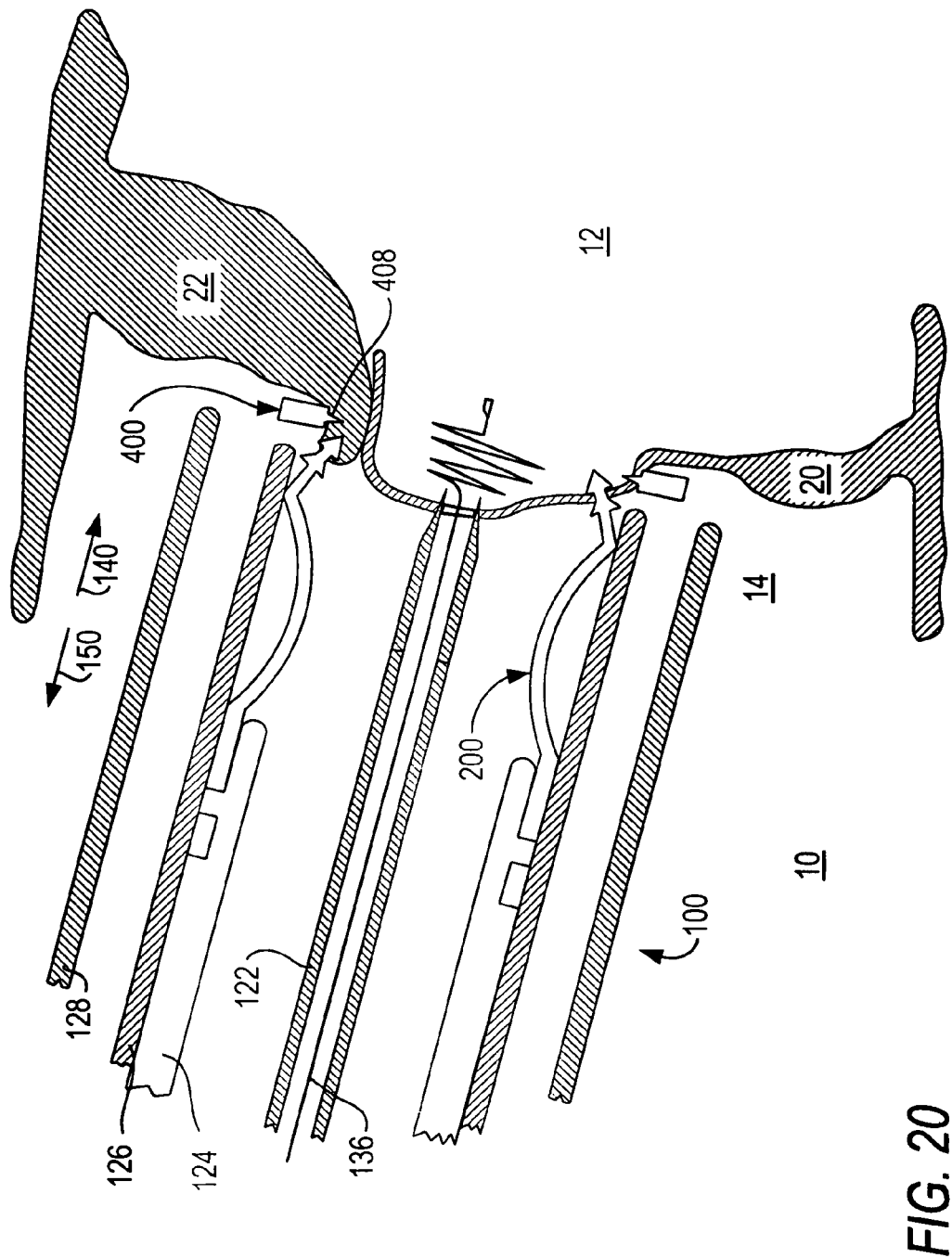
FIG. 20 is a cross-sectional view of a portion of the heart of FIG. 1, illustrated with the gathering device, retaining device, and apparatus of FIG. 19, in the fifth stage of a procedure of FIG. 17, in accordance with the present invention.
Figure 22:
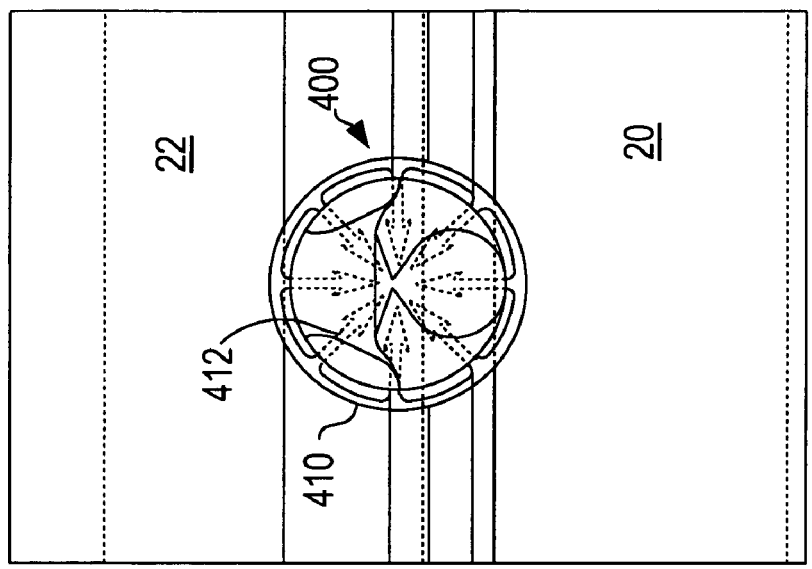
FIG. 22 is a front elevational view of the secured portion of the heart of FIG. 21, taken from line 22-22 of FIG. 21, but with some tissue of the secured portion omitted.
Figure 21:
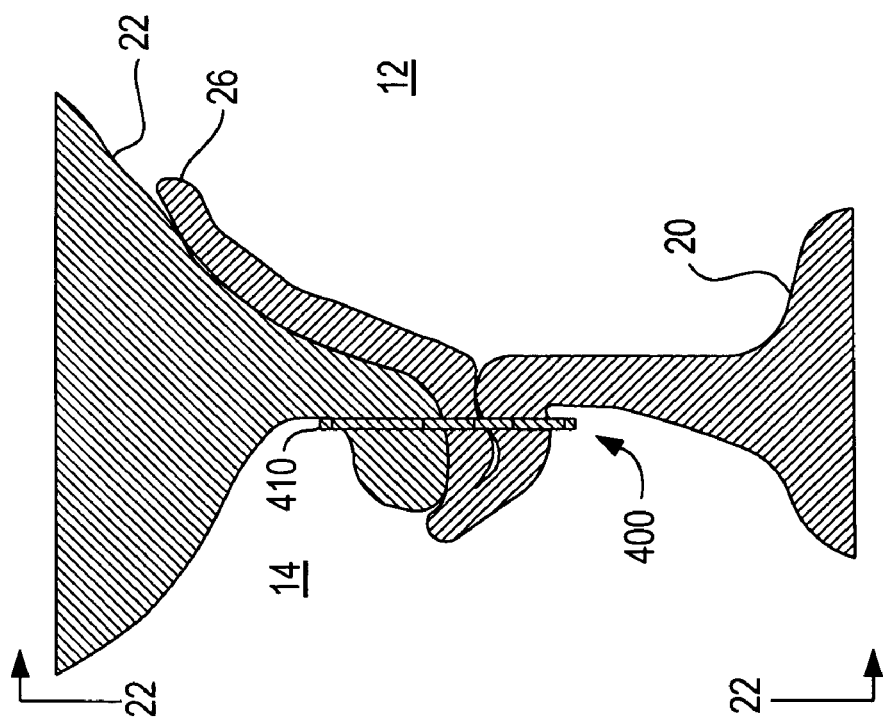
FIG. 21 is a cross-sectional view, similar to FIG. 1B, of the gathered portion of the heart of FIG. 1A secured by the retaining device of FIGS. 19 and 20, in accordance with the present invention.

As shown in FIG. 20, preferably once the gathering device (e.g., device 200) has been returned to its constricted configuration and after the apposition mechanism (e.g., mechanism 132) has been retracted proximally in the direction of arrow 150 to provide positive tissue apposition from left atrium 12, such that tissue from the septum primum and septum secundum preferably reside close together within the fingers of the gathering device, distal advancement of outer support member 128 with respect to support member 126 in the direction of arrow 140 permits annular element 410 of retaining device 400 to resiliently contract to its originally non-expanded configuration about the gathered septal tissue. Free end portions 432 of fingers 412 preferably engage the periphery of the gathered tissue and retain the tissue within opening 415 of retaining device 400. The closure of the PFO using retaining device 400 is complete, and apparatus 100 (including transeptal apposition mechanism 132 and gathering device 200) is subsequently removed from the operative site, as shown in FIGS. 21 and 22.

Another alternative embodiment of the retaining device in accordance with the invention is described herein. The apparatus and procedures are substantially identical to those described above with respect to FIGS. 1-22, with the substantial differences described hereinbelow with respect to FIGS. 23-25.

Figure 23:
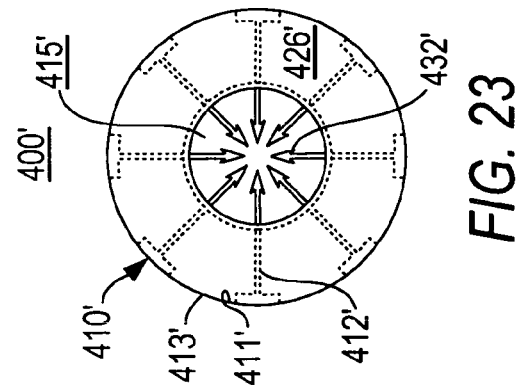
FIG. 23 is a top elevational view of the structure of yet another illustrative embodiment of a retaining device constructed in accordance with the present invention.

As illustrated in FIG. 23, retaining device 400' may be substantially similar to device 400 described above with respect to FIGS. 18-22, but may further include a cover 426' that may be supported by fingers 412' and that may run from inner surface 411' of annular element 410' along fingers 412' towards free end portions 432'. Preferably, cover 426' of gathering device 400' may be annularly expandable or enlargeable, as will be described in greater detail hereinbelow. Cover 426' can also be folded and unfolded to allow annular element 410' to deform during deployment in the patient. A foldable and unfoldable cover 426' can be either elastic or non-elastic and may include a cloth or polymeric material. Cover 426' of retaining device 400' may preferably be made of any elastic material, such as Dacron®.

Figure 25:
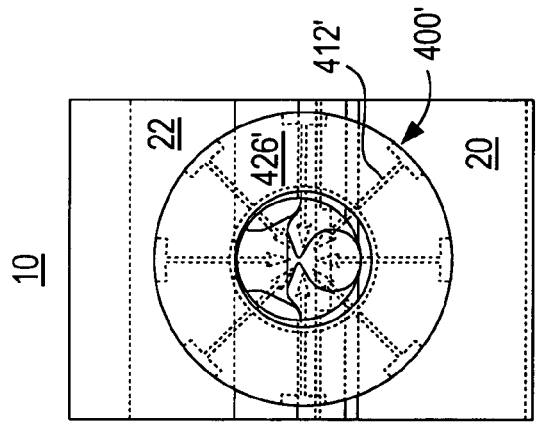
FIG. 25 is a front elevational view of the secured portion of the heart of FIG. 24, taken from line 25-25 of FIG. 24, but with some tissue of the secured portion omitted.
Figure 24:
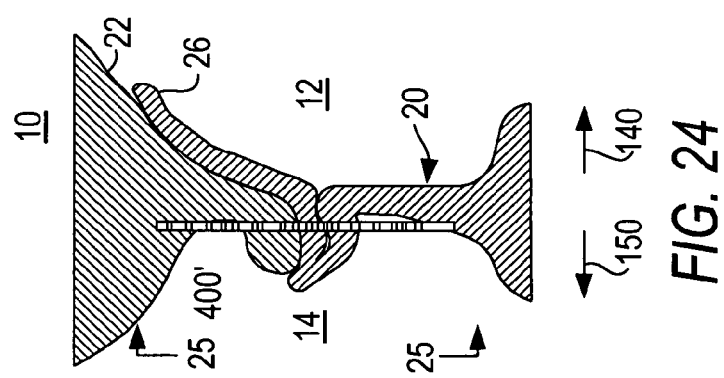
FIG. 24 is a cross-sectional view, similar to FIG. 1B, of the gathered portion of the heart of FIG. 1A secured by the retaining device of FIG. 23, in accordance with the present invention.

Device 400' may be mounted on apparatus 100 and deployed in a patient similarly to device 400 (see, e.g., FIGS. 19 and 20). As illustrated in FIGS. 24 and 25, when a PFO in heart 10 is closed using retaining device 400', cover 426' may constrict about the outer periphery of the tissue retained by fingers 412' and may lie against the right atrial wall of septums primum and secundum, thereby promoting tissue ingrowth in a larger area about the PFO ostium than the device would without a cover.

Yet another alternative embodiment of the retaining device in accordance with the invention is described herein. The apparatus and procedures are substantially identical to those described above with respect to FIGS. 1-25, with the substantial differences described hereinbelow with respect to FIGS. 26 and 27.

Figure 27:
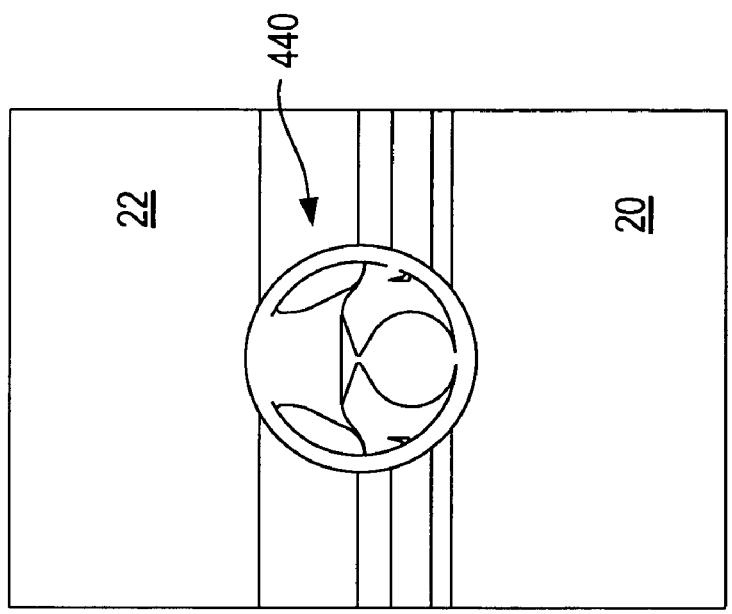
FIG. 27 is a front elevational view of the secured portion of the heart of FIG. 26, taken from line 27-27 of FIG. 26, but with some tissue of the secured portion omitted.
Figure 26:
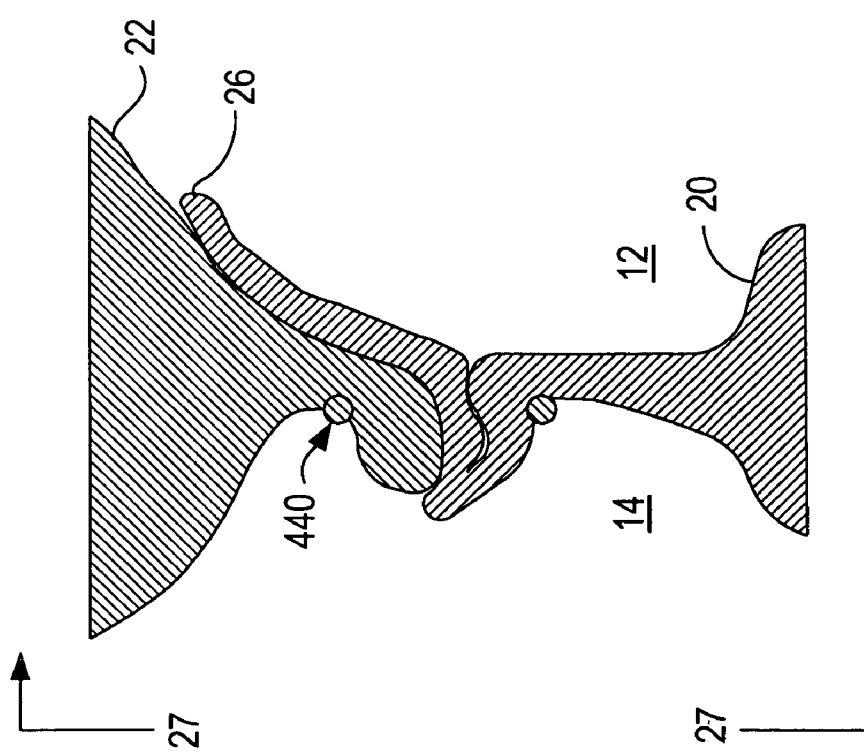
FIG. 26 is a cross-sectional view, similar to FIG. 1A, of the gathered portion of the heart of FIG. 1A secured by still another illustrative embodiment of a retaining device constructed in accordance with the present invention.

As illustrated in FIGS. 26 and 27, retaining device 440 may generally be described as a suture or other material sufficient to constrict the prolapsed or gathered tissue together. Device 440 may preferably be mounted on apparatus 100 and deployed in a patient similarly to retaining device 300, as described hereinabove.

Still another alternative embodiment of the retaining device in accordance with the invention is described herein. The apparatus and procedures are substantially identical to those described above with respect to FIGS. 1-27, with the substantial differences described hereinbelow with respect to FIGS. 28 and 29.

Figure 29:
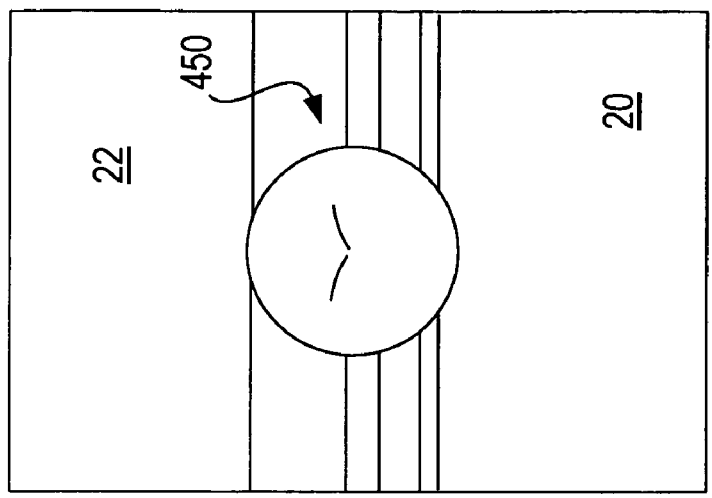
FIG. 29 is a front elevational view of the secured portion of the heart of FIG. 28, taken from line 29-29 of FIG. 28, but with some tissue of the secured portion omitted.
Figure 28:
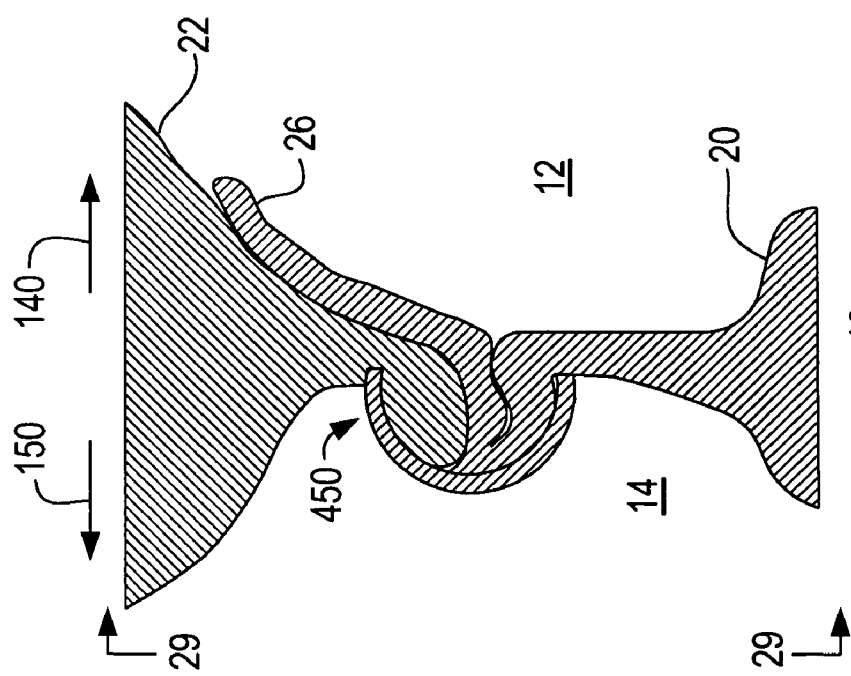
FIG. 28 is a cross-sectional view, similar to FIG. 1A, of the gathered portion of the heart of FIG. 1A secured by yet another illustrative embodiment of a retaining device constructed in accordance with the present invention.

As illustrated in FIGS. 28 and 29, retaining device 450 may generally be described as an adhesively-backed structure that may conform to the tissue (or to which the tissue may conform) and hold the tissue in its gathered position. Device 450 may preferably be mounted on apparatus 100 and deployed in a patient similarly to retaining device 300, as described hereinabove.

Yet another alternative embodiment of the retaining device in accordance with the invention is described herein. The apparatus and procedures are substantially identical to those described above with respect to FIGS. 1-31, with the substantial differences described hereinbelow with respect to FIGS. 32-35.

As illustrated in FIGS. 32-35, retaining device 470 may generally be described as including a suture-like structure 472 which may be made of any suitable malleable material. Additional cannulas may be provided by apparatus 100, which preferably may pass through the gathered tissue of the septums primum and secundum to allow structure 472 to be placed therethrough. Once structure 472 has been deployed in the gathered tissue, its ends may be fixed together to retain the tissue thereby using a knot, suture clip, tie wire, or any other commonly known tying mechanism 474. Multiple ones of device 470 may preferably be deployed in the gathered tissue to close the defect.

Still another alternative embodiment of the retaining device in accordance with the invention is described herein. The apparatus and procedures are substantially identical to those described above with respect to FIGS. 1-35, with the substantial differences described hereinbelow with respect to FIGS. 36-39.

As illustrated in FIGS. 36-39, retaining device 480 may generally be described as a helical coil. Device 480 may preferably be deployed in the gathered tissue similarly to device 470. However, device 480 is preferably held in place to retain the gathered tissue by its helical shape.

Yet another alternative embodiment of the retaining device in accordance with the invention is described herein. The apparatus and procedures are substantially identical to those described above with respect to FIGS. 1-39, with the substantial differences described hereinbelow with respect to FIGS. 40 and 41.

Figure 41:
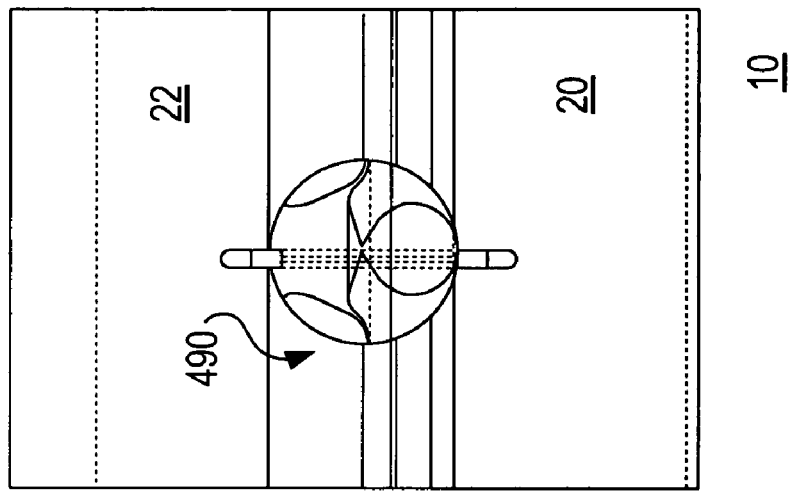
FIG. 41 is a front elevational view of the secured portion of the heart of FIG. 40, taken from line 41-41 of FIG. 40, but with some tissue of the secured portion omitted.
Figure 40:
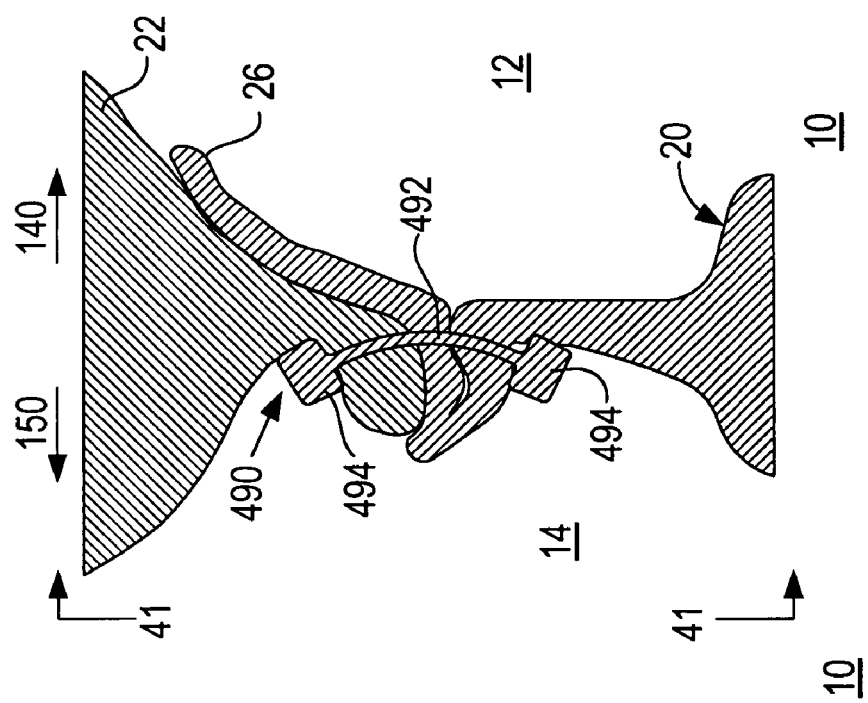
FIG. 40 is a cross-sectional view, similar to FIG. 1A, of the gathered portion of the heart of FIG. 1A secured by still another illustrative embodiment of a retaining device constructed in accordance with the present invention.

As illustrated in FIGS. 40 and 41, retaining device 490 may generally be described as including a suture-like structure 492 which may be made of any suitable malleable material, similarly to structure 472. Additional cannulas may be provided by apparatus 100, which preferably may pass through the gathered tissue of the septums primum and secundum to allow structure 492 to be placed therethrough. Once structure 492 has been deployed in the gathered tissue, its ends may each be separately anchored to retain the tissue thereby using a knot, barb, suture clip, or any other commonly known anchoring mechanism 494. Multiple ones of device 490 may preferably be deployed in the gathered tissue to close the defect.

Still another alternative embodiment of the retaining device in accordance with the invention is described herein. The apparatus and procedures are substantially identical to those described above with respect to FIGS. 1-17, with the substantial differences described hereinbelow with respect to FIGS. 42-45.

Figure 45:
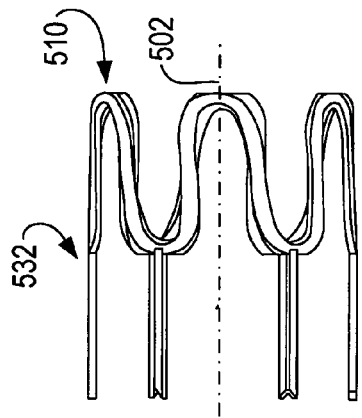
FIG. 45 is a side elevational view of the retaining device of FIGS. 42-44, taken from line 45-45 of FIG. 43.
Figure 42:
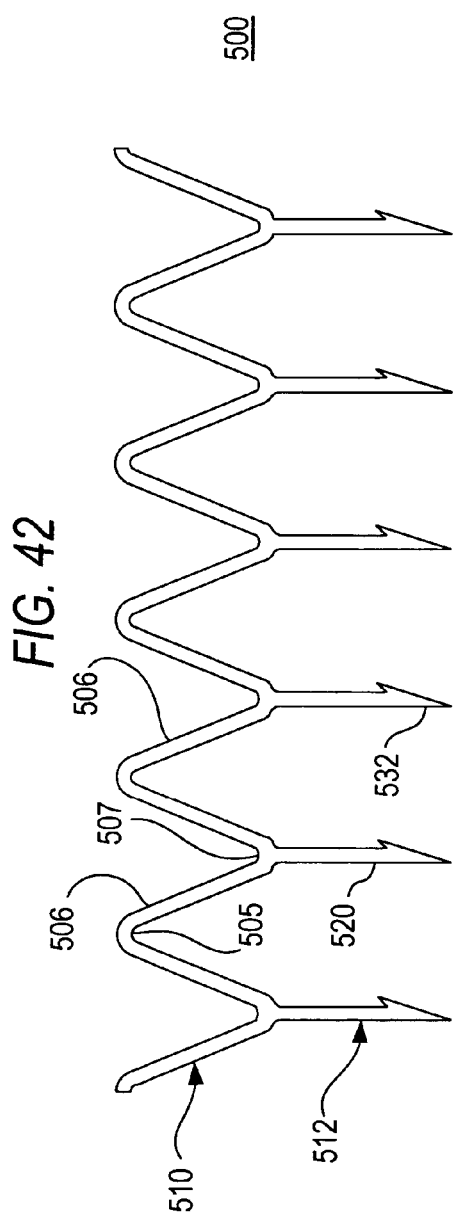
FIG. 42 is a planar development of yet another illustrative embodiment of a retaining device constructed in accordance with the present invention.
Figure 44:
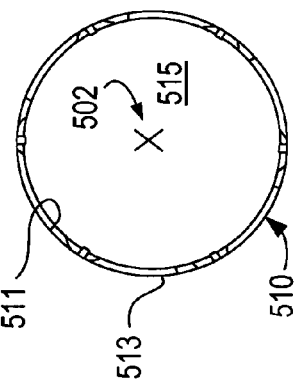
FIG. 44 is a top elevational view of the retaining device of FIGS. 42 and 43, taken from line 44-44 of FIG. 43.
Figure 43:
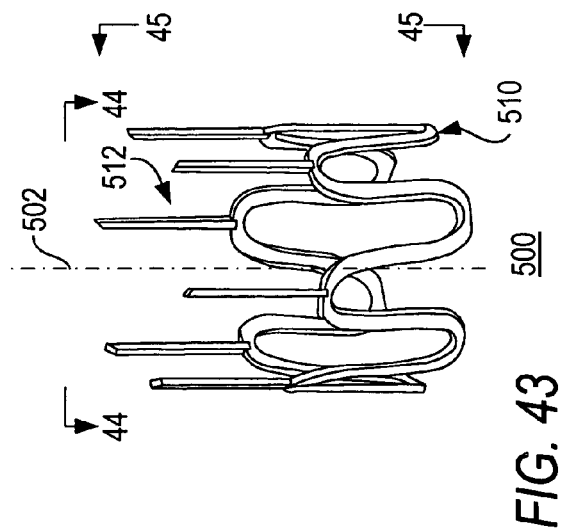
FIG. 43 is a perspective view of the retaining device of FIG. 42, in a functional configuration, in accordance with the present invention.

As illustrated in FIGS. 42-45, retaining device 500 may be similar to retaining device 300, described hereinabove, and may include a plurality of fingers to engage and retain the tissue of the septum primum and the septum secundum about the PFO lumen gathered by a gathering device of the present invention (e.g., device 200). FIG. 42 shows a planar development of what is actually, preferably, an integral, one-piece (unitary), annular, retaining device 500. In particular, the left and right edges of the structure shown in FIG. 42 are actually, preferably, joined to and integral with one another. Thus, the actual structure of retaining device 500 is as shown in FIGS. 43-45, although FIG. 42 is useful to more clearly reveal certain details of various features of retaining device 500. A central longitudinal axis 502 about which retaining device 500 is annular is shown in FIGS. 43-45.

Like retaining device 300, a particularly preferred material for retaining device 500 is nitinol. Other examples of suitable materials are described hereinbelow. It should be noted that, depending on the material of the device, different techniques may be used to shape the structure of device 500 shown in FIG. 42 into approximately the fully functional geometry of FIGS. 43-45 that retaining device 500 will assume after full deployment.

Retaining device 500 may be described as including an annular element 510 comprised of a plurality of "V-shaped" extensions 506 that connect adjacent ones of a plurality of annularly spaced tissue retaining fingers 512 extending axially therefrom (at joints 507). According to one embodiment, retaining device 500 includes six fingers 512. Retaining device 500 may have fewer or more than six of fingers 512, depending on the type of defect to be closed and the tissue thereabout, and the size and shape of the particular defect. Alternatively, the structure of retaining device 500 may have different configurations of fingers and geometries.

Each retaining finger 512 preferably includes a medial extension member 520 and a tissue retaining feature that may include a barb-like free end portion 532 that is sharply pointed. The dimensions of each medial member 520 and retaining feature may be altered according to the type, size, and shape of the defect to be closed, and to the particular finger's orientation to the defect when deployed in the patient (e.g., whether the finger is to engage the septum primum, the septum secundum, or both).

As shown in this example, unlike that of device 300, the cross-sectional area of retaining device 500 is expandable. Specifically, annular element 510 is a structure that may expand annularly (e.g., by deflection of joints 505 and 507 of extensions 506), and that has an outer surface 513, an inner surface 511, and an expandable opening 515 defined therein, which may be round, oval, or any other substantially smooth shape. It is to be understood that the structure of device 500 is purely exemplary, and that annular expandability of any of the devices described hereinabove or hereinbelow may be facilitated by constructing the frame (i.e., the substantially annular element) such that any cross-section perpendicular to its central axis is discontinuous.

In the fully functional configuration of retaining device 500 shown in FIGS. 43-45, the medial extension member 520 of each finger 512 may be resiliently deflected to extend away from annular element 510 at an angle substantially parallel to axis 502. Like the dimensions of each medial member 520 of each finger 512, orientation of fingers 512 with respect to axis 502 may be altered according to the type, size, and shape of the defect to be closed, and to the particular finger's orientation to the defect when deployed in the patient.

Retaining device 500 may be mounted on apparatus 100 and deployed in a patient similarly to retaining device 300 (see, e.g., FIGS. 11-17). In the fully functional configuration of retaining device 500 shown in FIGS. 43-45, the medial extension member 520 of each finger 512 may extend from annular element 510 parallel to longitudinal axis 502. However, similarly to retaining device 300 (see, e.g., FIGS. 11 and 12), fingers 512 are preferably elastically inverted or "rolled in" through opening 515 of annular element 510 to point in the opposite direction from their original position for the mounting of retaining device 500 to distal portion 130 of apparatus 100. Annular element 510 is also thereby at least partly inverted, such that at least part of inner surface 511 now faces outwardly and at least part of outer surface 513 faces inwardly towards axis 502 when mounted on the deployment apparatus. Device 500 may be subsequently deployed to engage and retain gathered tissue, similarly to device 300 (see, e.g., FIGS. 1B and 1C), such that fingers 512, and thus annular element 510, may resiliently return substantially towards their original (non-inverted) position (i.e., towards right atrium 14) to complete the closure of the PFO.

Figure 45B:
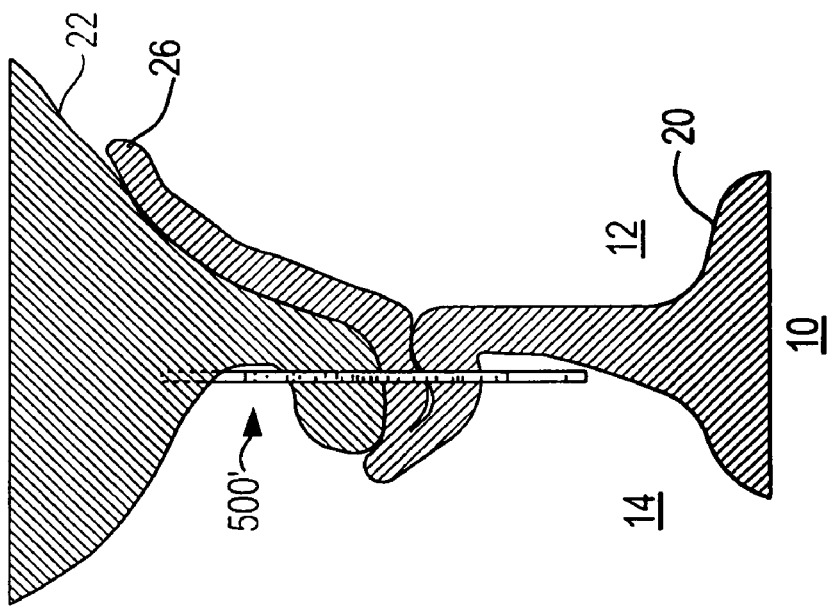
FIG. 45B is a cross-sectional view, similar to FIG. 1A, of the gathered portion of the heart of FIG. 1A secured by the retaining device of FIG. 45A, in accordance with the present invention.
Figure 45A:
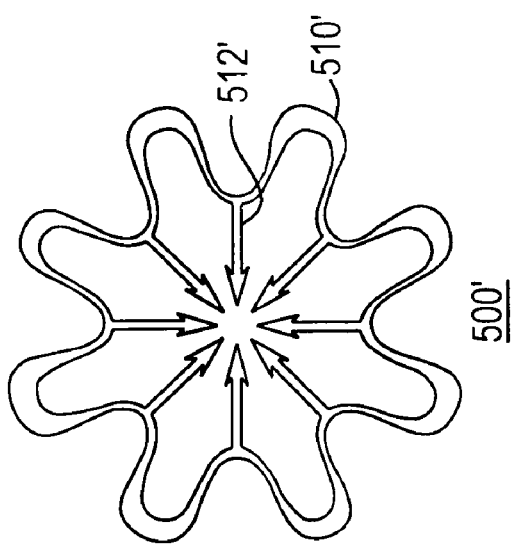
FIG. 45A is a top elevational view of still another illustrative embodiment of a retaining device constructed in accordance with the present invention.

Alternatively, the original (non-inverted) position of an expandable retaining device of the present invention, as shown by device 500' in FIGS. 45A and 45B, may be configured such that retaining fingers 512' extend radially inwardly from expandable annular element 510' in the plane of the paper on which FIG. 45A is drawn. Therefore, once the inverted structure of device 500' is deployed to engage and retain gathered tissue, fingers 512' may preferably resiliently return to their original position, substantially in the same plane as annular element 510', as shown in FIG. 45B.

When a PFO in heart 10 is closed using expandable retaining device 500 and the procedure described above, expandable annular element 510 may be expanded to fit about a larger support member 126 or constricted to fit about a smaller support member 126 than would be possible using retaining device 300 with fixed annular element 310.

An alternative embodiment of the gathering device in accordance with the invention is described herein. The apparatus and procedures are substantially identical to those described above with respect to FIGS. 1-17, with the substantial differences described hereinbelow with respect to FIGS. 46-48.

Figure 47:
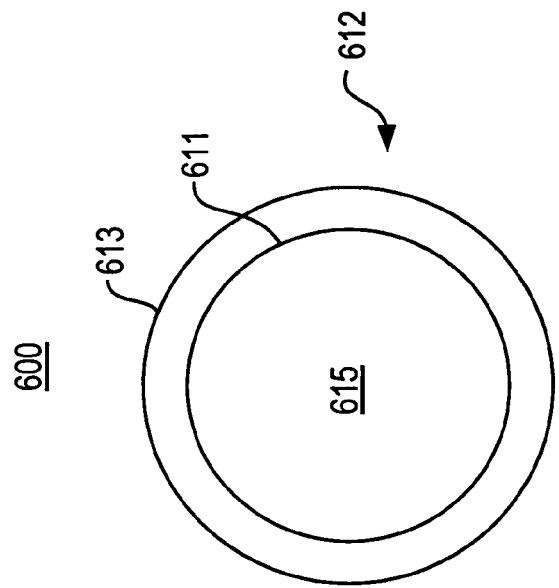
FIG. 47 is a rear elevational view of the gathering device of FIG. 46, taken from line 47-47 of FIG. 46.
Figure 46:
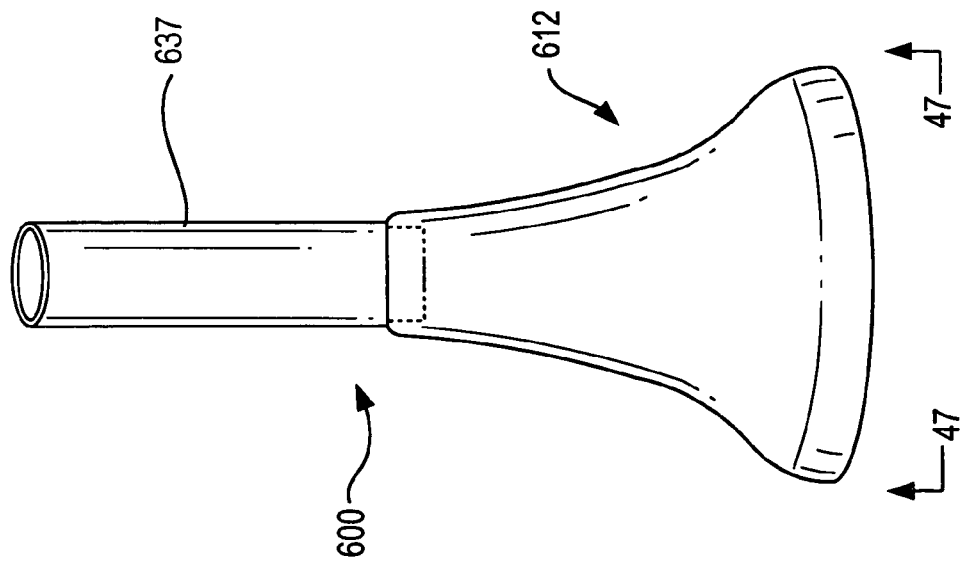
FIG. 46 is a top perspective view of another illustrative embodiment of a gathering device constructed in accordance with the present invention.

As illustrated in FIGS. 46-48, gathering device 600 may preferably include a substantially hollow conical or bell shaped receptacle 612 configured to promote capture of the tissue of the septum primum and the septum secundum. Receptacle 612 may be made of any suitable material that will allow for a liquid tight seal with the tissue for suctioning. The distal end of receptacle 612 (see, e.g., FIG. 47) may preferably have an outer surface 613, an inner surface 611, and an opening 615 defined therein, which may be round, oval, or any other substantially smooth shape. In a preferred embodiment, receptacle 612 of gathering device 600 may be annularly expandable, enlargeable, or pliant, at least at its distal end, to contour to the type, size, and shape of the defect to be closed.

Device 600 may also include a suction catheter 637 at the proximal end of receptacle 612. The sidewall of catheter tube 637 may include a separate lumen (not shown, but conventional for suction catheters) through which pressurized suction may be applied from a proximal region of the apparatus to receptacle 612. Catheter 637 may be slideable axially with receptacle 612.

Similarly to gathering device 200, device 600 may be mounted to the distal end of support member 124 of apparatus 100 for advancement and retraction within the heart of a patient, as shown in FIG. 48, for example. Preferably, in conjunction with positive apposition force in the direction of arrow 150 applied to the septum primum from the left atrium by a transeptal apposition mechanism of the present invention (e.g., mechanism 132), and/or in conjunction with any suction pressure that may be applied by suction catheter tube 637, receptacle 612 is distally advanced in the direction of arrow 140 to capture tissue of the septum primum and septum secundum from the right atrium, as described above with respect to device 200. The closure of PFO 24 may preferably be completed as described hereinabove or below using any of the retaining devices of the present invention (e.g., device 300).

An alternative embodiment of the gathering device and retaining device in accordance with the invention is described herein. The apparatus and procedures are substantially identical to those described above with respect to FIGS. 1-17, with the substantial differences described hereinbelow with respect to FIGS. 49-58.

Figure 49:
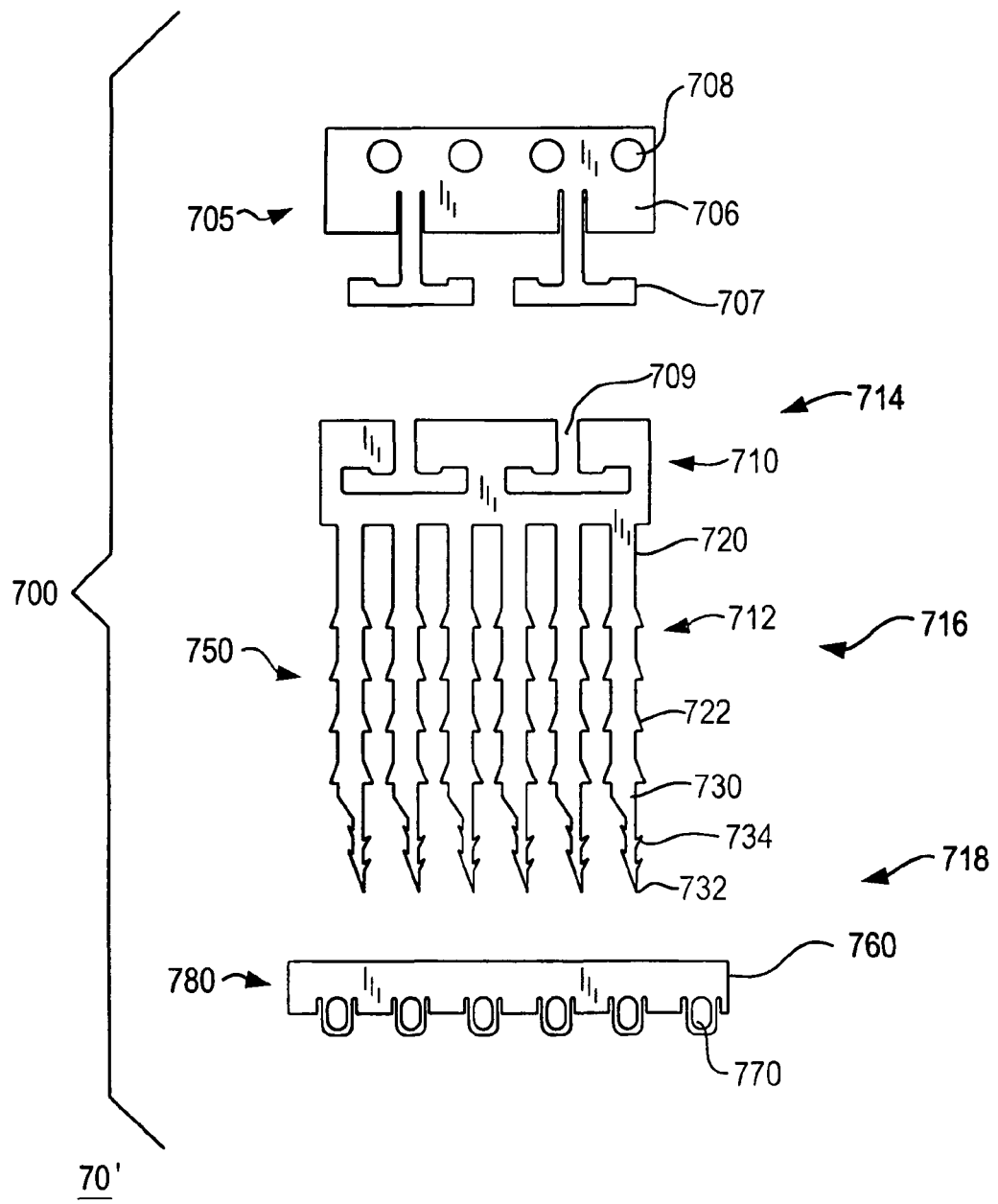
FIG. 49 is a planar development of an illustrative embodiment of a gathering and retaining device, in an unassembled state, constructed in accordance with the present invention.

As illustrated in FIGS. 49-58, device 700 may include a connector portion 705, a gathering portion 750, and a retaining portion 780. According to a preferred embodiment, device 700 has been illustrated as a single, integrated device (see, e.g., FIGS. 50-58). Device 700 preferably includes a plurality of fingers 712 to engage the tissue of the septum primum and the septum secundum about the PFO lumen and a retention slide 780 to gather and hold it together in a reduced area to effectively close the lumen. FIG. 49 shows a planar development of what is actually, preferably, three individually integral, one-piece (unitary), annular, portions of device 700. In particular, the left and right edges of each of the three structures shown in FIG. 49 are actually, preferably, joined to and integral with one another, and each of the three structures are intercoupled with one another. Thus, the actual structure of device 700 is as shown in FIGS. 50-58, although FIG. 49 is useful to more clearly reveal certain details of various features of device 700. A central longitudinal axis 702 about which device 700 is annular is shown in FIGS. 50-56. Like devices 200 and 300, a particularly preferred material for device 700 is nitinol. Other examples of suitable materials include tantalum, cobalt chromium, Elgiloy®, Molybium®, tungsten, stainless steel, platinum, silicone, and polyurethane. It should be noted that, depending on the material of the device, different techniques may be used to shape the structure of device 700 shown in FIG. 49 into approximately the fully expanded geometry of FIGS. 50-52 that device 700 will assume after full assembly.

Connector portion 705 preferably includes an annular element 706 with a plurality of slots 708, which may be similar to slots 208 of device 200 (see, e.g., FIG. 11) for coupling device 700 to connector support member 124. Connector portion 705 also preferably includes one or more cross-bars or T-shaped bars 707 extending from annular element 706 for releasably coupling to gathering portion 750, as will be described in greater detail hereinbelow.

Gathering portion 750 preferably includes a plurality of fingers 712 to engage the tissue of the septum primum and the septum secundum about the PFO lumen. Gathering portion 750 of device 700 may be described as including an annular element 710 and a plurality of annularly spaced tissue gathering fingers 712 extending distally therefrom. According to one embodiment, gathering portion 750 includes six fingers 712. Gathering portion 750 may have fewer or more than six of fingers 712, depending on the type of defect to be closed, and the size and shape of the particular defect. Alternatively, the structure of gathering portion 750 may have different configurations of fingers and geometries.

Each gathering finger 712 preferably includes a medial extension member 720 and a distal member 730. Preferably one or more sets of notches or ratchet teeth 722 are provided along the length of medial extension members 720, such that retaining portion 780 may be retained thereabove or therebelow when positioned about gathering portion 750 of device 700, as described in more detail hereinbelow. Each distal member 730 may preferably include a distal tissue holding feature that in this case includes a barb-like free end portion 732 that is sharply pointed distally, and, preferably, at least one barb 734 proximal to free end portion 732. The dimensions of each medial member 720 and each distal member 730 of each finger 712 may be altered according to the type, size, and shape of the defect to be closed, and to the particular finger's orientation to the defect when deployed in the patient (e.g., whether the finger is to engage the septum primum, the septum secundum, or both).

Annular element 710 defines the proximal portion 714 of gathering portion 750, whereas medial extension members 720 and distal members 730 define the medial portion 716 and the distal portion 718 of gathering portion 750, respectively. Another difference between gathering device 200 described above and gathering portion 750 of device 700 is that there is preferably one or more bar-receiving slots 709 provided by portion 750 along annular element 710, such that bars 707 of connector portion 705 may be releasably coupled to gathering portion 750 by interacting with slots 709, as described in greater detail hereinbelow.

Figure 52:
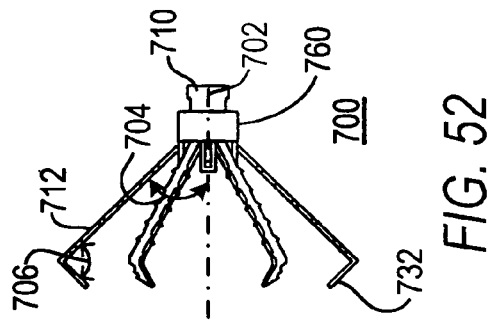
FIG. 52 is a side elevational view of the gathering and retaining device of FIGS. 49-51, taken from line 52-52 of FIG. 50.
Figure 54:
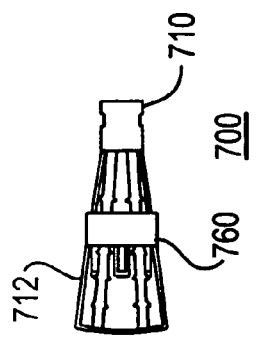
FIG. 54 is a side elevational view of the gathering and retaining device of FIGS. 49-53, taken from line 54-54 of FIG. 53.
Figure 51:
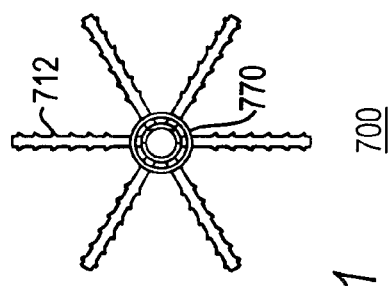
FIG. 51 is a top elevational view of the gathering and retaining device of FIGS. 49 and 50, taken from line 51-51 of FIG. 50.
Figure 50:
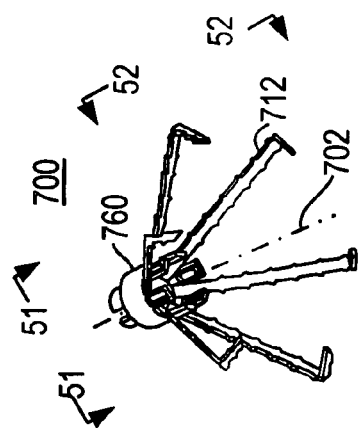
FIG. 50 is a perspective view of the gathering and retaining device of FIG. 49, in an assembled state, in an expanded configuration, in accordance with the present invention.
Figure 53:
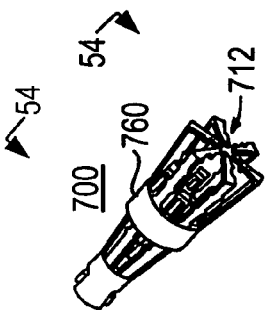
FIG. 53 is a perspective view of the gathering and retaining device of FIGS. 49-52, in an assembled state, in a constricted configuration, in accordance with the present invention.

In the fully expanded configuration of gathering portion 750 of device 700 shown in FIGS. 50-52, the medial extension member 720 of each finger 712 may extend radially out from annular element 710 at an angle 704 to longitudinal axis 702. Moreover, as shown in FIGS. 50-52, the distal member 730 of each finger 712 may be oriented with respect to medial extension member 720 at an angle 706. Like the dimensions of each medial member 720 and each distal member 730 of each finger 712, orientation angles 704 and 706 may be altered according to the type, size, and shape of the defect to be closed, and to the particular finger's orientation to the defect when deployed in the patient.

Device 700 may also include a retaining portion 780, as shown in isolation in FIG. 49. Retaining portion 780 may be slideably coupled to gathering portion 750 about fingers 712, as will be described in greater detail hereinbelow and as shown in FIGS. 50-58, to restrict fingers 712 in a constricted configuration. Retaining portion 780 preferably includes an annular element 760 that is similarly shaped, but slightly larger than annular element 710, and a plurality of slots or loops 770 that preferably bend out of the plane of element 760, such that each slot may slide either between two adjacent fingers 712 or about one of fingers 712, for example. Slots 770 allow retaining portion 780 to be slideably coupled to annular gathering portion 750 axially along axis 702, as shown in FIGS. 50-58.

Figure 55:
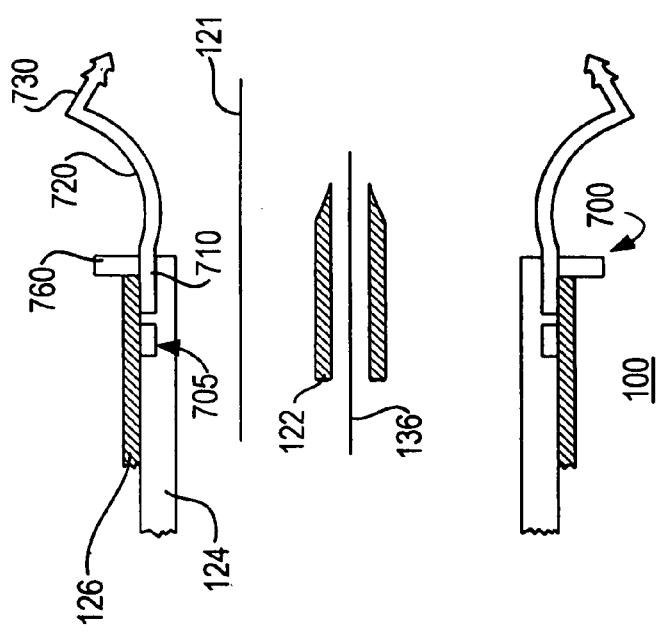
FIG. 55 is a cross-sectional view of the apparatus of FIGS. 11-17, but in conjunction with the gathering and retaining device of FIGS. 49-54, in the early stage of the procedure of FIG. 11, in accordance with the present invention.
Figure 58:
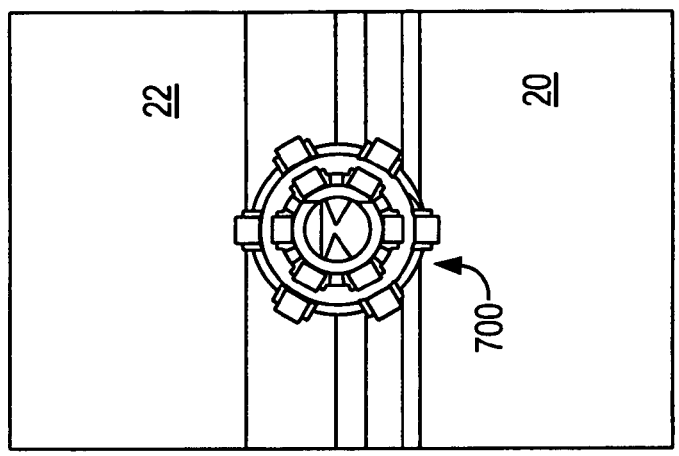
FIG. 58 is a front elevational view of the secured portion of the heart of FIG. 57, taken from line 58-58 of FIG. 57, but with some tissue of the secured portion omitted.
Figure 57:
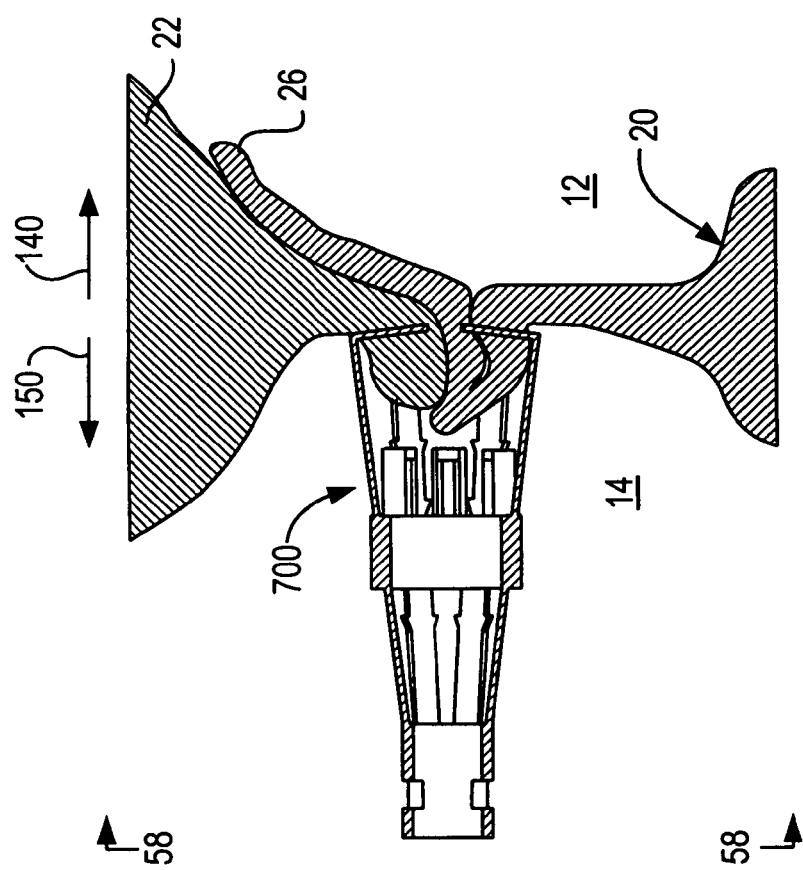
FIG. 57 is a cross-sectional view, similar to FIG. 1B, of the gathered portion of the heart of FIG. 1A secured by the gathering and retaining device of FIGS. 49-56, in accordance with the present invention.

In closing a septal defect using device 700, no separate retaining device like device 300 is required. As shown in FIG. 55, annular element 710 of gathering portion 750 is preferably positioned annularly about support member 124, similarly to gathering device 200, as described hereinabove. Support member 126 may be positioned about bars 707 and slots 709, such that these elements are forced to interlock and portions 705 and 750 remain coupled. Support member 126 preferably also abuts the proximal end of annular element 760 of retaining portion 750 for assisting in deploying device 700 in the patient.

Figure 56:
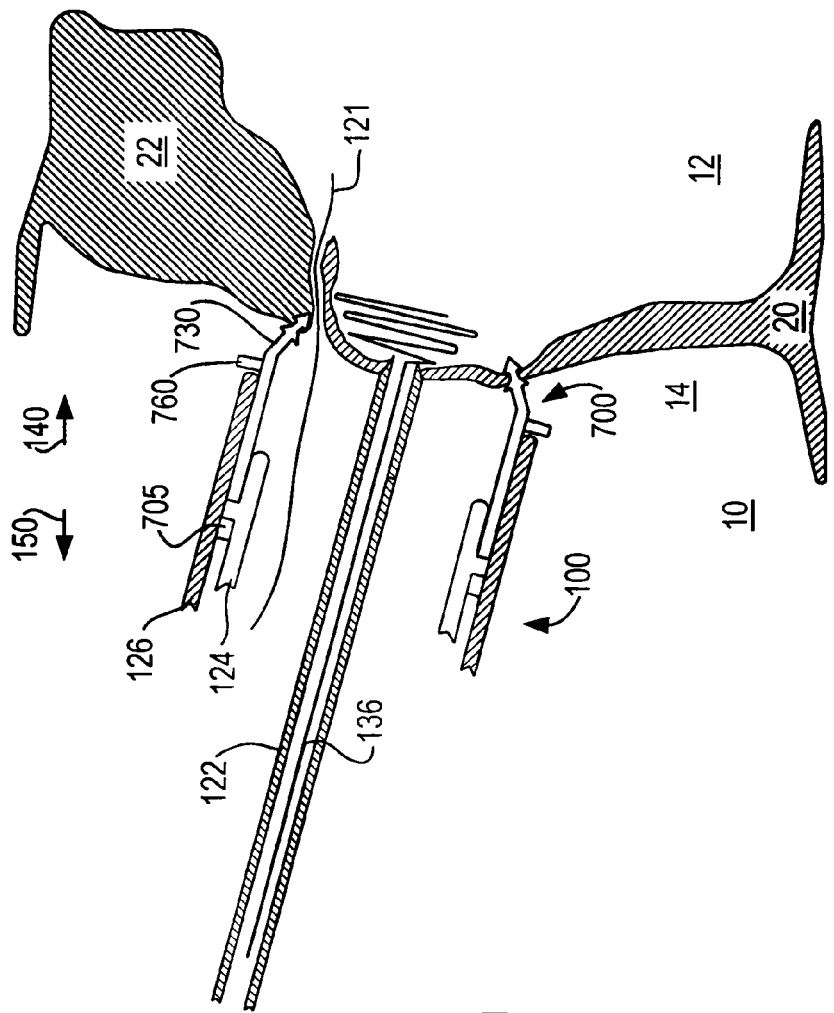
FIG. 56 is a cross-sectional view of a portion of the heart of FIG. 1, illustrated with the gathering and retaining device, and apparatus of FIG. 55, in the fifth stage of a procedure of FIG. 17, in accordance with the present invention.

As shown in FIG. 56, once fingers 712 of gathering device 700 have been advanced distally in the direction of arrow 140 to engage septal tissue, similarly to fingers 212 of device 200 (see, e.g., FIG. 15), and preferably once an apposition mechanism (e.g., mechanism 132) has been retracted proximally in the direction of arrow 150 to provide positive tissue apposition from the left atrium, such that tissue from the septum primum and tissue from the septum secundum preferably reside close together within the fingers 712 of gathering device 700, distal advancement of support member 126 with respect to support member 124 permits annular element 760 and slots 770 of retaining portion 780 to slide distally along fingers 712 and ratchet distally along notches 722 to retain fingers 712 in its constricted configuration about the gathered septal tissue. Free end portions 732 of fingers 712 preferably engage the periphery of the gathered tissue and retain the tissue therein.

The closure of the PFO using gathering device 700 is complete. Gathering portion 750 of device 700 may then preferably be detached from apparatus 100 by proximally retracting support member 126 in the direction of arrow 150 with respect to support member 124, such that bars 707 may deflect radially outward from annular element 706 of connector portion 705 beyond slots 709 (or vice versa), thereby releasing portion 750 from apparatus 100. Apparatus 100 is subsequently removed from the operative site and gathering portion 750 and retaining portion 780 of device 700 is left in the patient for closure of the PFO (see, e.g., FIGS. 57 and 58).

Yet another alternative embodiment of the gathering and retaining devices in accordance with the invention is described herein. The apparatus and procedures are substantially identical to those described above with respect to FIGS. 1-17 and 49-58, with the substantial differences described hereinbelow with respect to FIGS. 59-61.

Figure 59:
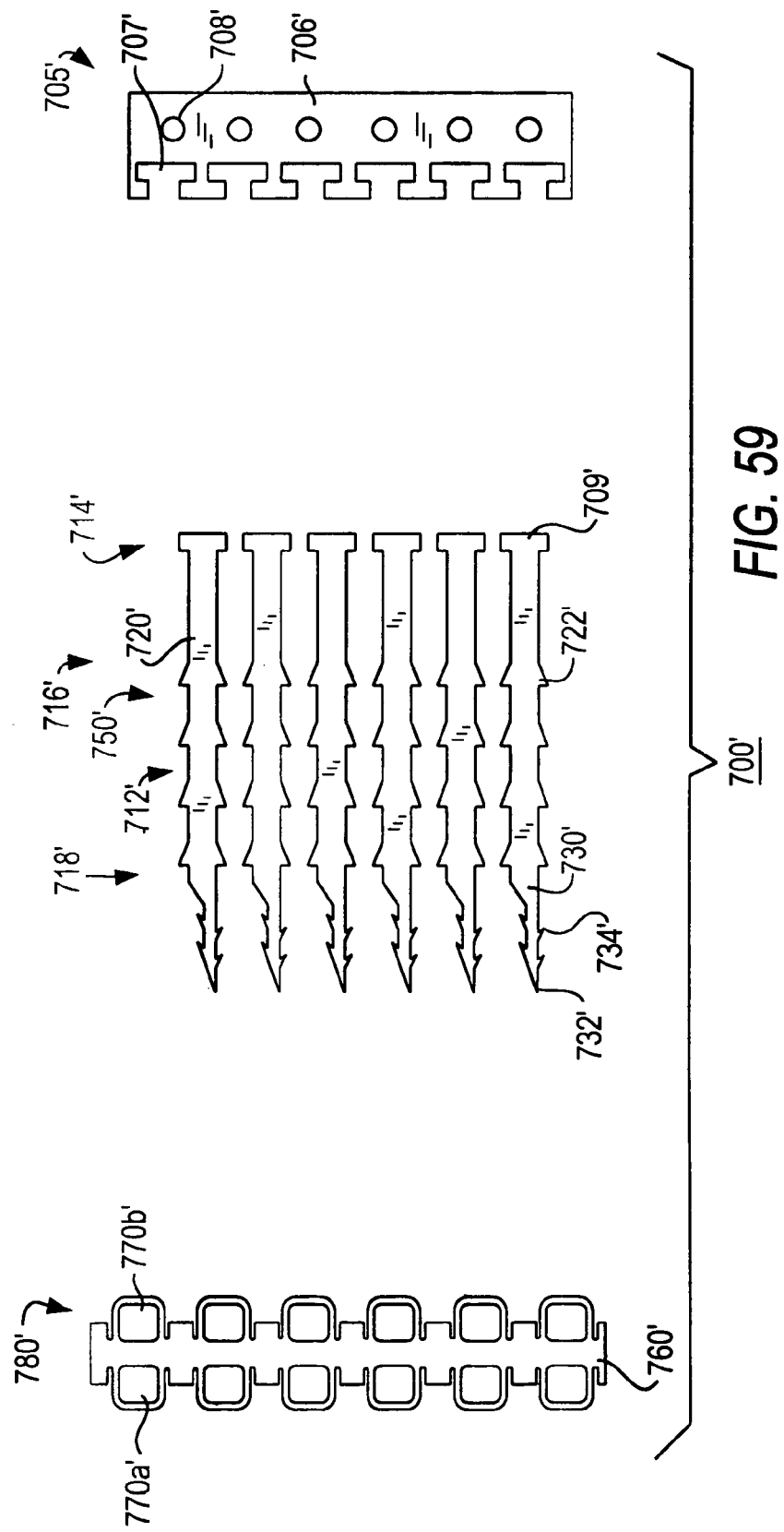
FIG. 59 is a planar development of another illustrative embodiment of a gathering and retaining device, in an unassembled state, constructed in accordance with the present invention.
Figure 61:
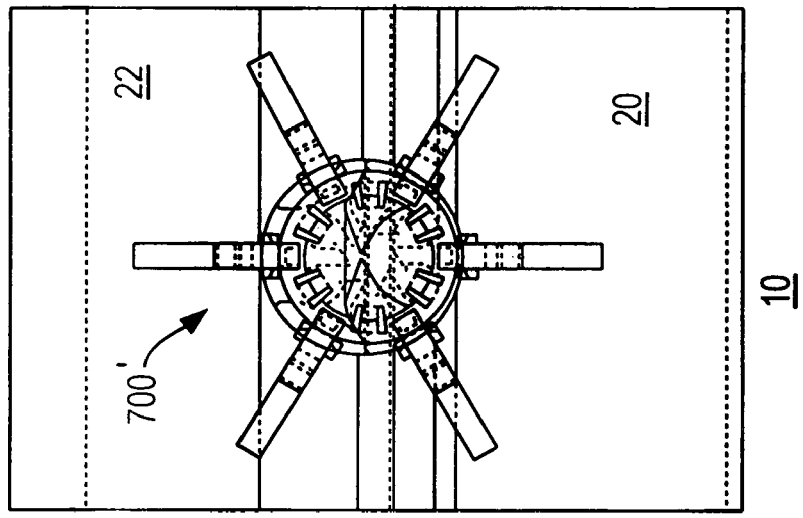
FIG. 61 is a front elevational view of the secured portion of the heart of FIG. 60, taken from line 61-61 of FIG. 60, but with some tissue of the secured portion omitted.
Figure 60:
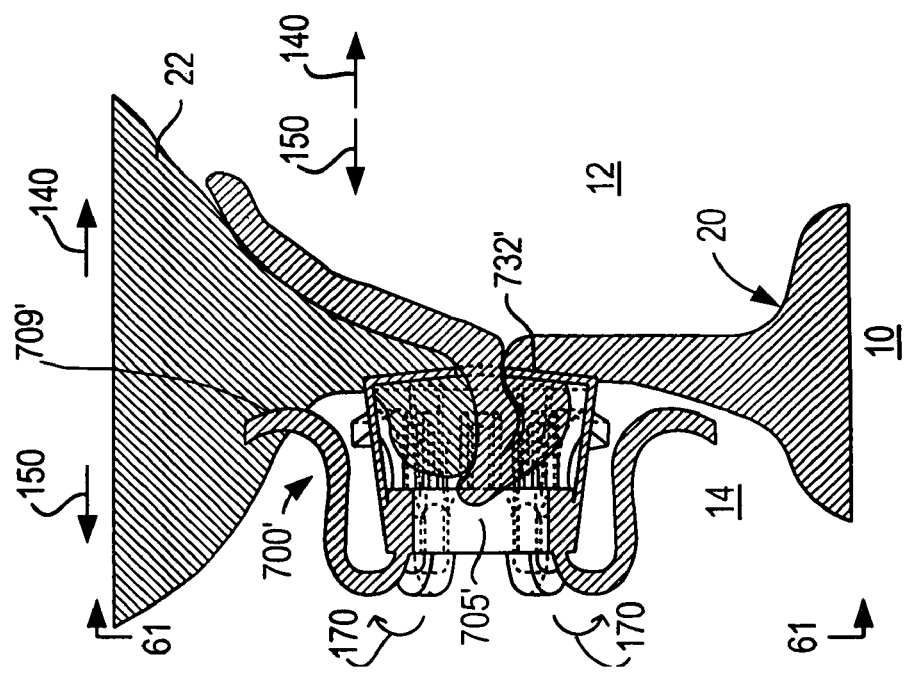
FIG. 60 is a cross-sectional view, similar to FIG. 1B, of the gathered portion of the heart of FIG. 1A secured by the gathering and retaining device of FIG. 59, in accordance with the present invention.

As illustrated in FIG. 59, device 700' may be substantially similar to device 700 described above with respect to FIGS. 49-58, and may include a connector portion 705', a gathering portion 750', and a retaining portion 780'. However, unlike device 700, device 700' preferably lacks the annular element uniting the gathering fingers at their proximal end As illustrated in FIGS. 59-61, the proximal end of each of fingers 712' terminates at its own cross-bar 709', as opposed to all of the fingers terminating at a common annular element (e.g., annular element 710 of device 700). Therefore, in this embodiment, fingers 712' are substantially independent elements. Furthermore, unlike connector portion 705, portion 705' of device 700' includes one or more slots 707' within annular element 706' for releasably coupling to each of the cross-bars 709' of the gathering portion 750', similarly to the interaction between bars 707 and slots 709 of device 700, as described hereinabove with respect to FIGS. 49-58. Finally, with respect to retaining portion 780', annular element 760' preferably includes two sets of slots or loops 770' (i.e., 770a' and 770b'), each running along a respective side of annular element 760'. Like slots 770, slots 770' preferably bend out of the plane of the annular element, such that a slot from each set may slide either between two adjacent fingers 712' or about one of fingers 712', for example. Slots 770' allow retaining portion 780' to be slideably coupled to annular gathering portion 750' axially along axis 702', as shown in FIGS. 60 and 61, in a relationship similar to that between portions 750 and 780.

Similarly to the deployment of device 700, described above with respect to FIGS. 50-58, distal advancement of particular support members permits annular element 760' and slots 770' of retaining portion 780' to slide distally along fingers 712' and selectively ratchet distally along notches 722' to retain fingers 712' in its desired constricted configuration about the gathered septal tissue (see, e.g., FIGS. 60 and 61). Free end portions 732' of fingers 712' preferably engage the periphery of the gathered tissue and retain the tissue therein.

The closure of the PFO using gathering device 700' is complete. Gathering portion 750' of device 700' may then preferably be detached from apparatus 100, similarly to the detachment of portion 750 from apparatus 100 as described hereinabove, by proximally retracting support members in the direction of arrow 150 such that bars 709' may deflect radially outward from annular element 706' of connector portion 705' beyond slots 707' (or vice versa), thereby releasing portion 750' from apparatus 100. Apparatus 100 is subsequently removed from the operative site and gathering portion 750' and retaining portion 780' of device 700' is left in the patient for closure of the PFO (see, e.g., FIGS. 57 and 58).

Unlike gathering portion 750, wherein each of fingers 712 are joined at its proximal end by annular element 710, each of fingers 712' is independent of each of the other fingers 712' at its proximal end. Therefore, when gathering portion 750' is released from connector portion 705' (and, thus, apparatus 100), the proximal end of each of fingers 712' preferably deflects distally in the direction of arrows 170. As shown in FIG. 60, this deflection of the proximal ends of fingers 712' thereby minimizes the distance that portion 750' extends from the right atrial wall into right atrium 14 of heart 10, and also, preferably, provides further anchoring of device 700' at the site of the PFO through the engagement of at least one of bars 709' with the right atrial wall.

It is to be understood, that there are multiple ways to retain a gathering device at the operative site for securing the gathered tissue and closing the defect besides those disclosed hereinabove without departing from the spirit and scope of the present invention. For example, a suture may be utilized to retain the gathering device in a constricted configuration that secures the gathered tissue. Alternatively, a distal end of a catheter tube surrounding the gathering device (e.g., support member 126) may be detached from the remainder of the apparatus and left at the operative site to retain the gathering device in a constricted configuration for securing the gathered tissue.

An alternative embodiment of the transeptal apposition mechanism in accordance with the invention is described herein. The apparatus and procedures are substantially identical to those described above with respect to FIGS. 1-17, with the substantial differences described hereinbelow with respect to FIGS. 62 and 63.

Figure 62:
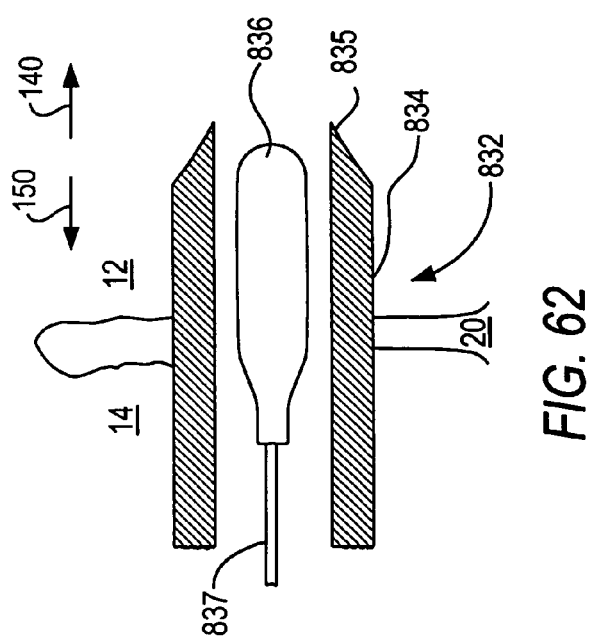
FIG. 62 is a cross-sectional view of a portion of the heart of FIG. 1, illustrated with another illustrative embodiment of an apposition mechanism, in a first stage of a procedure, constructed in accordance with the present invention.

As illustrated in FIG. 62, transeptal apposition mechanism 832 may include a distal piercing portion, such as cannula needle 834, having a sharpened distal tip 835, for penetrating the septum primum and passing therethrough from one atrium to the other, similar to needle 134. Transeptal apposition mechanism 832 preferably also includes an uninflated balloon 836 near the distal end of an axially movable balloon catheter 837 running within the hollow of needle 834, as shown in FIG. 62. The side wall of catheter tube 837 may include a separate lumen (not shown, but conventional for balloon catheters) through which pressurized inflation fluid may be supplied from a proximal region of the apparatus to balloon 836. Elements 836 and 837 may be slideable axially within needle 834, similarly to wire 136 within needle 134.

Like the distal end of wire 136 with respect to mechanism 132 described above, once tip 835 of needle 834 has passed through the tissue of the septum primum 20 and into the left atrium (see, e.g., FIG. 62), a physician may pass uninflated balloon 836 distally in the direction of arrow 140 through the distal end 835 of needle 834 and into the left atrium 12 of the patient.

Figure 63:
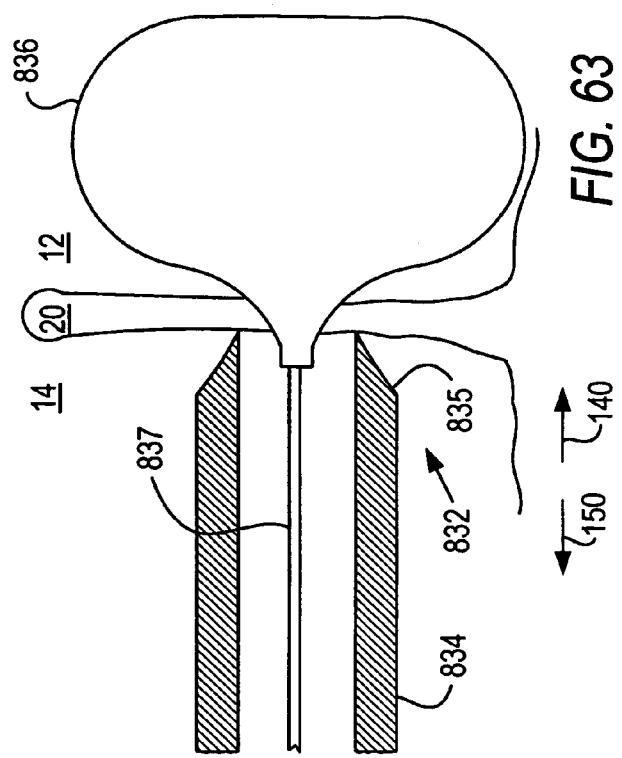
FIG. 63 is a cross-sectional view of the heart and apposition mechanism of FIG. 62, in a second stage of a procedure, in accordance with the present invention.

The next step in use of mechanism 832 is to inflate balloon 836, as shown in FIG. 63. The inflated balloon is preferably sized to a specific septal defect. Once inflated within the left atrium 12 of the patient, balloon 836 preferably is shaped such that it resists passage back proximally in the direction of arrow 150 through the septal tissue that has been penetrated by mechanism 832 and to provide positive apposition force to the tissue wall from the left atrium 12 when mechanism 832 is retracted proximally in the direction of arrow 150, as described above with respect to wire 136 of mechanism 132. The closure of the PFO may preferably be completed as described hereinabove or hereinbelow using any of the gathering devices and/or retaining devices of the present invention (e.g., devices 200 and 300).

Yet another alternative embodiment of the transeptal apposition mechanism in accordance with the invention is described herein. The apparatus and procedures are also substantially identical to those described above with respect to FIGS. 1-17, with the substantial differences described hereinbelow with respect to FIGS. 64 and 65.

As illustrated in FIGS. 64 and 65, transeptal apposition mechanism 932 may include a tissue holding structure, such as stylet 934, which pierces and retains tissue. As will be described in greater detail hereinbelow, the tissue holding structure 934 preferably includes a distal piercing portion, such as angled needle tip 935, similar in construction to a tip used, for example, in a hypodermic needle. The tissue holding structure 934 also preferably includes retention members, such as proximally extending barbs 936.

In the embodiment illustrated in FIGS. 64 and 65, the distal piercing portion 935 and the proximally extending barbs 936 are provided on a single, integrated unit, such as stylet 934. However, it is also contemplated that the distal piercing portion and the proximally extending barbs are provided on separate parts, as will be described in greater detail hereinbelow, with respect to FIGS. 66-68.

The stylet 934 is preferably mounted on a support shaft 937 for relative longitudinal motion with respect to devices 200 and 300 and their respective support members (not shown) in the distal and proximal directions of arrows 140 and 150, respectively.

Briefly, the stylet 934 is preferably constructed to pierce the tissue of the septum primum 20 with the needle tip 935 from the right atrial side of the PFO to the left atrial side of the PFO in the distal direction of arrow 140 (see, FIG. 64), similarly to needle 134. The stylet 934 is then preferably retracted proximally in the direction of arrow 150 to allow the barbs 936 to engage the exit side of the septum primum tissue 20 in the left atrium 12, such that the tissue that has just been pierced is now engaged by the barbs 936 in the left atrium (see, FIG. 65). By retracting support shaft 937 proximally in the direction of arrow 150, barbs 936 preferably resist passage back through the septal tissue that has been penetrated by mechanism 932 and provide positive apposition force to the tissue wall from the left atrium 12, as described above with respect to wire 136 of mechanism 132. The closure of the PFO may preferably be completed as described hereinabove or hereinbelow using any of the gathering devices and/or retaining devices of the present invention (e.g., devices 200 and 300).

Still another alternative embodiment of the transeptal apposition mechanism in accordance with the invention is described herein. The apparatus and procedures are also substantially identical to those described above with respect to FIGS. 1-17, 64, and 65, with the substantial differences described hereinbelow with respect to FIGS. 66-68.

Figure 66:
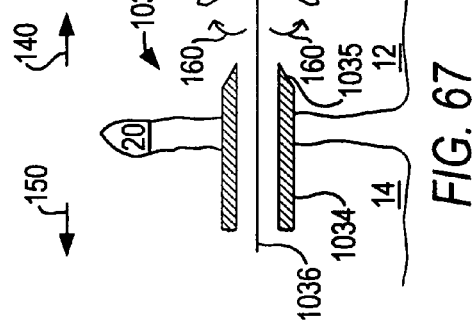
FIG. 66 is a cross-sectional view of a portion of the heart of FIG. 1, illustrated with still another illustrative embodiment of an apposition mechanism, in a first stage of a procedure, constructed in accordance with the present invention.
Figure 68:
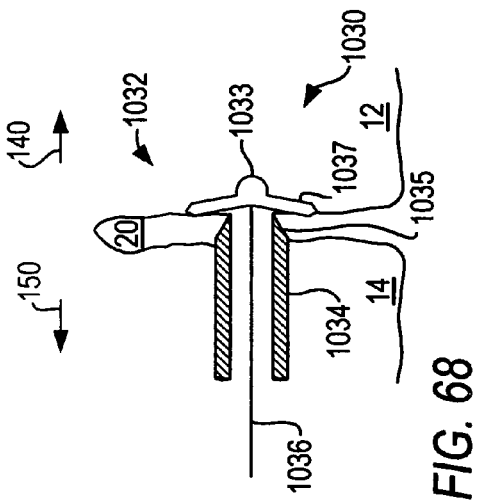
FIG. 68 is a cross-sectional view of the heart and apposition mechanism of FIGS. 66 and 67, in a third stage of a procedure, in accordance with the present invention.
Figure 67:
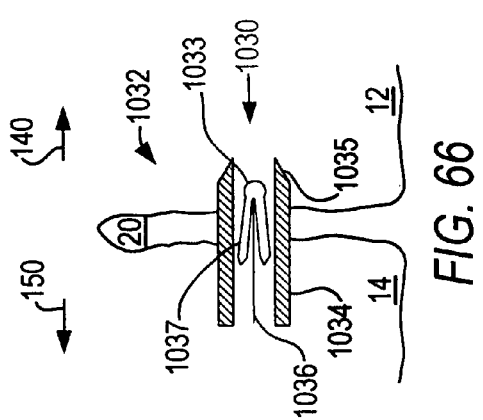
FIG. 67 is a cross-sectional view of the heart and apposition mechanism of FIG. 66, in a second stage of a procedure, in accordance with the present invention.

As illustrated in FIGS. 66-68, transeptal apposition mechanism 1032 may preferably include a distal piercing portion, such as cannula needle 1034, having a sharpened tip 1035, for advancing distally in the direction of arrow 140, for penetrating the septum primum 20, and for passing therethrough from the right atrium 14 to the left atrium 12 (see, e.g., FIG. 66), similarly to needle 134.

Transeptal apposition mechanism 1032 preferably also includes a barb support member 1030 disposed at the proximal end portion of a wire 1036. The barb support member 1030 is preferably provided with an atraumatic bulb tip 1033 that will not damage the interior wall of the heart. The barb support member 1030 is also preferably provided with a pair of proximal barbs 1037. Barbs 1037 may preferably be resilient, such that while inside the lumen of the cannula needle 1034, the barbs are disposed in a retracted configuration towards parallelism with the longitudinal axis of the apparatus. The barb support member 1030 is advanced distally into the left atrium 12 in the direction of arrow 140, whereupon the barbs 1037 may resiliently extend radially outwards, as indicated by the arrows 160 (see, FIG. 67).

The cannula needle 1034 and wire 1036 may be retracted proximally in the direction of arrow 150, such that the septal tissue that has just been pierced is now engaged by the barbs 1037 in the left atrium 12 (see, FIG. 68). By retracting needle 1034 and wire 1036 proximally, barbs 1037 preferably resist passage back through the tissue that has been penetrated by mechanism 1032 and provide positive apposition force to the tissue wall from the left atrium 12, as described above with respect to wire 136 of mechanism 132. The closure of the PFO may preferably be completed as described hereinabove or hereinbelow using any of the gathering devices and/or retaining devices of the present invention (e.g., devices 200 and 300).

Yet another alternative embodiment of the transeptal apposition mechanism in accordance with the invention is described herein. The apparatus and procedures are also substantially identical to those described above with respect to FIGS. 1-17 and 66-68, with the substantial differences described hereinbelow with respect to FIGS. 30-31D.

Figure 31D:
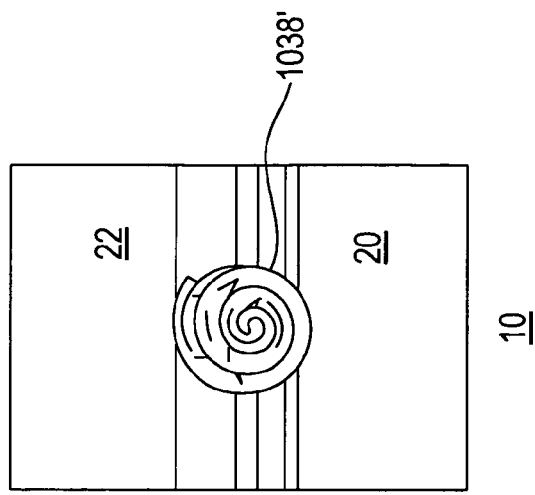
FIG. 31D is a front elevational view of the secured portion of the heart of FIG. 31C, taken from line 31D-31D of FIG. 31C, but with some tissue of the secured portion omitted.
Figure 31C:
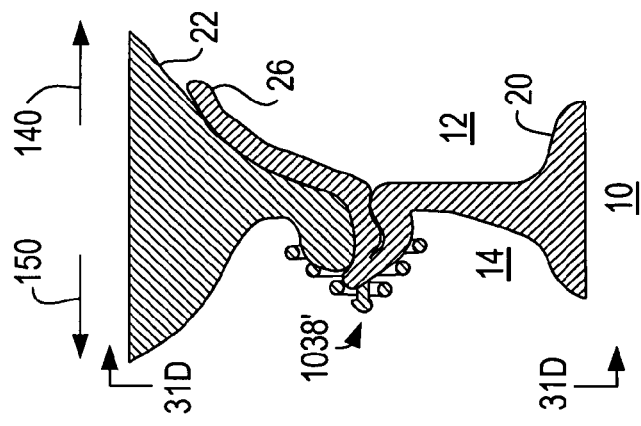
FIG. 31C is a cross-sectional view, similar to FIG. 1A, of the gathered portion of the heart of FIG. 1A secured by the apposition and retaining mechanism of FIGS. 30-31B, in accordance with the present invention.
Figure 30:
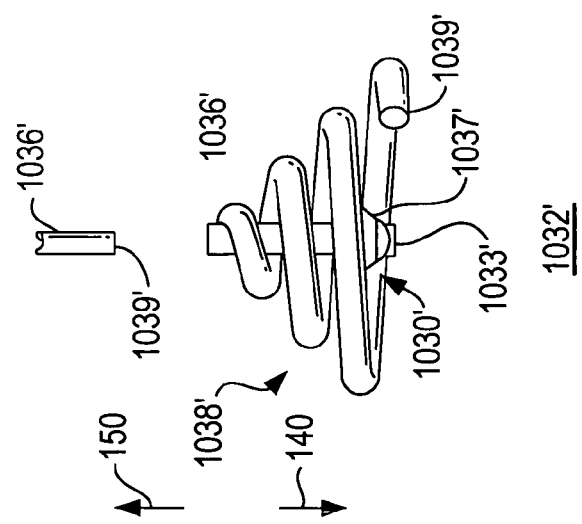
FIG. 30 is a side elevational view of another illustrative embodiment of an apposition and retaining mechanism constructed in accordance with the present invention.
Figure 31A:
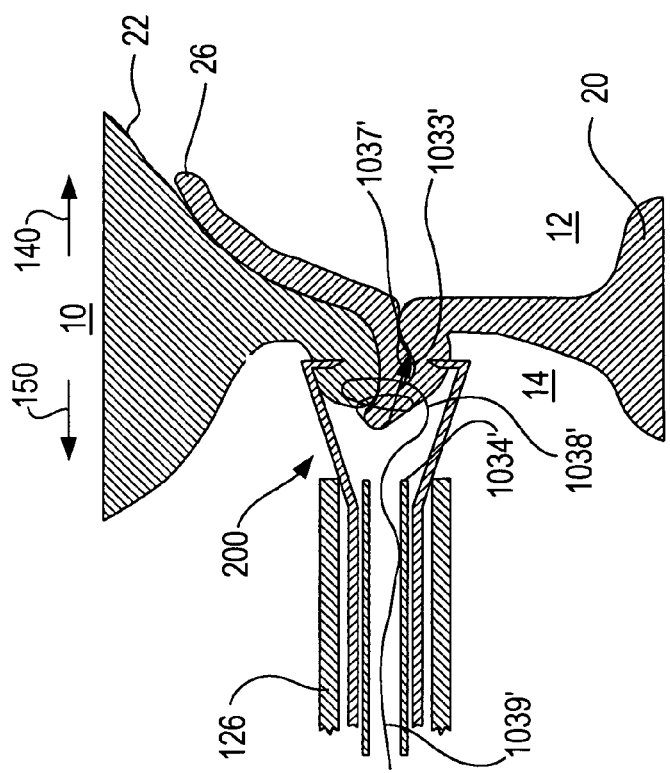
FIG. 31A is a cross-sectional view of a portion of the heart of FIG. 1, illustrated with the gathering device and apparatus of FIGS. 11-17, but in conjunction with the apposition and retaining mechanism of FIG. 30, in a first stage of a procedure, in accordance with the present invention.
Figure 31B:
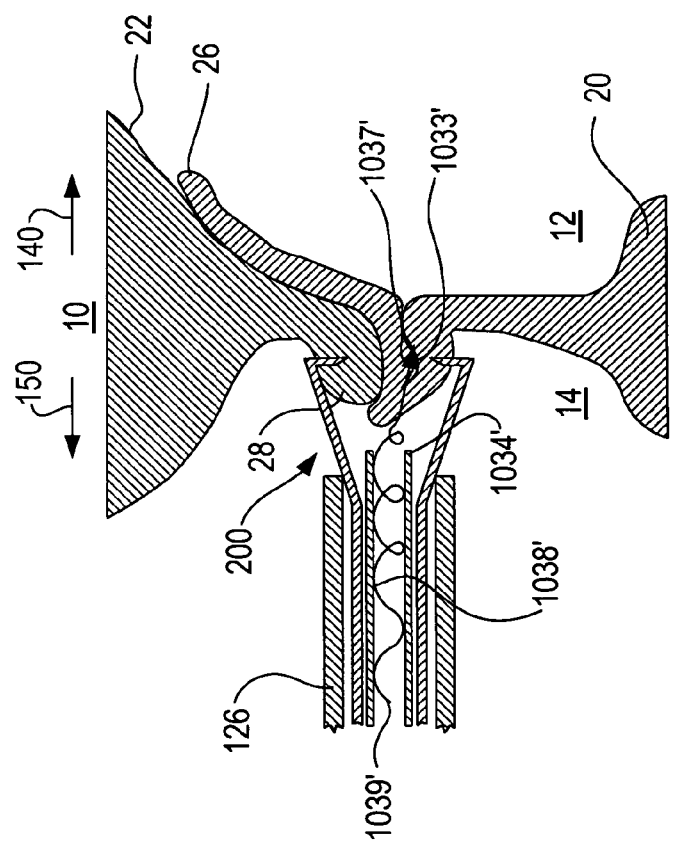
FIG. 31B is a cross-sectional view of the heart, gathering device, apparatus, and apposition and retaining mechanism of FIGS. 30 and 31A, in a second stage of a procedure, in accordance with the present invention.
Figure 35:
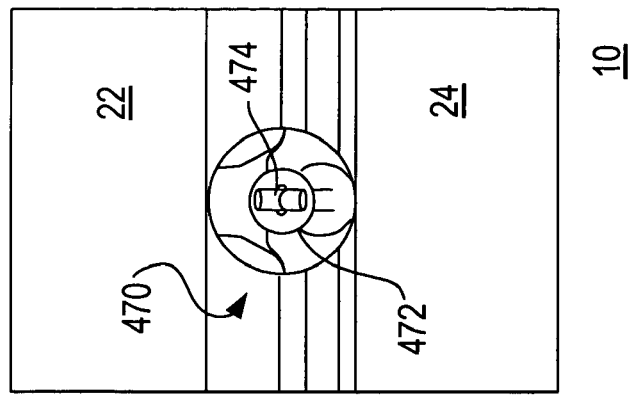
FIG. 35 is a front elevational view of the secured portion of the heart of FIG. 34, taken from line 35-35 of FIG. 34, but with some tissue of the secured portion omitted.
Figure 34:
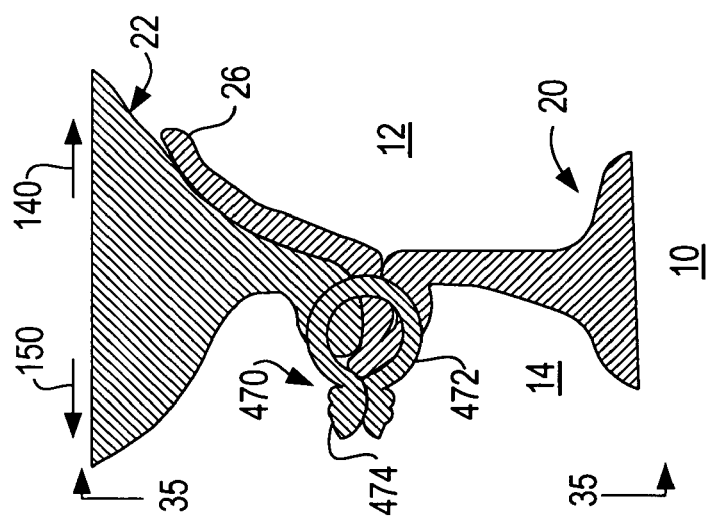
FIG. 34 is a cross-sectional view, similar to FIG. 1A, of the gathered portion of the heart of FIG. 1A secured by the retaining device of FIGS. 32 and 33, in accordance with the present invention.
Figure 32:
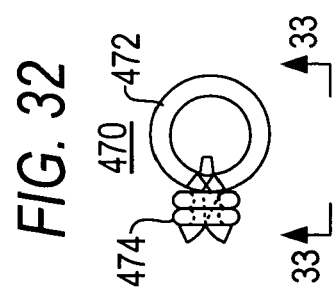
FIG. 32 is a top elevational view of the structure of still another illustrative embodiment of a retaining device constructed in accordance with the present invention.
Figure 33:
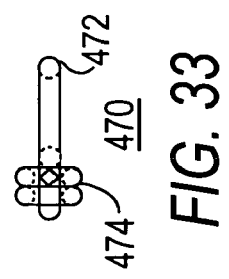
FIG. 33 is a side elevational view of the retaining device of FIG. 32, taken from line 33-33 of FIG. 32.
Figure 39:
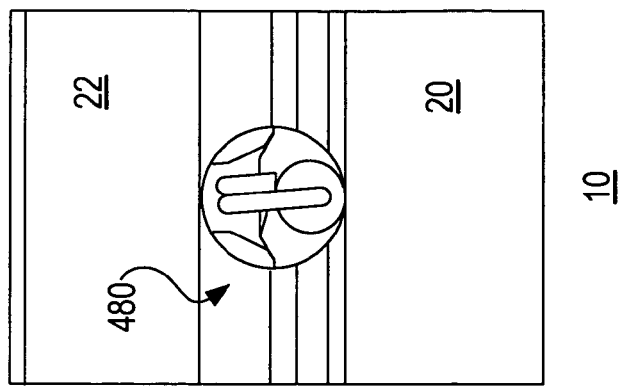
FIG. 39 is a front elevational view of the secured portion of the heart of FIG. 38, taken from line 39-39 of FIG. 38, but with some tissue of the secured portion omitted.
Figure 38:
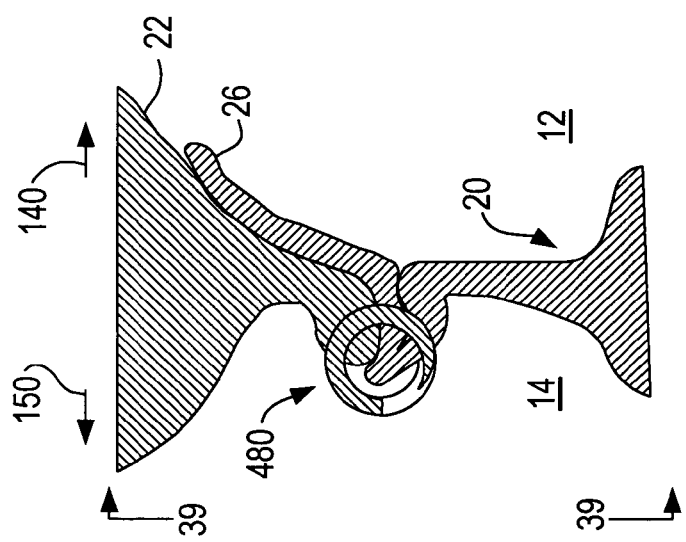
FIG. 38 is a cross-sectional view, similar to FIG. 1A, of the gathered portion of the heart of FIG. 1A secured by the retaining device of FIGS. 36 and 37, in accordance with the present invention.
Figure 36:
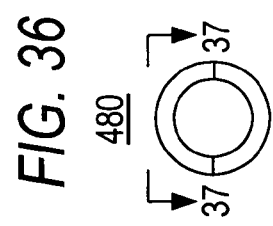
FIG. 36 is a top elevational view of the structure of yet another illustrative embodiment of a retaining device constructed in accordance with the present invention.
Figure 37:
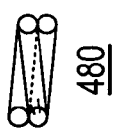
FIG. 37 is a side elevational view of the retaining device of FIG. 36, taken from line 37-37 of FIG. 36.

As illustrated in FIGS. 30-31D, transeptal apposition mechanism 1032' may be substantially similar to mechanism 1032 described above with respect to FIGS. 66-68, and may include a cannula needle 1034', a barb support member 1030' disposed at the proximal end portion of a wire 1036' with an atraumatic bulb tip 1033' and a pair of proximal barbs 1037'. However, unlike mechanism 1032, mechanism 1032' preferably includes structure that may secure tissue from the right atrial side of the defect without a separate securing device.

As illustrated in FIG. 30, wire 1036' may have a frangible point 1039' proximal to barb support member 1030' that may be released from the remainder of wire 1036', as will be described in greater detail hereinbelow with respect to FIGS. 30-31D. Segment 1038' of wire 1036' between barb support member 1030' and frangible point 1039' is preferably made of memory-shaped metal, such that, as it passes distally out of sharpened tip 1035' of needle 1034', it deflects more and more distally away from tip 1035' towards barb support member 1030' in a helical shape.

Similarly to mechanism 1032, cannula needle 1034' and wire 1036' may be retracted proximally in the direction of arrow 150, such that the septal tissue that has been pierced is now engaged by the barbs 1037' in the left atrium 12. By retracting needle 1034' and wire 1036' proximally, barbs 1037' preferably resist passage back through the tissue that has been penetrated by mechanism 1032' and provide positive apposition force to the tissue wall from the left atrium 12, as described above with respect to wire 136 of mechanism 132.

As shown in FIGS. 31A-31D, by further retracting needle 1034' proximally in the direction of arrow 150 with respect to wire 1036', segment 1038' may deflect more and more distally away from tip 1035' towards barb support member 1030' in a helical shape about the apposed tissue in right atrium 14. This apposed tissue may have already been gathered by a gathering device of the present invention described hereinabove or hereinbelow (e.g., device 200), although use of such a gathering device is not necessary for mechanism 1032' to deflect about the apposed tissue. Preferably, once some of the apposed tissue has been surrounded by the already-deflected portion of segment 1038', frangible point 1039' may be released from the remainder of wire 1036', thereby allowing all of segment 1038' to deflect in the helical shape about the apposed tissue (see, e.g., FIGS. 31C and 31D). The force provided by the helical shape of wire segment 1038' at both the left and right atrial sides of the PFO preferably secures the tissue gathered therein. While a "helical" shape is described in this preferred embodiment, it is to be understood that segment 1038' of wire 1036' may take any form once it is passed through the distal end of needle 1034', such that it may gather and/or secure apposed tissue of both the septum primum 20 and septum secundum 22 and remain in the patient at the operative site.

Once segment 1038' is released from the remainder of wire 1036', needle 1034', and the rest of the apparatus (including the gathering device, if used) may be removed from the patient, leaving segment 1038' to secure the gathered tissue for closing the defect. While this preferred embodiment of transeptal apposition mechanism 1032' may be utilized to appose, gather, and secure the tissue about the defect for its closure, it is to be understood that any of the gathering and/or securing devices of the present invention described hereinabove or hereinbelow may be used in conjunction with mechanism 1032' to aid in the closure of the defect. Moreover, it is to be understood that any of the apposition mechanisms of the present invention described hereinabove or hereinbelow may be configured similarly to mechanism 1032' for gathering and securing the apposed tissue.

Still another alternative embodiment of an apposition mechanism in accordance with the invention is described herein. The apparatus and procedures are also substantially identical to those described above with respect to FIGS. 1-17, with the substantial differences described hereinbelow with respect to FIGS. 69 and 70.

Figure 69:
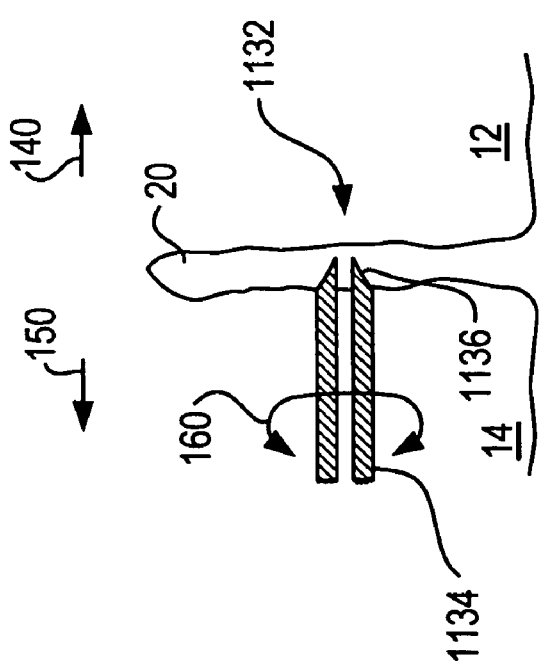
FIG. 69 is a cross-sectional view of a portion of the heart of FIG. 1, illustrated with yet another illustrative embodiment of an apposition mechanism, in a first stage of a procedure, constructed in accordance with the present invention.
Figure 70:
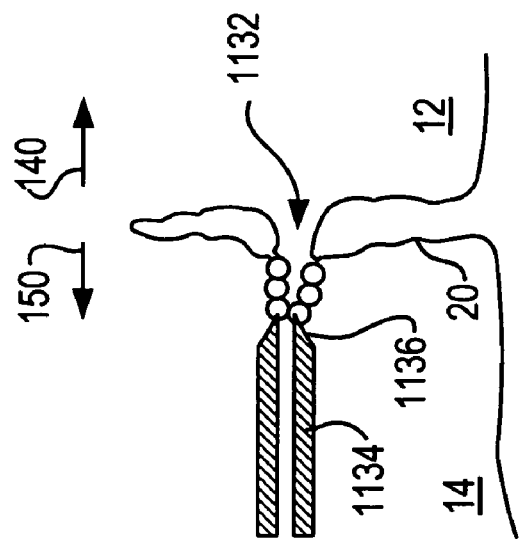
FIG. 70 is a cross-sectional view of the heart and apposition mechanism of FIG. 69, in a second stage of a procedure, in accordance with the present invention.

As illustrated in FIGS. 69 and 70, apposition mechanism 1132 may include a distal piercing portion, such as cannula needle 1134, having a sharpened tip 1136, for advancing distally in the direction of arrow 140, for penetrating the septum primum 20 (see, e.g., FIG. 69), similarly to needle 134. However, in this embodiment the cannula needle preferably only penetrates partially into the tissue of the septum primum 20 and does not pass all the way through from the right atrium 14 and into the left atrium 12.

Once needle 1134 has partially penetrated the septum tissue with sharpened tip 1136, mechanism 1132 may preferably be rotated in either the clock-wise or counter-clockwise direction of arrow 160, which is substantially perpendicular to the septal wall. This rotation preferably twists the wall of the septum primum 20 and pulls loose tissue of the septal wall into a tight bundle (see, e.g., FIG. 70), which may be further pulled proximally in the direction of arrow 150 and then gathered and secured using any of the gathering devices and/or retaining devices of the present invention described hereinabove or hereinbelow (e.g., devices 200 and 300).

Yet another alternative embodiment of an apposition mechanism in accordance with the invention is described herein. The apparatus and procedures are also substantially identical to those described above with respect to FIGS. 1-17, with the substantial differences described hereinbelow with respect to FIGS. 71-73.

Figure 71:
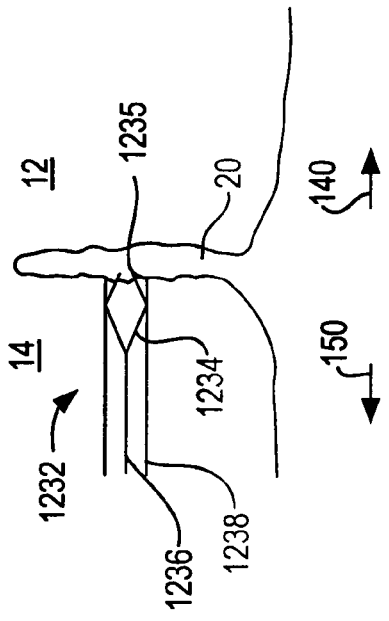
FIG. 71 is a cross-sectional view of a portion of the heart of FIG. 1, illustrated with still another illustrative embodiment of an apposition mechanism, in a first stage of a procedure, constructed in accordance with the present invention.
Figure 72:
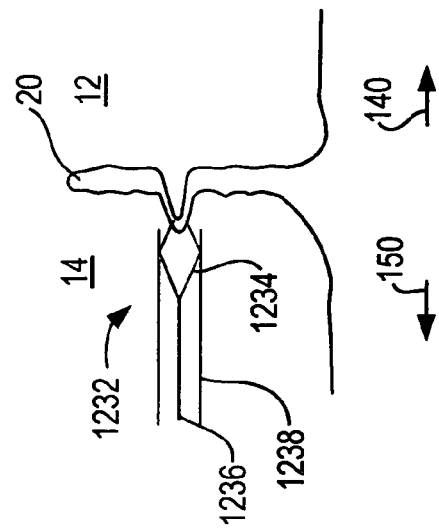
FIG. 72 is a cross-sectional view of the heart and apposition mechanism of FIG. 71, in a second stage of a procedure, in accordance with the present invention.
Figure 73:
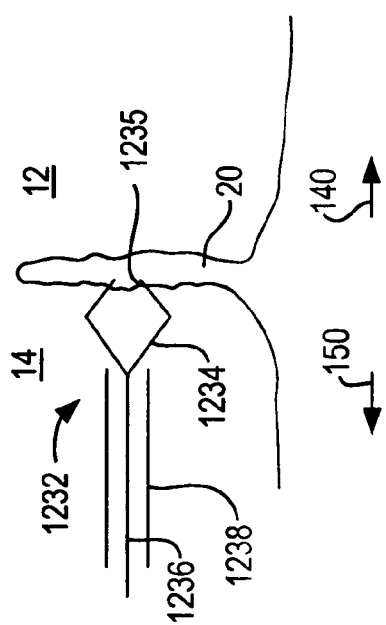
FIG. 73 is a cross-sectional view of the heart and apposition mechanism of FIGS. 71 and 72, in a third stage of a procedure, in accordance with the present invention.

As illustrated in FIGS. 71-73, apposition mechanism 1232 may include a grabbing device, such as two or more expandable jaws 1234, having sharpened tips 1235. This grabbing device may preferably be mounted on the distal end of a support member 1236, for advancing distally in the direction of arrow 140, for partially penetrating the septum primum 20 (see, e.g., FIG. 71). Mechanism 1232 preferably also includes support member 1238 concentrically surrounding support member 1236.

Once jaws 1234 have partially penetrated the septum tissue with sharpened tips 1235, mechanism 1232 may preferably advance support member 1238 distally in the direction of arrow 140 with respect to support member 1236 and its grabbing device. This distal advancement of support member 1238 preferably constricts the distance between tips 1235 of jaws 1234, such that tissue of the septum primum 20 may be held tightly therebetween (see, e.g., FIG. 72).

Then, support members 1236 and 1238 may together be retracted proximally in the direction of arrow 150, such that loose tissue of the septal wall may be pulled proximally (see, e.g., FIG. 73) and then gathered and secured using any of the gathering devices and/or retaining devices of the present invention described hereinabove or hereinbelow (e.g., devices 200 and 300).

An alternative embodiment of a guide wire mechanism in accordance with the invention is described herein. The apparatus and procedures are also substantially identical to those described above with respect to FIGS. 1-17, with the substantial differences described hereinbelow with respect to FIGS. 74-76.

As illustrated in FIGS. 74-76, apparatus 100 may further include orienting device 1300 coupled to the distal end of additional support member 123 that may preferably be advanced and retracted along guide wire 121. Device 1300 preferably includes a proximal end 1310, a distal end 1330, and a pair of "V-shaped" wings 1320 extending therebetween. Distal end 1330 may be advanced distally in the direction of arrow 140 along guide wire 121 with respect to proximal end 1310, such that angle 1324 formed at joint 1322 of each wing 1320 may increase, thereby reducing distance 1326 between joints 1322 and thereby bringing wings 1320 into parallel with, and closer proximity to, guide wire 121. This is be referred to herein as the constricted configuration of device 1300. Likewise, distal end 1330 may be retracted proximally in the direction of arrow 150 along guide wire 121 with respect to proximal end 1310, such that angle 1324 of each wing 1320 may decrease, thereby increasing distance 1326 and thereby bending wings 1320 farther away from guide wire 121. This expanded configuration of device 1300 is shown in FIG. 74, for example. This expansion and constriction of wings 1320 may preferably be accomplished by passing a catheter tube about device 1300, similarly to the expansion and constriction of fingers 212 with respect to the movement of support member 126 (see, e.g., FIGS. 11 and 12). The expansion and constriction of wings 1320 preferably allows device 1300 to orient itself in the flat lumen of the PFO, as will be described in greater detail hereinbelow.

Once guide wire 121 has been advanced through the lumen of PFO 24 and into left atrium 12 of the patient, orienting device 1300 (preferably in its constricted configuration) may be advanced distally in the direction of arrow 140 along guide wire 121, preferably such that substantially the entire length of wings 1320 between end portions 1310 and 1330 of device 1300 lie within the lumen of the PFO. Once substantially within the lumen of the PFO, wings 1320 are preferably expanded (see, e.g., FIG. 75), although, alternatively, wings 1320 may be expanded as device 1300 is advanced into the lumen.

This expansion of device 1300 within the lumen of the PFO preferably orients both wings 1320 in the plane of the lumen of the PFO to hold the tissue of the lumen taught. Preferably, by orienting device 1300 with respect to the plane of the lumen, the remainder of apparatus 100 (e.g., transeptal apposition mechanism 132, gathering device 200, retaining device 300, etc.) may also be oriented with respect to the plane of the PFO lumen, such that the closure devices may be deployed at desired angles with respect to the septal walls at the operative site. For example, as shown in FIG. 76, once device 1300 has been expanded to preferably orient apparatus 100 with respect to PFO 24, needle 134 of mechanism 132 may preferably be biased to be deployed at a desired angle 1334 with respect to device 1300 and guide wire 121 for penetration of septum primum 20.

Once device 1300 has been expanded in the lumen of PFO 24, thereby orienting the remainder of apparatus 100 with the operative site, device 1300 may preferably be constricted and removed from the lumen of PFO 24, such that the remainder of apparatus 100 may be deployed in any of the ways described hereinabove to close the lumen of PFO 24.

Another alternative embodiment of a guide wire mechanism in accordance with the invention is described herein. The apparatus and procedures are also substantially identical to those described above with respect to FIGS. 1-17 and 74-76, with the substantial differences described hereinbelow with respect to FIGS. 77-79.

Figure 79:
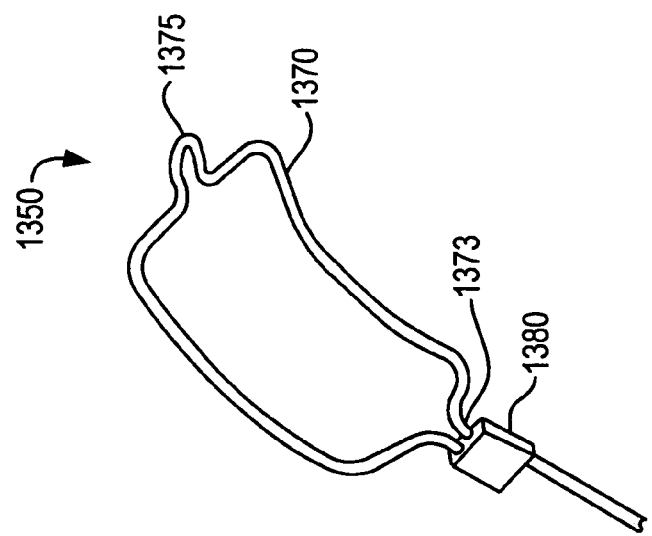
FIG. 79 is a perspective view of the guide wire mechanism of FIGS. 77 and 78.
Figure 78:
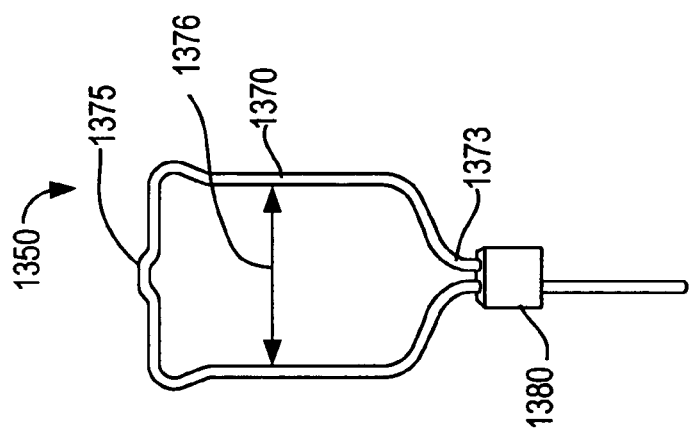
FIG. 78 is a front elevational view of the guide wire mechanism of FIG. 77, taken from line 78-78 of FIG. 77.
Figure 77:
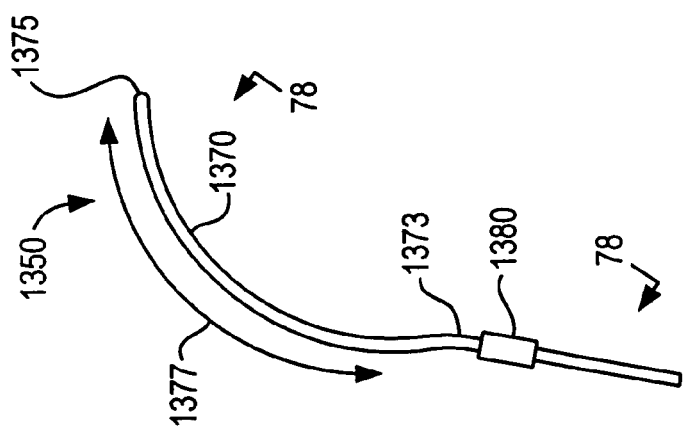
FIG. 77 is a side elevational view of another guide wire mechanism, in an expanded configuration, constructed in accordance with the present invention.

As illustrated in FIGS. 77-79, device 1350 may be substantially similar in function to device 1300, described hereinabove with respect to FIGS. 74-76, which may be coupled to the distal end of an additional support member and preferably advanced and retracted along a guide wire. Device 1350 preferably includes a centerizing portion 1370 with a pair of side members 1374 extending from a common distal end 1375 to a securing element 1380 at a proximal point 1373. Portion 1370 may preferably be made of a wire or other suitable material that has enough structural rigidity to hold its shape in a proper orientation in the PFO lumen to hold the tissue of the lumen taught.

Similarly to device 1300, distal end 1375 of device 1350 may be advanced distally along a guide wire with respect to proximal point 1373, such that side members 1374 may constrict closer to one another, thereby minimizing distance 1376. This is to be referred to herein as the constricted configuration of device 1350. Likewise, distal end 1375 may be retracted proximally along the guide wire with respect to proximal point 1373, such that side members 1374 expand away from one another, thereby increasing distance 1376. This expanded configuration of device 1350 is shown in FIGS. 77-79, for example. Preferably, in its expanded configuration, device 1350 is shaped with a curve 1377 to match the lumen shape of the PFO (see, e.g., FIG. 77). Similarly to device 1300, this expansion and constriction of device 1350 may preferably be accomplished by passing a catheter tube about device 1350. The expansion and constriction of portion 1370 preferably allows device 1350 to orient itself in the lumen of the PFO, similarly to device 1300.

Although the apparatus and methods of the present invention have been described hereinabove with respect to closing the lumen of a patent foramen ovale, they can also be used for preventing the flow of body fluids through holes in body cavity walls and lumens in a patient's body tubing, as well as for simply gathering and reducing the area of wall tissue in a patient's body, without departing from the spirit and scope of the present invention.

Figure 80:
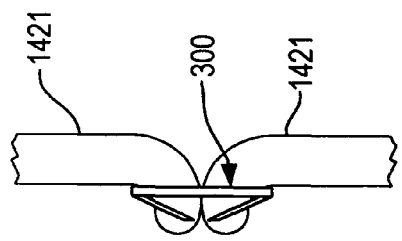
FIG. 80 is a cross-sectional view of a hole in a body cavity wall.
Figure 82:
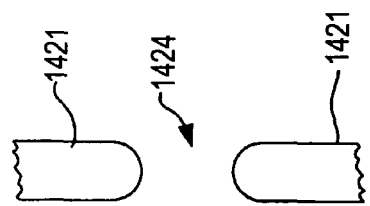
FIG. 82 is a cross-sectional view of a lumen in a body tubing.
Figure 81:
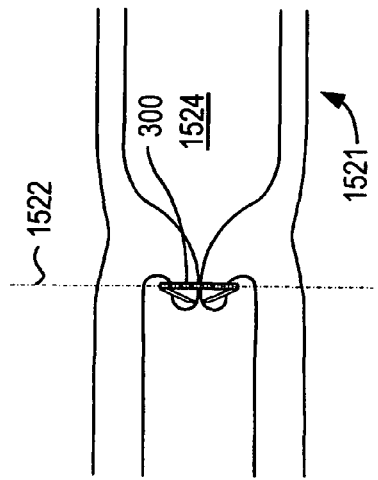
FIG. 81 is a cross-sectional view, similar to FIG. 80, of a gathered portion of the wall of FIG. 80 secured by the retaining device of FIGS. 7-12A, in accordance with the present invention.
Figure 86:
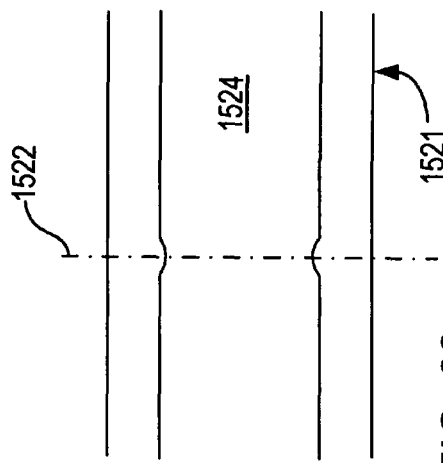
FIG. 86 is a cross-sectional view, similar to FIG. 82, of a gathered portion of the body tubing of FIGS. 82-85 secured by the retaining device of FIGS. 7-12A, in accordance with the present invention.
Figure 83:
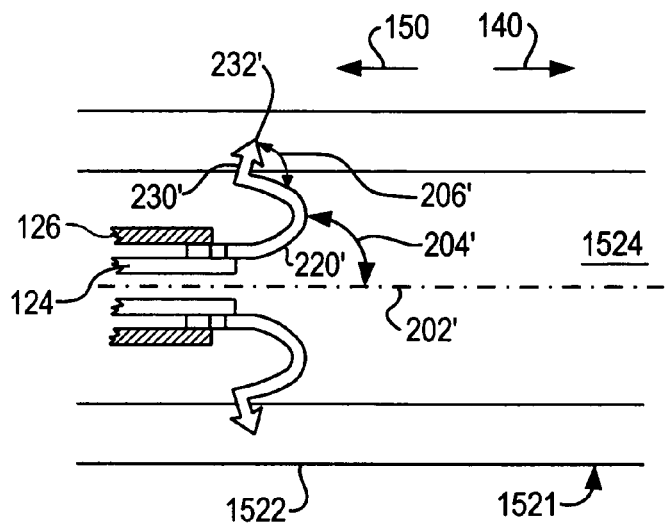
FIG. 83 is a cross-sectional view of the body tubing of FIG. 82, illustrated with the apparatus of FIGS. 11-17, but in conjunction with yet another illustrative embodiment of a gathering device, in a first stage of a procedure, constructed in accordance with the present invention.
Figure 84:
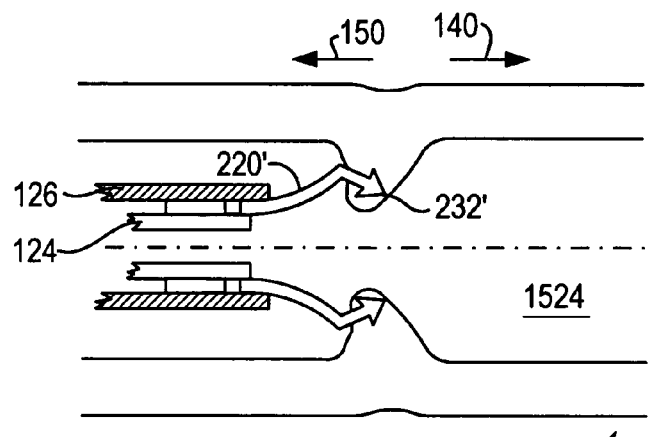
FIG. 84 is a cross-sectional view of the body tubing, apparatus, and gathering device of FIG. 83, in a second stage of a procedure, in accordance with the present invention.
Figure 85:
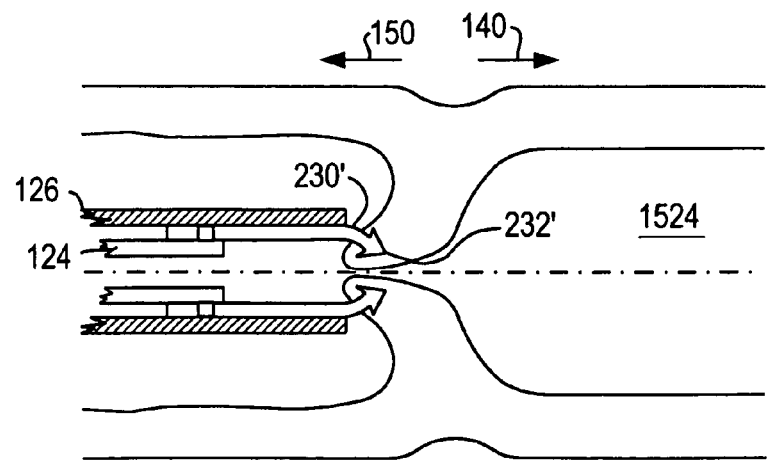
FIG. 85 is a cross-sectional view of the body tubing, apparatus, and gathering device of FIGS. 83 and 84, in a third stage of a procedure, in accordance with the present invention.

For example, with respect to a hole in a body cavity wall (e.g., hole 1424 in wall 1421, shown in FIGS. 80 and 81), the tissue from all sides of (or from completely around the circumference of) hole 1424 may be gathered together into a concentrated area and secured in that collapsed or condensed position, significantly, from only one side of hole 1424 using any of the methods and apparatus described hereinabove (e.g., exemplary retaining device 300).

Likewise, with respect to a portion of a lumen in a patient's body tubing (e.g., portion 1522 along lumen 1524 in vessel 1521, shown in FIGS. 82-86), the tissue from all sides of (or from completely around the circumference of) lumen 1524 substantially at portion 1522 may be gathered together into a concentrated area and secured in that collapsed or condensed position, significantly, from only one side of portion 1522 in lumen 1524 using any of the methods and apparatus described hereinabove (e.g., exemplary gathering device 200' and retaining device 300). Gathering device 200' may be substantially the same as device 200 described hereinabove, however orientation angles 204' (between longitudinal axis 202' and medial members 220') and angles 206' (between members 220' and distal members 230') may be altered such that free-end portions 232' more actively engage the tissue about lumen 1524, preferably at a substantially perpendicular angle to axis 202' (see, e.g., FIG. 83). This fully expanded configuration of device 200' allows the tissue about lumen 1524 of vessel 1521 at portion 1522 to be gathered and secured more effectively, as shown in FIGS. 83-86.

Figure 87:
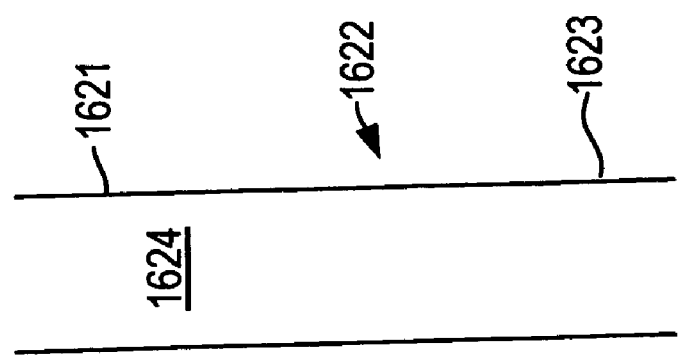
FIG. 87 is a cross-sectional view of a body cavity wall.

Similarly, with respect to a portion of a wall of tissue in a patient's body, (e.g., portion 1622 between portions 1621 and 1623 along wall 1624, shown in FIGS. 87 and 88), the tissue residing substantially at portion 1621 and the tissue residing substantially at portion 1623 may be gathered together into a concentrated area and secured in that collapsed or condensed position, significantly, from only one side of wall 1624 using any of the methods and apparatus described hereinabove (e.g., exemplary retaining device 300).

All of the devices of the present invention described hereinabove and hereinbelow may be constructed from various materials and construction techniques to achieve the desired geometries and functionalities. Functionality may be enhanced, for example, by using certain materials that are bioabsorbable, biodegradable, or dissolvable, such that no structure is present long term in the patient's body. In addition, materials may be used to promote tissue ingrowth or desired tissue response to add to the long term effectiveness of the implant. Certain materials may be used to aid in the delivery of these devices (e.g., their functionality), including, but not limited to, radiopacity, biocompatibility, and elasticity, for example. Furthermore, the materials may be used alone or in conjunction with each other to achieve the desired functionality or design intent, such as coating, cladding, assembling, plating, or dipping, for example. The following is a list of some of the materials that could be used, but is meant as a representative sample, not as a comprehensive list, the intent being to encompass all materials that could be suitably used for the design and purposes of the present invention: metals (stainless steel, 316L, 316LVM, BIODUR 108, DFT, HAYNES 188, INCONEL, L605, MP35N, NITINOL, niobium, PLATINUM, PLATINUM-IRIDIUM, TANTALUM, Ti-6AL-4V ELI, nickel-titanium alloy, cobalt chromium, Elgiloy®, Molybium®, tungsten, Titanium, Titanium alloys, Ceramics, PYROLYTIC CARBON, Pyrolite, etc.); polymers (polyesters, silicones, Polyurethane, Polycarbonates, Polyethylenes, Polyvinyl Chlorides, Polypropylenes, Methylacrylates, Biodegradable Copolymers, Copolymer Coatings, Pseudo-Polymers (Amino-Acids), Bioelastics, Organoids, Hydrogels, Thermoplastic-Fiber, etc.); and Biocompatible adhesives, sealants, or homeostasis products (fibrin, antilogous platelet gels, collagen-based, cyanoacrylate, thrombin, polyethylene glycol polymers, cross-linked albumin, protein based glues, etc.).

Thus, it is seen that apparatus and methods are provided that gather tissue in a patient's body and then secure the gathered tissue in a reduced area with some minimal securing structure. One skilled in the art will appreciate that the present invention can be practiced by other than the described embodiments, which are presented for purposes of illustration and not of limitation, and the present invention is limited only by the claims which follow.

What is claimed is:

1. A tissue holding structure, comprising:
    a ring defining a plane and an interior space; and
    a plurality of tissue penetrating members mounted on the ring and spaced from one another annularly along the ring, each of the tissue penetrating members extending from the ring to a free end;
    the structure having a first relaxed condition in which the tissue penetrating members project from a first side of the plane;
    the structure having a second deformed condition in which the tissue penetrating members project from a second side of the plane;
    wherein the tissue penetrating members are adapted to move from the first relaxed condition to the second deformed condition by passing the free ends through the interior space, and the tissue penetrating members are biased to move from the second deformed condition to the first relaxed condition with the free ends passing through the interior space.

2. Apparatus for closing an aperture in a wall of a tissue structure, comprising:
    (1) means for gathering together tissue that surrounds the aperture so that the tissue that has been gathered together substantially closes the aperture;
    (2) means for holding together the tissue that has been gathered together by the means for gathering, the means for holding comprising a ring defining a plane and an interior space, and a plurality of tissue penetrating members mounted on the ring and spaced from one another annularly along the ring, each of the tissue penetrating members extending from the ring to a free end, the structure having a first relaxed condition in which the tissue penetrating members project from a first side of the plane, the structure having a second deformed condition in which the tissue penetrating members project from a second side of the plane, the tissue penetrating members being adapted to move from the first relaxed condition to the second deformed condition by passing the free ends through the interior space, and the tissue penetrating members being biased to move from the second deformed condition to the first relaxed condition with the free ends passing through the interior space;
    (3) means for drawing tissue adjacent to the aperture into the means for gathering prior to operation of the means for gathering, wherein the means for drawing comprises:
        (a) means for passing through the tissue adjacent to the aperture; and
        (b) means for laterally expanding a portion of the means for passing after that portion of the means for passing has passed through the tissue.

3. The apparatus defined in claim 2 wherein the means for gathering engages the tissue from substantially only one side of the wall.

4. The apparatus defined in claim 2 wherein the means for holding engages the tissue from substantially only one side of the wall.

5. The apparatus defined in claim 2 wherein the means for gathering and the means for holding both engage the tissue from substantially only one side of the wall.

6. The apparatus defined in claim 2 wherein the means for gathering is removable from the tissue after operation of the means for holding.

7. The apparatus defined in claim 2 wherein the means for drawing further comprises: means for pulling the means for passing back in a direction opposite the passing so that the portion of the means for passing that has laterally expanded pulls adjacent tissue toward the means for gathering.

8. The apparatus defined in claim 7 wherein the means for drawing further comprises: means for laterally shrinking the portion of the means for passing that has laterally expanded after operation of the means for gathering to facilitate withdrawal of the means for passing from the tissue.

9. The apparatus defined in claim 2 wherein the means for gathering and the means for holding are adapted for use percutaneously.

10. The apparatus defined in claim 2 wherein the means for gathering and the means for holding are adapted for transcatheter use.

11. The apparatus defined in claim 2 wherein the tissue penetrating members move from the second deformed condition to the first relaxed condition by passing through an intermediate condition in which the tissue penetrating members are all directed substantially radially inwardly in the interior space.

12. Apparatus for closing a patent foramen ovale (PFO) in a patient, the apparatus comprising:

(1) means for gathering together tissue of the septum primum and septum secundum to close the PFO, said means for gathering comprising means for drawing a portion of the septum primum toward the right atrium prior to gathering the septum secundum, the means for drawing including structure adapted to pierce and pass through the portion of the septum primum from the right atrium to the left atrium, to laterally expand after passing through the portion of the septum primum, and to laterally shrink for withdrawal from the septum primum; and (2) means for holding together the tissue that has been gathered together by the means for gathering.

13. The apparatus defined in claim 12 wherein the means for gathering engages the tissue from substantially only the right atrium.

14. The apparatus defined in claim 12 wherein the means for holding engages the tissue from substantially only the right atrium.

15. The apparatus defined in claim 12 wherein the means for gathering and the means for holding both engage the tissue from substantially only the right atrium.

16. The apparatus defined in claim 12 wherein the means for gathering is removable from the tissue after operation of the means for holding.

17. The apparatus defined in claim 12 wherein the structure is adapted to laterally contract after operation of the means for gathering to facilitate withdrawal of the structure from the tissue.

18. The apparatus defined in claim 12 further comprising: an elongated structure for introducing the means for gathering and the means for holding into the right atrium from outside the patient's body via vasculature leading to the right atrium.

19. The apparatus defined in claim 18 further comprising: controls for operating the means for gathering and the means for holding, the controls being connected to the elongated structure so that they remain outside the patient's body.

20. The apparatus defined in claim 19 wherein the elongated structure comprises: linkages for operatively connecting the controls to the means for gathering and the means for holding.

21. The apparatus defined in claim 18 wherein the means for holding includes at least a portion that is selectively separable from the elongated structure.

22. The apparatus defined in claim 12 further comprising: an elongated structure for introducing the means for drawing, the means for gathering, and the means for holding into the right atrium from outside the patient's body via vasculature leading to the right atrium.

23. The apparatus defined in claim 22 further comprising: controls for operating the means for drawing, the means for gathering, and the means for holding, the controls being connected to the elongated structure so that they remain outside the patient's body.

24. The apparatus defined in claim 23 wherein the elongated structure comprises: linkages for operatively connecting the controls to the means for drawing, the means for gathering, and the means for holding.

25. A method of closing a patent foramen ovale (PFO), the method comprising:
(1) inserting a drawing tool to draw a portion of the septum primum toward the right atrium without substantially drawing the septum secundum toward the right atrium, the insertion step including piercing the drawing tool through the portion of the septum primum, passing a portion of the drawing tool through the portion of the septum primum from the right atrium to the left atrium, and laterally expanding the portion of the drawing tool in the left atrium;
(2) gathering together tissue of the septum primum and septum secundum to close the PFO;
(3) holding together the tissue- that has been gathered together; and
(4) laterally shrinking the expanded portion of the drawing tool and removing the drawing tool from the septum primum.

26. The method defined in claim 25 wherein the gathering is performed from inside the right atrium.

27. The method defined in claim 25 wherein the holding step is performed only from inside the right atrium.

28. The method defined in claim 25 wherein the gathering and the holding steps are performed from inside the right atrium.

29. The method defined in claim 25 wherein the drawing step further comprises pulling the laterally expanded portion of the drawing tool toward the right atrium.

30. The method defined in claim 25 wherein the gathering and holding steps are performed percutaneously.

31. The method defined in claim 25 wherein the gathering and the holding steps are performed via catheter means.

32. A method of closing a patent foramen ovale (PFO) in a patient, the method comprising:
(1) inserting means for gathering tissue and means for drawing tissue into the right atrium via vasculature leading to the right atrium;
(2) piercing the means for drawing through the septum primum;
(3) passing a portion of the means for drawing through the septum primum and into the left atrium;
(4) laterally expanding the portion of the means for drawing in the left atrium;
(5) first operating the means for drawing to draw tissue of the septum primum toward the right atrium without substantially drawing tissue of the septum secundum toward the right atrium;
(6) then operating the means for gathering to gather together tissue of the septum primum and the septum secundum to close the PFO;
(7) inserting means for holding tissue into the right atrium via vasculature leading to the right atrium;
(8) operating the means for holding to hold together the tissue that has been gathered together by the means for gathering; and
(9) laterally shrinking the expanded portion of the means for drawing; and
(10) removing the means for drawing from the right atrium.

33. The method defined in claim 32 further comprising: removing the means for gathering from the right atrium via the vasculature after the means for holding has been operated.

34. The method defined in claim 32 wherein the step of operating the means for gathering is controlled remotely from outside the patient's body.

35. The method defined in claim 32 wherein the step of operating the means for holding is controlled remotely from outside the patient's body.

36. The method defined in claim 32 wherein the step of operating the means for drawing is controlled remotely from outside the patient's body.

* * * * *

UNITED STATES PATENT AND TRADEMARK OFFICE
CERTIFICATE OF CORRECTION

PATENT NO.        : 8,114,123 B2
APPLICATION NO.   : 10/943352
DATED             : February 14, 2012
INVENTOR(S)       : Michael P. Brenzel et al.

Page 1 of 1

It is certified that error appears in the above-identified patent and that said Letters Patent is hereby corrected as shown below:

On the Title of the patent, (74) Attorney, Agent or Firm – "Lerner, David, Littenberg, Krumbolz & Mentlik, LLP" should read --Lerner, David, Littenberg, Krumholz & Mentlik, LLP--.

Signed and Sealed this
Ninth Day of April, 2013

Teresa Stanek Rea
*Acting Director of the United States Patent and Trademark Office*